US009994891B2

(12) United States Patent
Wende et al.

(10) Patent No.: US 9,994,891 B2
(45) Date of Patent: Jun. 12, 2018

(54) SAMPLE PROCESSING METHOD AND SAMPLE PROCESSING CARTRIDGE

(71) Applicant: QIAGEN GMBH, Hilden (DE)

(72) Inventors: Andy Wende, Hilden (DE); Rainer Dahlke, Kaarst (DE); Ralf Himmelreich, Langenfeld (DE); Thomas Rothmann, Hilden (DE); Michael Eberhard, Hilden (DE); Gerd Grosshauser, Pulheim (DE); Markus Jeziorski, Meierskappel (CH); Hans Attig, Hilden (DE); Josef Drexler, Hilden (DE); Eva Holzer, Hilden (DE)

(73) Assignee: QIAGEN GMBH, Hilden (DE)

( * ) Notice: Subject to any disclaimer, the term of this patent is extended or adjusted under 35 U.S.C. 154(b) by 669 days.

(21) Appl. No.: 14/350,095

(22) PCT Filed: Oct. 11, 2012

(86) PCT No.: PCT/EP2012/070211
§ 371 (c)(1),
(2) Date: Apr. 7, 2014

(87) PCT Pub. No.: WO2013/053855
PCT Pub. Date: Apr. 18, 2013

(65) Prior Publication Data
US 2014/0287955 A1   Sep. 25, 2014

Related U.S. Application Data

(60) Provisional application No. 61/545,983, filed on Oct. 11, 2011.

(30) Foreign Application Priority Data

Oct. 11, 2011  (EP) .................... 11008214

(51) Int. Cl.
C12Q 1/68    (2018.01)
B01L 3/00    (2006.01)
B01L 7/00    (2006.01)

(52) U.S. Cl.
CPC .......... *C12Q 1/6806* (2013.01); *B01L 3/5027* (2013.01); *C12Q 1/686* (2013.01); *C12Q 1/689* (2013.01); *C12Q 1/6888* (2013.01); *B01L 3/5082* (2013.01); *B01L 7/52* (2013.01); *B01L 2200/025* (2013.01); *B01L 2200/026* (2013.01); *B01L 2200/0689* (2013.01); *B01L 2200/16* (2013.01); *B01L 2300/0681* (2013.01); *B01L 2300/0816* (2013.01); *B01L 2300/0864* (2013.01); *B01L 2400/0487* (2013.01)

(58) Field of Classification Search
CPC .................................. C12Q 1/6806

USPC ......................................... 435/6.1
See application file for complete search history.

(56) References Cited

U.S. PATENT DOCUMENTS

| 8,067,017 B2 * | 11/2011 | Truong-Le | A61K 9/0019 |
| | | | 424/184.1 |
| 2008/0172025 A1 | 7/2008 | Tanaami et al. | |
| 2008/0293931 A1* | 11/2008 | Dunbar | C12Q 1/6806 |
| | | | 536/25.41 |
| 2009/0130658 A1* | 5/2009 | Barlag | B01L 3/5027 |
| | | | 435/6.12 |
| 2011/0177516 A1 | 7/2011 | Himmelreich | |

FOREIGN PATENT DOCUMENTS

| JP | 2006129869 A | 5/2006 |
| JP | 2008517259 A | 5/2008 |
| JP | 201088343 A | 4/2010 |
| WO | 2004036184 A2 | 4/2004 |
| WO | 2006042734 A1 | 4/2006 |
| WO | 2006071770 A2 | 7/2006 |

OTHER PUBLICATIONS

International Search Report received in corresponding PCT/EP2012/070211 dated Dec. 7, 2012.

* cited by examiner

*Primary Examiner* — Jezia Riley
(74) *Attorney, Agent, or Firm* — McBee Moore Woodward & Vanik IP, LLC; Susan McBee

(57) ABSTRACT

The present invention pertains inter alia to a method for analyzing a sample comprising biomolecules, which comprises the following steps:

A
a) lysing the sample to provide a lysed sample and optionally clearing the lysed sample;
b) contacting at least a portion of the lysed sample with a dry composition comprising reagents for performing the analytical method, thereby providing a reconstituted composition;
c) performing an analytical method using the reconstituted composition;

or

B
a) contacting the sample with a lysis solution thereby providing a lysis mixture;
b) using the lysis mixture to reconstitute a dry composition comprising reagents for performing the analytical method, thereby providing a reconstituted composition;
c) performing an analytical method using the reconstituted composition,
wherein the reconstituted composition is optionally cleared and wherein subsequent to step b) at least one step is performed which supports the lysis of the sample.

Furthermore, specifically adapted processing cartridges and systems are provided.

19 Claims, 13 Drawing Sheets a)

b)

SAMPLE PROCESSING METHOD AND SAMPLE PROCESSING CARTRIDGE

CROSS REFERENCE TO RELATED APPLICATIONS

This application is a § 371 National Stage Application of PCT/EP2012/070211, filed Oct. 11, 2012 which claims priority to EP 11008214.6, filed Oct. 11, 2011 which claims the benefit of U.S. Provisional Application No. 61/545,983, filed Oct. 11, 2011.

BACKGROUND

The present invention pertains to the field of biotechnology and provides methods for reconstituting a dry composition comprising reagents for performing an analytical method, clearing a lysate, analytic methods for detecting biomolecules using reconstituted dry compositions and specific cartridges that are useful for processing a sample.

DESCRIPTION OF RELATED ART

There is currently a great demand for rapid analytical methods processing a biological sample and detecting and analyzing biomolecules comprised therein. The prerequisite for such an analytical method is that the biomolecules to be analysed, e.g. nucleic acids, are made available for the analytical method in such a way that the biomolecules of interest are provided in an amount capable of being analyzed and in a sufficient purity for the intended analytical method. For analysing, e.g. detecting nucleic acids, e.g. a widely used method is the polymerase chain reaction (PCR), by which the nucleic acid of interest is amplified. PCR is an analytical method, since it is possible, by selecting specific primers, to identify the presence of corresponding sequences in the population of nucleic acids comprised in the sample. Furthermore, the PCR amplificates itself may be the subject of further analyses e.g. it can be detected, sequenced, identified or analysed otherwise. Isothermal nucleic acids amplification and detection reactions are well-known alternatives to PCR. Examples for this category of analytical methods are LAMP (loop mediated isothermal amplication), RPA (recombinase polymerase amplification), tHDA (helix dependend amplification), NEAR (nicking enzyme amplification reaction), TMA (transcription mediated amplification) and NASBA (nucleic acid sequence based amplification).

It is desirable to employ inexpensive, time-saving methods for such an analysis since it is frequently the case that larger amounts of different samples have to be processed simultaneously. Therefore, it is desireous to be able to analyse the target biomolecules without purifying them first and hence to be able to perform the analytical method with the crude lysate which comprises the biomolecules of interest. By overcoming the need to isolate the biomolecules first, time and costs can be saved. To be able to use the crude lysate in an analytical method such as an amplification reaction, the lysis conditions must be carefully chosen because if unsuitable conditions or buffer systems are chosen, the analytical method can not be performed with sufficient accuracy. In particular, it is important to reduce or neutralize contaminants that could inhibit the intended analytical method. A suitable lysis buffer which enables to use the crude lysate directly in an amplification reaction is e.g. described in US 2011/0177516. The lysis buffer disclosed therein comprises binders or thickeners such as PVP which bind to or neutralize PCR inhibitors comprised in the lysate. However, there is still a need to provide an improved method for providing a lysate that can be directly used in an analytical method such as an amplification method. In particular, there is a need to provide a lysis method which allows to remove contaminants that may potentially interfere with the intended analytical method more efficiently.

In order to be able to perform the analytical method cost effectively and also in non-specialized facilities, there is a need to provide an inexpensive, simply manageable complete biomolecule analysis process. Today, analytical methods involving the amplification of nucleic acids for diagnostic of infectious diseases or genetic testing of cancer detection and monitoring is a common method within diagnostic laboratories. Plenty of specialized devices make the tests easy to perform by automation of many protocol steps. The majority of testing currently occurs in centralized laboratories using non-portable and operationally complex instruments. Presently, tests generally require highly skilled individuals to perform the assays. As a result, the time taken between obtaining a sample suspected of containing a specific nucleic acid fragment and determining its presence or absence is often several hours and even days. However, as with other kinds of analytical tests, physicians and others often require results more quickly and obtainable in a convenient user-friendly format. Consequently, there is a need for a portable analysis system capable of performing nucleic acid testing quickly and conveniently. Meanwhile, so called 'integrated' devices are engineered, and also a trend for miniaturization took place in construction. This evolution led to "Lab-on-a-Chip" (LoC) systems, of which the most elaborated are capable to process a diagnostic test from sample to result. Thus, systems are available, wherein the analytical method is carried out in a minaturized system, e.g. a cartridge. Respective cartridges are e.g. described in WO2006/071770, US2009/0130658, WO 2006/042734 and DE 10 2008 004 646.

The respective cartridges often comprise the reagents necessary for performing the analytical method of interest in a dry form, preferably a freeze-dried form. Dry compositions of reagents are widely used in analytical methods, in particular in amplification reactions such as e.g. the polymerase chain reaction or for detecting other analytes such as proteins. Respective dry compositions usually comprise one or more or even all reagents necessary for the analytical method such as e.g. enzymes, detection compounds, e.g. labelled antibodies or probes, buffers, salts, oligonucleotides and the like. The use of respective dry compositions, in particular freeze-dried compositions, has the advantage that the dry compositions are stable during storage and therefore, respective freeze-dried compositions are often used in cartridges to provide all reagents necessary for the analysis method to be performed in the cartridge. Providing the reagents in a respective dry form has the advantage that the customer does not need to combine the necessary reagents himself. Instead, only a pre-determined amount of liquid such as water or a suitable buffer is added to reconstitute the dry reagents, thereby providing a reaction mix that is suitable for performing the intended analytical method once the sample comprising e.g. nucleic acids is incorporated. Here, it is important that a pre-defined amount of liquid is added for the reconstitution process in order to ensure that the reagents are provided in the suitable concentration. For this purpose, often pumps or dispensing devices are used in conjunction with the cartridges. Furthermore, respective cartridges are also designed and equipped with suitable reagents and components such as magnetic particles to allow a purification of the biomolecules of interest, in particular nucleic acids, from the sample prior to performing the intended analytical method such as in particular a PCR method. A purification is performed in these systems to ensure that the nucleic acids are provided in a sufficiently pure form to enable the analysis method such as in particular the amplification method. Thus, the known LoC systems have the drawback that the cartridges have a rather complex design and furthermore, also the process that is performed in the cartridge is usually rather complex in order to enable the performance of the analytical method. The present systems need several sample processing buffers and other solutions in order to perform the processing of the sample within the chip. Furthermore, complicated valves, pumps and other means are needed in order to process specific volumes of said buffers for sample processing. This increases the costs for the respective cartridges. Thus, there is a need for more simple methods to perform the intended analytical method using a respective cartridge system. Furthermore, there is a need to provide more simply designed cartridges that in particular can be produced at lower costs.

It is the object of the present invention to overcome at least one drawback of and/or to ameliorate the above described prior art methods and systems. Furthermore, it is the object of the present invention to address at least one of the above described needs.

SUMMARY

According to a first aspect of the present invention, an analytical method is provided for analysing a sample comprising biomolecules, wherein said method comprises the reconstitution of a dry composition comprising reagents for performing the analytical method. Here, the inventors have found a rapid method which allows to reconstitute a respective dry composition without the need to purify the biomolecules first or to use a reconstitution solution such as a reconstitution buffer or water in order to reconstitute the dry composition.

In a first sub-aspect A, said method is comprising the following steps:
 a) lysing the sample to provide a lysed sample and optionally clearing the lysed sample;
 b) contacting at least a portion of the lysed sample with a dry composition comprising reagents for performing the analytical method, thereby providing a reconstituted composition;
 c) performing an analytical method using the reconstituted composition.

The present inventors have surprisingly found that it is possible to reconstitute a dry composition comprising reagents for performing an analytical method by directly using the lysed sample. Thus, in contrast to the prior art methods, it is not necessary to reconstitute the dry composition by adding e.g. water or a suitable buffer prior to adding the lysed sample. Conversely, the lysed sample, which preferably is cleared from contaminants such as in particular precipitates, can be used directly for reconstitution. Thus, there is no need to purify the biomolecules first and/or to reconstitute the dry composition by adding a separate liquid.

Rather, after lysis, the lysed sample is contacted directly with the dry composition for reconstitution. This considerably saves time and makes the respective process particularly suitable for use in a processing cartridge as they are used in LoC systems. No separate reagents for purifying the biomolecules and/or for reconstituting the sample are needed. The whole method (respectively processing cartridge) can be operated with the lysed sample. Therefore, when performing the lysis of the sample with a lysis solution, only one solution is needed for conducting all demanding process steps. The sample may be advantageously directly collected in an appropriate lysis solution, thereby saving a further processing step. Thus, a surprisingly simple and rapid method is provided for performing an analytical method which involves the use of a dry composition comprising reagents for performing the analytical method of interest.

According to a second sub-aspect B, said is method comprising the following steps:
 a) contacting the sample with a lysis solution thereby providing a lysis mixture;
 b) using the lysis mixture to reconstitute a dry composition comprising reagents for performing the analytical method, thereby providing a reconstituted composition;
 c) performing an analytical method using the reconstituted composition,
 wherein the reconstituted composition is optionally cleared and wherein subsequent to step b) at least one step is performed which supports the lysis of the sample.

The inventors found that it is also possible to efficiently reconstitute the dry composition before the sample is lysed. In this variant, the lysis mixture comprising the sample mixed with a lysis solution is used for reconstituting the dry composition which accordingly, is provided as a reconstituted mixture which comprises besides the reagents for performing the analytical method the sample and the lysis solution. After reconstitution, at least one step, preferably a heating step, is performed in order to (fully) lyse the sample that is comprised in the reconstituted mixture. Said step may be performed prior to step c), e.g. as separate intermediate step. However, lysis may also be achieved or may be completed during performance of the analysis method. This is particularly feasible if the analysis method comprises a heating step. Thereby, the method is capable of saving process steps.

According to a second aspect, the present invention pertains to the use of a lysed sample, preferably a cleared lysed sample, or a sample mixed with a lysis solution for reconstituting a dry composition comprising reagents for performing an analytical method by adding the lysed sample or the sample mixed with the lysis solution to the dry composition and mixing.

As discussed above, the present inventors have found that it is possible to reconstitute a dry composition comprising reagents for performing an analytical method such as e.g. a PCR method by adding at least an aliquot of a lysed sample, preferably of the cleared lysed sample or the lysis mixture comprising the sample mixed with a lysis solution. Thereby, a reconstituted composition is provided that is suitable for performing the analytical method. By using directly the lysed sample, which preferably is cleared prior to use, has the advantage that time and reconstitution reagents can be saved. Furthermore, the inventors have found that it is possible to achieve an efficient reconstitution of the dry composition by adding a lysis mixture, comprising the sample and the lysis solution. Thereby, the reconstitution process can be considerably simplified.

According to a third aspect, the present invention pertains to a method for clearing a sample from precipitates, wherein the sample is contacted prior, during or after lysis with at least one solid support which binds to precipitates originating from the lysed sample, thereby forming a complex with the precipitates, and wherein said complex is optionally separated from the remaining sample.

This method is particularly efficient in providing a cleared lysed sample. The present inventors have developed methods that are particularly suitable for clearing a lysed sample from contaminants such as precipitates that could inhibit the analytical method. As is shown by the examples, the efficient binding of precipitates improves the performance of the subsequent analytical method, in particular when intending to perform an amplification reaction, as the respective methods can be inhibited by precipitates that are carried over from the lysed sample into the analytical reaction. Furthermore, as is shown by the examples, using said method is also suitable for clearing a reconstituted composition from respective inhibitory contaminants.

According to a fourth aspect, a method for elevating the pH value of an acidic sample is provided, said method comprising the addition of a molecular sieve, preferably a zeolite, to the sample to elevate the pH value of the acidic sample. This method can advantageously be used e.g. in order to adjust the pH value of a lysed sample from an acidic to a neutral to alkaline pH range.

According to a fifth aspect, the present invention pertains to a processing cartridge suitable for use in a method for analysing a sample comprising biomolecules according to the first aspect of the present invention, wherein the processing cartridge comprises a cartridge body and at least one reaction chamber which comprises a dry composition comprising reagents for performing an analytical method, wherein the cartridge body comprises a sample intake opening, at least one sample outlet and a fluid passageway that connects the sample intake opening and the sample outlet, wherein the sample outlet opens into the reaction chamber, wherein the cartridge is designed such that reconstitution of the dry composition comprised in the reaction chamber is achieved by a sample that enters the cartridge through the sample intake opening.

The inventors have developed a cartridge design, which is remarkably simple compared to prior art cartridges. The whole process that occurs within the cartridge is operated by the sample that enters the cartridge through the sample input opening. The sample is provided in a form suitable for reconstituting the dry composition so that the intended analysis method can be performed with adequate sensitivity and/or specificity. For that purpose, the sample is in one embodiment a pretreated sample, e.g. a lysed sample as described above. The pretreatment can advantageously occur in the vessel that is used for collecting the sample and which can be assembled to the processing cartridge so that the sample vessel opening is in fluid connection with the sample intake opening, thereby allowing entry of the pretreated sample into the cartridge body. The sample that enters the cartridge through the sample intake opening is preferably a lysed sample, more preferably a cleared lysed sample. Furthermore, the sample may be a lysis mixture comprising the sample and a lysis solution. In a respective lysis mixture, lysis of the sample is not completed yet. As is shown herein, lysis can be completed after reconstitution of the dry composition using said lysis mixture e.g. by a simple heating step that is performed during the analysis, e.g. a PCR reaction. Thus, advantageously, no separate means are provided in the processing cartridge for purifying the biomolecules comprised in the sample or means for dispensing a liquid such as water or a buffer from a reservoir into the reaction chamber in order to achieve the reconstitution of the dry composition. Conversely, reconstitution of the dry composition within the reaction chamber is achieved by the sample that enters the cartridge through the sample input opening. Due to its simple design, production of the cartridge is possible at very low costs. Furthermore, a respective simple cartridge design is less error prone than more complex designs.

According to a sixth aspect, a cartridge body is provided which is suitable for providing a fluid connection from a sample vessel that contains a fluid and can be assembled to the cartridge body, to at least one reaction chamber that can be assembled to the cartridge body or which is provided as integral part of the cartridge body, comprising
  a sample intake opening and a sample outlet,
  a sample passageway that connects the sample intake opening and the sample outlet,
  a sample vessel connection projection for connecting the sample vessel, wherein upon assembly of the sample vessel to said connection projection the sample intake opening is in fluid communication with the sample vessel,
  at least one reaction chamber connection projection for connecting a reaction chamber wherein upon assembly of the reaction chamber to said connection projection the sample outlet is in fluid communication with the reaction chamber and/or comprising at least one reaction chamber that is provided as integral part of the cartridge body
  wherein at least one fluid opening A is provided in the reaction chamber connection projection and/or in the reaction chamber and wherein said fluid opening A comprises a barrier, wherein said barrier allows the passage of air at least before said barrier comes into contact with a liquid but wherein said barrier substantially prevents the passage of liquid.

The cartridge body according to the sixth aspect of the present invention has the advantage that it comprises a cost-efficient, smart design that allows the easy reconstitution of a dry composition comprised in the reaction chamber as will be explained further in the detailed description of the present invention. The filling of the at least one reaction chamber by the sample that enters the cartridge body through the sample intake opening and arrives through the provided fluid passageway at the at least one reaction chamber is controlled by a barrier for liquids that is comprised in the fluid opening A. Said barrier preferably is a porous hydrophobic membrane, which allows the passage of air (at least before wetting) but which substantially does not allow the passage of sample. As soon as the sample reaches the hydrophobic membrane, it can not pass by said membrane and the filling of the reaction chamber automatically stops, thereby ensuring that the dry composition is reconstituted with a pre-determined adequate amount of sample, which preferably is a cleared lysed sample as described above. Said cartridge body can be advantageously used as cartridge body in the processing cartridge according to the fifth aspect of the present invention.

According to a seventh aspect, a method is provided for the production of a processing cartridge according to the fifth aspect of the present invention which comprises a reaction chamber comprising a dry composition, comprising reagents for performing an analytical method, said method comprising the following steps:
(a) making from polymer, a cartridge body with at least one channel and/or cavity to provide a fluid passageway between the sample intake opening of the cartridge body and the at least one sample outlet of the cartridge body;
(b) spotting reagents into at least one reaction chamber and drying the reagents therein, thereby providing a reaction chamber comprising a dry composition comprising reagents for performing an analytical method;

(c) closing the at least one channel and/or cavity of the cartridge body with a lid.

Due to the simple, effective design of the cartridge, its production is very cost-efficient.

According to a eight aspect, a system for performing an analytical method of a sample comprising biomolecules is provided, said system comprising a) a processing cartridge according to the fifth aspect of the present invention wherein the processing cartridge comprises at least one reaction chamber comprising a dry composition comprising reagents for the analytical method;

b) a vessel for receiving a sample comprising biomolecules, wherein the vessel can be assembled to the processing cartridge;

c) a processing device for receiving the processing cartridge comprising the vessel assembled thereto and for performing the analysis method in conjunction with the processing cartridge.

A respective system has due to the unique design of the cartridge and the possibility to process the sample within the sample vessel to provide a pretreated sample that is suitable for reconstituting the dry composition, e.g. a cleared lysed sample, the advantage that said system can automatically process a sample at low costs. Furthermore, as the processing device is rather simple and small in size, it can be used in any laboratory or facility where the sample is collected and analyzed e.g. in conjunction with point of care diagnostics.

According to a ninth aspect, an operating method for performing an analysis method using the system according to the seventh aspect of the present invention is provided, the method comprising:

a) connecting a vessel comprising a sample to the processing cartridge according to the fourth aspect of the present invention, wherein said processing cartridge comprises at least one reaction chamber comprising a dry composition comprising reagents for the analytical method;

b) inserting the processing cartridge with the sample vessel assembled thereto into a processing device; and c) starting a fully automatic assay.

The simple design of the processing cartridge and the feature that the whole process within the cartridge, including the reconstitution of the dry composition is operated by the pretreated sample, which preferably is a cleared lysate or a lysis mixture, which enters the cartridge from the vessel results in that a very cost-efficient and reliable method is provided. No manual working steps are needed to prepare the sample for the analytic method, apart from connecting the vessel comprising the collected sample to the cartridge and inserting the cartridge into the processing device. All substances and reagents (except for the sample that is preferably collected in a pretreatment composition, preferably a lysis solution) are provided in a closed, single-use cartridge. Furthermore, all processes are performed within the closed cartridge system. There is no direct contact of the user with substances that are potentially hazardous to health (sample and reagent wastes remain in the closed cartridge). The processing cartridge is small, simply structured and inexpensive to produce.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only. Various changes and modifications within the spirit and scope of the disclosed invention will become readily apparent to those skilled in the art from reading the following.

DETAILED DESCRIPTION OF A PREFERRED EMBODIMENT

Figure 1:
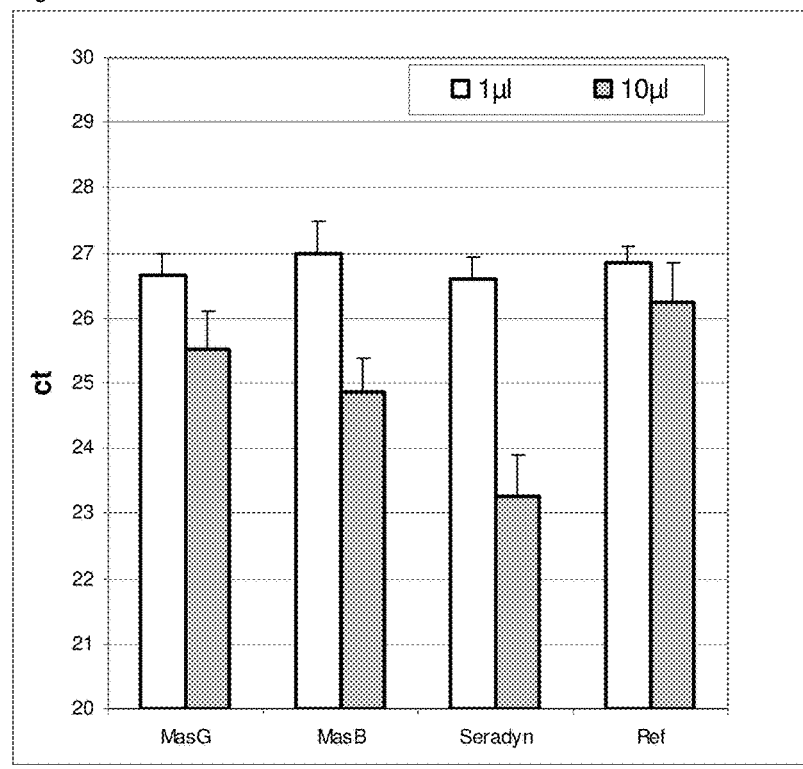
FIGS. 1-21 represents embodiments described herein.

In a first aspect, an analytical method is provided for analysing a sample comprising biomolecules, wherein said method comprises the lysis of the sample and the reconstitution of a dry composition comprising reagents for performing the analytical method.

In a first sub-aspect A, said method is comprising the following steps:

a) lysing the sample to provide a lysed sample and optionally clearing the lysed sample;

b) contacting at least a portion of the lysed sample with a dry composition comprising reagents for performing the analytical method, thereby providing a reconstituted composition;

c) performing an analytical method using the reconstituted composition.

Surprisingly, the inventors have found that it is possible to reconstitute a dry composition comprising reagents for performing the analytical method by using a lysed sample instead of liquids that are usually used for that purpose such as e.g. water or reconstitution buffers. Using the lysed sample for reconstitution provides a reconstituted composition that is suitable for performing the intended analytical method. Therefore, in contrast to prior art methods, it is advantageously possible to save considerable time and process steps by making the prior purification of the biomolecules and/or a separate reconstitution process of the dry composition obsolete. As is shown by the examples, an analytical method such as e.g. an amplification reaction can be efficiently performed when reconstituting a dry composition comprising the reagents necessary for performing said method using directly the lysed sample. That the lysate can be directly used for reconstitution was very surprising because usually, the reconstitution is achieved substantially by water or other liquids which do not comprise considerable amounts of contaminants that could interfere with the intended analytical method. That reconstitution is successful and provides a reconstituted composition that is suitable for the intended analysis method using even exclusively the lysed sample was very surprising.

The term "lysis" as used herein refers to the disruption, degradation and/or digestion of a sample. In a respective lysis step, biomolecules such as in particular nucleic acids can be released from cells or can be freed from other sample components such as e.g. proteins. Herein, we refer to a respective step to disrupt, degrade and/or digest a sample generally as lysis step, irrespective of whether biomolecules such as in particular nucleic acids are released from cells or whether the lysis is performed in order to release biomolecules such as nucleic acids e.g. from proteins or other substances comprised in the sample. Several methods are known in the prior art that allow to achieve an efficient lysis of different sample materials. Suitable lysis methods include but are not limited to mechanical, chemical, physical or enzymatic actions on the sample. Examples of respective lysis steps include but are not limited to grinding the sample in a bead mill, sonication, surface acoustic waves (SAW), repeated cycles of freezing and thawing, heating, the addition of detergents and/or the addition of protein degrading compounds such as e.g. protein degrading enzymes, e.g. hydrolases or proteases or salts. According to one embodiment, a protein degrading compound is used during lysis. According to a preferred embodiment, the protein-degrading compound is a proteolytic enzyme. A proteolytic enzyme refers to an enzyme that catalyzes the cleavage of peptide bounds, for example in proteins, polypeptides, oligopeptides and peptides. Exemplary proteolytic enzymes include but are not limited to proteinases and proteases in particular subtilisins, subtilases, alkaline serine proteases and the like. Subtilases are a family of serine proteases, i.e. enzymes with a serine residue in the active side. Subtilisins are bacterial serine protease that has broad substrate specificities. Exemplary subtilisins include but are not limited to proteinase K, proteinase R, proteinase T, subtilisin, subtilisin A, QIAGEN Protease and the like. Discussions of subtilases, subtilisins, proteinase K and other proteases may be found, among other places in Genov et al., Int. J. Peptide Protein Res. 45: 391-400, 1995. Preferably, the proteolytic enzyme is proteinase K. Preferably, the proteolytic enzyme is used under heating and/or agitation. Furthermore, one or more cell wall digesting enzymes can be used for lysis such as e.g. lysozyme, zymolase and/or pektinases. The suitable lysis method also depends on the intended analytical method. As the reconstitution of the dry composition comprising reagents for the analytical method is achieved by the addition of the lysed sample, it is important to ensure that the performed lysis does not introduce one or more inhibitors of the subsequent analysis method in a concentration that would inhibit the performance of the subsequent analytical method to an extent that the analytical method can not be adequately performed. The tolerable concentration depends on the analytical method to be performed, e.g. the used enzymes and their susceptibility to inhibitors and the sensitivity that is required for the adequate performance of the analytical methods. These parameters can also vary from sample to sample. Here, it must be considered that due to the fact that reconstitution is achieved by the addition of the lysed sample, usually a higher amount of biomolecules is introduced into the analytical method compared to methods wherein only a smaller aliquot of a lysed sample is added to an already reconstituted composition of dry reagents. This higher amount of biomolecules may also compensate for a potential inhibition of the analytical reaction by contaminants comprised in the lysed sample.

According to a second sub-aspect B, said method is comprising the following steps:
a) contacting the sample with a lysis solution thereby providing a lysis mixture;
b) using the lysis mixture to reconstitute a dry composition comprising reagents for performing the analytical method, thereby providing a reconstituted composition;
c) performing an analytical method using the reconstituted composition,
wherein the reconstituted composition is optionally cleared and wherein subsequent to step b) at least one step is performed which supports the lysis of the sample.

As described above, the inventors found that it is also possible to efficiently reconstitute the dry composition before the sample is completely lysed. In this variant, the lysis mixture comprising the sample mixed with a lysis solution is used for reconstituting the dry composition which accordingly, is provided as a reconstituted mixture which comprises besides the reagents for performing the analytical method the sample and the lysis solution. In the lysis mixture, lysis of the sample is at least incomplete. After reconstitution, at least one step, preferably a heating step, is performed in order to (fully) lyse the sample that is comprised in the reconstituted mixture. Said step may be performed prior to step c), e.g. as separate intermediate step. However, lysis may also be achieved or may be completed during performance of the analysis method. This is particularly feasible if the analysis method comprises a heating step as it is e.g. the case with a PCR. Thereby, this variant of the method according to the present invention is capable of saving process steps.

As both sub-aspects of the method according to the first aspect of the present invention share many common features, the common steps of both methods are discussed subsequently together.

According to one embodiment, the sample is contacted with a lysis composition, preferably a lysis solution, which comprises chemicals and/or reagents that achieve and/or promote the lysis of the biological sample. Depending on the composition of the lysis solution, lysis may be directly initiated. According to some embodiments, lysis is promoted and hence assisted by additional means, e.g. by performing a heating step. According to a preferred embodiment, lysis of the sample is achieved by contacting the sample with an appropriate lysis buffer and heating. As is shown above and in the examples, lysis of the sample may be achieved prior to contacting the lysed sample with the dry composition for reconstitution. However, lysis may also be achieved, respectively completed, after the sample and the lysis solution were added, preferably as mixture, to the dry composition. E.g. the reconstituted mixture can be heated in order to achieve and/or complete the lysis of the sample within the reconstituted mixture. This embodiment is particularly suitable when performing an analytical method that involves a heating step such as a PCR reaction.

According to one embodiment, which is particularly suitable if nucleic acids are the biomolecule of interest, a lysis solution is added to the sample which comprises as component (a) a nonionic surfactant or a mixture of non-ionic detergents. The non-ionic detergent preferably is selected from the group consisting of polyoxyethylene fatty alcohol ethers, polyoxyethylene alkylphenyl ethers, polyoxyethylene-polyoxypropylene block copolymers, polysorbates and alkylphenol ethoxylates, preferably nonylphenol ethoxylates, alkylglucosides and/or polyoxyethylene alkyl phenyl ethers. The term "fatty alcohol" in particular means for the purposes of the present invention alcohols having a chain length of from 6 to 22 carbon atoms, preferably 8 to 20 carbon atoms, preferentially 10 to 18 carbon atoms, particularly preferably 12 to 18 carbon atoms. Preference is in particular given to alcohols having 12, 14, 16 or 18 carbon atoms. Although the fatty alcohols may be mono- or polyunsaturated, they are preferably saturated fatty alcohols. The term "polyoxyethylene" in particular means for the purposes of the present invention an HO—(CH2CH2O)n unit, with n being preferably an integer from 2 to 150, further preferably from 4 to 120, still further preferably from 8 to 80, and most preferably an integer selected from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50. Preferred examples of suitable polyoxyethylene fatty alcohol ethers are polyethoxylated lauryl, cetyl, oleyl, or stearyl alcohols which may be used alone or as mixture. According to a preferred embodiment of the invention, the at least one polyoxyethylene fatty alcohol ether comprises a fatty alcohol component having from 6 to 22 carbon atoms and a polyoxyethylene component having from 2 to 150 (CH2CH2O) units. Preferably, the polyoxyethylene fatty alcohol ether is selected from the group consisting of polyoxyethylene lauryl ether, polyoxyethylene cetyl ether, polyoxyethylene stearyl ether and/or polyoxyethylene oleyl ether. As alkylglucoside, preferably a non-ionic detergent from the group of the polysorbates, preferably polysorbate 20 (Tween 20), polysorbate 40 or polysorbate 80, more preferred polysorbate 20 is used. Preferred examples of polyoxyethylene alkyl phenyl ethers include Triton X-100 and Nonidet P-40. Preferably, at least two respective non-ionic detergents are comprised in the lysis solution. According to one embodiment, component (a) in the lysis solution is selected from the group consisting of Tween, Triton X 100, Nonidet P40 (nonylphenylpolyethylenglycol), and Brij58. Preferably, at least two respective non-ionic detergents are comprised as component (a) in the lysis solution. The concentration of the nonionic surfactant or the mixture of non-ionic detergents in the lysis solution employed is between 0.05 and 5%, preferably between 0.1% and 2%, more preferably between 0.2% and 1.5% and most preferably between 0.4% and 1%. Preferably, Triton X-100 and/or Tween 20 are comprised as component (a) in the lysis solution.

As component (b) the lysis solution comprises at least one polymer which prevents or reduces an inhibition of the subsequent analytical method. Thus, the incorporation of the polymer to the lysis solution has the effect that the subsequent analysis method such as e.g. an amplification reaction shows an improved performance when said polymer is incorporated into the lysis solution compared to when said polymer is not incorporated into the lysis solution. It is assumed that the polymer prevents or reduces the inhibition by unspecifically complexing potential inhibitors. Which compounds act as inhibitors also depends on the analytical method that is subsequently performed. E.g. typical inhibitors of a nucleic acid amplification reaction which usually originate from the sample comprising the nucleic acids include but are not limited to proteoglycans, proteins and sugars. The polymer is comprised in the lysis solution preferably in a concentration in the range of from 0.05 to 0.5%, preferably 0.085% to 0.2%. Also a mixture of polymers can be used. According to one embodiment, the polymer acts as a binder and/or thickener and preferably is selected from polyvinylpyrrolidone (PVP), polyoxazoline, polyethylene glycol, polyvinyl alcohol and Luvitec. Preferably, polyvinylpyrrolidone is incorporated into the lysis solution. Suitable binders and/or thickeners that can be used for this purpose are also described in WO 2010/003493. As is shown in the examples, such binders and/or thickeners such as PVP is very efficient in preventing the inhibition of amplification reactions. Additional compounds for preventing or reducing inhibitory effects of contaminants comprised in the lysed sample or the cleared lysed sample can also be incorporated into the lysis solution.

As component (c) the lysis solution may comprise at least one enzyme, preferably a proteolytic enzyme. Suitable proteolytic enzymes are described above. It is preferred to employ a thermophilic proteinase, especially preferably a thermophilic proteinase selected from among proteinase K or subtilisin. It is very especially preferred to use a thermophilic proteinase K in the lysis solution. The proteinase is preferably employed in such an amount that it provides from 0.5 to 10 µunits, preferably from 1.5 to 4 µunits (international units) per milliliter of lysis solution. However, the proteolytic enzyme may also be added separately.

According to one embodiment, the lysis solution comprises as component (d) at least one chelating agent for divalent cations. Suitable chelating agents include but are not limited to diethylenetriaminepentaacetic acid (DTPA), ethylenedinitrilotetraacetic acid (EDTA), ethylene glycol tetraacetic acid (EGTA) and N,N-bis(carboxymethyl)glycine (NTA). According to a preferred embodiment, EDTA is used. As used herein, the term "EDTA" indicates inter alia the EDTA portion of an EDTA compound such as, for example, $K_2$EDTA, $K_3$EDTA or $Na_2$EDTA. Using a chelating agent such as EDTA has the advantageous effect that nucleases such as DNases and RNases are inhibited. The chelating agent preferably is employed in a concentration of 0.5 mM to 5 mM, preferably 0.75 mM to 2 mM, most preferred 1 mM to 1.5 mM in the lysis solution. Preferably, EDTA is used.

According to one embodiment, the lysis solution comprises as component (e) at least one buffer substance. The buffer substance should be capable of buffering the lysis solution at a pH range that is compatible with the pH range that is required for performing the subsequent analytical method. This, as the pH of the lysed sample is strongly effected by the solution that is used for lysis and the lysed sample is used for reconstituting the dry composition comprising the reagents for the analytical method. Preferably, a buffer is used in the lysis solution so that the pH of the solution is between 7.5 and 11, more preferred 7.5 to 9. Respectively buffered lysis solutions are particularly suitable for reconstituting a dry composition comprising reagents suitable for performing a nucleic acid amplification reaction. The pH buffer substance can be comprised in the lysis solution in a concentration of 5 mM to 100 mM, preferably 10 mM to 80 mM, more preferably 30-50 mM. Preferably, the buffer substance is selected from the group consisting of Tris, MOPS, HEPES or phosphate.

A particularly preferred lysis solution comprises
   as component (a) a mixture of two non-ionic detergents, preferably Polysorbate 20 (Tween 20) and nonylphenylpolyethylenglycol (Nonidet P40), wherein each non-ionic detergent is comprised in a concentration of 0.2% to 0.6%, preferably 0.4% to 0.5%;
   component (b), the polymer, which preferably is PVP, in a concentration of 0.05% to 0.15%, preferably 0.1%;
   optionally a proteolytic enzyme such as proteinase K as component (c);
   as component (d) EDTA in a concentration below 1.5 mM;
   as component (e) a buffer substance, preferably TRIS, in a concentration of 7.5 mM to 20 mM, preferably 10 mM.

The pH value of the respective lysis solution preferably is approx. between 8.0 and 9.0, preferentially at pH 8.5.

A lysis solution as described above is particularly effective in lysing a sample when being combined with a heating step. For this purpose, the lysis mixture comprising the sample and the lysis solution is heated for at least 3 min, preferably at least 5 min to a temperature of at least 90° C., preferably at least 95° C. Preferably, the heated sample is then cooled down to a temperature below 50° C., more preferably it is cooled down at least down to room temperature. Here, it was found that a respective cooling step promotes the formation of precipitates which are composed of respectively constitute themselves contaminants. The efficient precipitate formation and removal/binding of the precipitates by performing a clearing step as is described below, provides a remaining lysed sample from which contaminants were efficiently depleted. If the lysis solution comprises and/or is used in combination with a proteolytic enzyme, it is preferred to incubate the lysis mixture at temperatures suitable for the proteolytic enzyme to work, e.g. at a temperature below 70° C., preferably below 65° C., more preferably below 60° C., preferably combined with agitation. After said incubation, the heating step at higher temperatures is performed. Such a heating step is also referred to as boiling lysis herein. This sequence of process steps for achieving an efficient lysis of the sample has the advantage that the sample is efficiently lysed and that the proteolytic enzyme is denatured. The described lysis solution is in particular compatible for performing an amplification reaction such as a PCR as it does not comprise components in a concentration that would substantially inhibit a respective amplification reaction.

After the sample has been contacted with the lysis composition, the resulting mixture preferably is agitated in order to ensure a thorough mixture. Mixing can be assisted by vortexing, the introduction of gas such as air into the mixture or by magnetic stirring as will be described in further detail below. According to one embodiment, the lysis solution comprises at least one magnetic stirring bar that can be used to assist the mixing of the sample when using a magnet to move the stirring bar.

In order to improve the performance of the subsequent analytical method, in particular when performing an amplification reaction such as a PCR reaction, it is preferred to clear the lysate prior to contacting it with the dry composition for reconstitution. Hence, according to this embodiment, the reconstitution of the dry composition involves the contacting of the dry composition with at least a portion (aliquot) of the cleared lysed sample and mixing. Several options exist to clear the lysed sample. Non-limiting examples will be described below. Furthermore, a respective clearing step is also advantageously to remove and/or inactivate contaminants that are comprised in the reconstituted composition. As described above, in the method according to sub-aspect B of the method according to the first aspect of the present invention, lysis of the sample is achieved and/or completed after the dry composition has been reconstituted with the lysis mixture. Hence, contaminants that originate from, respectively are released during the lysis of the sample such as e.g. proteoglycans, proteins and sugars are released into the reconstituted composition and the respective contaminants may form precipitates therein, in particular if a heat treatment as described above is performed. According to one embodiment, the respectively reconstituted composition is cleared prior to performing the analysis method. Several options exist to clear the reconstituted composition. Non-limiting examples will be described below.

According to one embodiment, the sample is contacted prior, during or after lysis with means for removing contaminants that originate from the lysed sample. Thereby, a cleared lysed sample or a cleared reconstituted composition can be provided. Not all contaminants need to be removed. Rather, the amount of contaminants only needs to be removed to a level so that the intended analytical method can be adequately performed and in particular provides the necessary sensitivity and/or specificity. According to one embodiment, chemical reagents are used to remove or inactivate inhibitors of the subsequent analysis method. Suitable compounds such as polymers, in particular PVP were already described above. It is preferred to add these reagents prior to or during lysis in order to achieve an efficient removal of the contaminants directly during lysis. They are preferably incorporated into the lysis solution.

A major source of contaminations, in particular when processing a cell containing sample, is the formation of precipitates during lysis. Respective precipitates are in particular formed when the sample is heated during lysis. The carry-over of precipitates from the lysed sample into the analytical method such as e.g. an amplification reaction or a detection reaction can severely disturb said analysis method and/or the interpretation of the obtained results. Therefore, it is advantageous to complex respective precipitates and preferably separate the complexes from the remaining lysed sample, e.g. to provide a cleared lysed sample. Separation can be assisted e.g. by sedimentation or centrifugation. The precipitates may e.g. sediment at the bottom of the tube, leaving behind a supernatant which corresponds to the cleared lysate or the cleared reconstituted composition if said step is performed for that purpose. Sedimentation can be accelerated and improved e.g. by centrifugation. However, it is preferred to assist the separation of the precipitates. Already the complexing of the precipitates has a clearing effect, as contaminants are removed from the remaining sample. However, it is preferred to separate at least a portion of the contaminants from the remaining sample.

According to one embodiment, means are provided prior, during or after lysis for removing precipitates, thereby providing a cleared lysate or a cleared reconstituted composition. The term removing as used in this conjunction means that the amount of precipitates is at least reduced to an extent that the subsequent analytical method can be adequately performed. According to one embodiment, at least a portion of the lysate and/or at least a portion of the reconstituted composition wherein the step for supporting or even achieving the lysis of the sample had been performed, is passed through means that can hold back or remove precipitates during passage of the lysed sample or the passage of the reconstituted composition. Suitable means may be selected from the group comprising filter materials, membranes or layers or fillings of particles which bind precipitates. The lysed sample or the reconstituted composition passes through said means and precipitates are caught, respectively are held back by said means thereby providing a cleared sample once the sample has passed the filter. Said means such as e.g. a filter or membrane may be porous. The pores should be sufficiently small to efficiently hold back and thus remove precipitates that are present in the lysed sample or the reconstituted composition.

According to a preferred embodiment, the sample is contacted prior, during or after lysis with at least one solid support which binds precipitates, thereby forming a complex with the precipitates. Of course, also more than one complex can be formed, e.g. when using particles such as beads as solid support. Thus, term "complex" as used herein also refers to a plurality of complexes. Binding to the solid support preferably is unspecific and is achieved by adsorption. The complex is preferably separated from the remaining lysate, respectively the remaining reconstituted composition thereby providing a cleared lysate. Separation of the complex can be assisted by sedimentation, centrifugation or magnetic separation if a magnetic solid support is used. E.g. the complex can be concentrated at the bottom of the vessel and the supernatant, which corresponds to the cleared lysed sample, can be obtained. Binding the precipitates to the solid support assists the sedimentation of the complex and hence alleviates the removal of the precipitates from the remaining sample. However, as is shown in the examples, the addition of the solid support is also beneficial and provides a clearing effect in that the inhibitory effect of comprised contaminants such as precipitates is reduced, if the complexes are not removed but hence, are present during the analytical method. Apparently, complexing the precipitates by binding them to the solid support already provides a beneficial effect because the bound precipitates are not accessible and hence inactivated.

According to one embodiment, the solid support is selected from the group consisting of particles, plates and other particulate matter. According to one embodiment, the solid support comprises a surface which binds to contaminants, in particular precipitates, that are present in the lysate or the reconstituted composition. The term "binding" is used in a broad sense and refers to any interaction of the contaminants, in particular the precipitates with the solid support that allows to remove at least a portion of said contaminants together with the solid support. Binding preferably is achieved by adsorption.

According to one embodiment, mineral particles comprising or consisting of metal oxides are used as solid support for clearing the lysed sample or for clearing the reconstituted composition. Examples of suitable solid supports include but are not limited to solid supports having a silica surface such as e.g. silica particles or glass particles and polymeric supports. According to one embodiment, the solid support has a hydrous siliceous oxide adsorptive surface. However, the solid support may also comprise one or more ligands to provide a suitable surface for binding the precipitate or to improve binding of the precipitates. According to one embodiment, the ligands are selected from the group consisting of ion exchange groups preferably from the group of cation exchange groups such as carboxyl groups, sulfonate groups and silane ligands. Also combinations of respective ligands can be used. The solid support may additionally or alternatively comprise ligands or compounds on its surface which bind inhibitors of the downstream analysis method, e.g. inhibitors of an amplification reaction. Suitable examples are described above. Preferably, the solid support has a surface comprising carboxyl groups.

Exemplary solid supports providing a surface which are suitable for removing precipitates from the lysed sample include small spheres, also known as beads or particles, for example made of glass, silica, polymers or coated materials. In an especially preferred embodiment, the solid support such as the particles is magnetic. However, it is also within the scope of the present invention to modify e.g. the inner surface of the consumable that is used to receive the sample, such as, for example, a vessel. If at least a portion of the inner wall of the vessel that is in contact with the sample comprises respective ligands, the precipitates can bind, preferably adsorb, to said surface and are thereby immobilized to the sample wall. This allows to recover a cleared lysed sample, e.g. as supernatant, in which the amount of precipitates is reduced.

Binding of contaminants such as in particular precipitates to the solid support, respectively the surface provided for binding said contaminants, occurs under conditions wherein the contaminants bind to the solid support but wherein the biomolecules of interest do not or bind to a lesser extent than the biomolecule of interest. Hence, the used lysis conditions are selective in that predominantly the contaminants such as in particular precipitates bind, preferably adsorb, to the solid support, respectively the surface, but wherein there is no substantial binding of the biomolecules of interest so that they remain in a sufficient amount in the lysed sample or in the reconstituted composition to allow performing the intended analytical method.

Preferably, the solid support for binding the precipitate is comprised in the lysis solution. Thereby, it is ensured that any precipitates that are formed upon lysis of the sample are directly bound to the solid support upon their formation, thereby forming a complex. Thereby, precipitates are depleted from the remaining sample. Performing the lysis in the presence of the solid support that is used for removing contaminants such as precipitates improves the achieved clearing result. This probably as precipitates can be directly bound while they are being formed. This irrespective of whether lysis is achieved prior to reconstitution of the dry composition, or afterwards.

According to one embodiment, the solid support comprises or is a molecular sieve. A molecular sieve is a material containing small pores of a precise and uniform size that may be used as an adsorbent. Preferably, the molecular sieve comprises aluminosilicate minerals, clays, porous glasses, microporous charcoals, zeolites, active carbons, or synthetic compounds that have open structures through which small molecules, such as water can diffuse. As is shown by the examples, molecular sieves such as zeolites are particularly effective in removing contaminants such as precipitates from a lysed sample. The molecular sieve may be added to the lysis composition which preferably is a lysis solution. They may also be used in addition to the solid supports described above.

When processing acidic samples, such as vaginal swab samples using a molecular sieve such as a zeolite as solid support has the specific advantage that zeolites are capable of elevating the pH value of the lysed sample and/or the lysis mixture. This is beneficial as many analysis methods such as e.g. amplification reactions do not work properly at acidic pH values. The buffer substances that are often comprised in the dry composition comprising reagents necessary for performing the amplification reaction are often not capable to maintain the pH value of the reconstituted composition in the desired, respectively needed pH range due to the amount of acidic lysed sample, respectively acidic lysis mixture that is added for reconstitution. This problem can be overcome when incorporating zeolites during the preparation of lysis mixture and in particular during preparation of a cleared lysate. E.g. the addition of zeolites allows to elevate the pH value from an acidic pH value to a pH value between 7 and 9.5, preferably 7.5 to 9, thereby additionally improving the performance of the analytical method which requires a pH value in a respective range such as e.g. an amplification reaction, in particular a PCR. Hence, according to one embodiment, at least one type of solid support is added prior, during or after lysis which has the effect that the pH value of the lysed sample is elevated. This embodiment is particularly suitable when processing acidic samples having a pH below 7, below 6.5, below 6, below 5.5, below 5 or below 4.5. Preferably, a molecular sieve, more preferred zeolites, are used for this purpose. The molecular sieve can also be added in addition to other solid supports that bind precipitates such as carboxylated particles.

As discussed above, the solid support is preferably magnetic. Preferably, the solid support is incorporated in the lysis composition, preferably the lysis solution. When using magnetic particles as solid support in junction with a magnetic stirring bar, the agitation during lysis can be achieved very effectively. Said method may then correspond to the one described in DE102007045474, herein incorporated by reference. According to one embodiment, the lysis solution comprises a multiplicity of magnetic particles as solid support as well as at least one magnetic and/or magnetizable central element, which preferably is configured in the shape of a rod, dumbbell and/or ellipsoid which is used as stirring bar. The magnetic and/or magnetizable central element is larger than the multiplicity of the magnetic particles. The magnetic particles are distributed in the lysis solution that is mixed with the sample. They subsequently accumulate on the at least one central element. Stirring and/or mixing using the magnetic material is assisted by the use of at least one external magnet, e.g. a permanent magnet or electromagnet, which is configured to interact with the magnetic material. As magnetic particles, preferably a magnetic solid support as described above is used, because respective magnetic particles additionally provide a beneficial clearing effect.

According to one embodiment, the clearing step additionally or alternatively involves the use of at least one compound or composition that binds to and/or neutralizes one or more inhibitors of the subsequent analysis method, in particular inhibitors of an amplification reaction. Preferably, said compound or composition is comprised in the lysis solution that is added to the sample for lysis.

In a preferred embodiment, lysis and reconstitution of the sample is achieved by the following steps:
(i) contacting the sample with a lysis solution as described above and a solid support for removing precipitates, thereby forming a lysis mixture; preferably, the mixture is agitated, preferably vortexed to provide a homogeneous mixture;
(ii) heating the mixture to a temperature of at least 50° C., at least 60 C, at least 70° C., at least 80° C., preferably at least 90° C. more preferably at least 95° C.; this heating step promotes or completes the lysis of the sample;
(iii) optionally cooling the lysed sample to a temperature below 50° C., preferably down to room temperature;
(iv) clearing the lysed sample by separating the complexes comprising the solid support and the formed precipitates; and
(v) using the cleared lysate for reconstituting the dry composition.

Precipitates in particular are formed due to, respectively during the heating process. Incorporating the solid support directly into the lysis mixture, e.g. by adding it to the lysis solution, has the advantage that the precipitates can bind, e.g. adsorb, directly to the solid support upon formation and/or release. The optional cooling step (iii) promotes the formation of precipitates and hence improves the lysate clearing. To ensure that precipitates are efficiently removed by binding them to the solid support, the lysis mixture is preferably agitated, e.g. by magnetic stirring. This increases the chance that contaminants such as precipitates come into contact with the solid support and accordingly form a complex therewith which can be easily separated. To assist agitation, a magnetic stirring bar may be incorporated in the lysis mixture. A respective magnetic stirring bar is preferably already incorporated into the lysis solution. This embodiment is simple and consumer friendly, because a sample collection vessel may be pre-equipped with a lysis composition such as the lysis composition described above and a magnetic stirring bar.

In a further embodiment, lysis and reconstitution of the sample is achieved by the following steps:
(i) contacting the sample with a lysis solution and a solid support for removing contaminants, preferably precipitates, thereby forming a lysis mixture;
(ii) using the lysis mixture for reconstituting the dry composition;
(iii) heating the reconstituted composition to a temperature of at least 90° C., preferably at least 95° C. in order to achieve or complete the lysis of the sample;
(iv) optionally cooling the reconstituted composition comprising the lysed sample to a temperature below 50° C.; as discussed above, this optional cooling step assists the precipitate formation and hence the clearing and
(v) clearing the reconstituted composition by separating the formed complex comprising the solid support and precipitates thereby providing a cleared reconstituted composition.

Here, lysis is achieved, respectively completed after the dry composition was already reconstituted. This can save time, in particular when intending to perform a hot start PCR reaction. The heating step performed in (iii) already activates the hot start polymerase, thereby making a further heating step for activating the during the actual PCR obsolete.

In a further embodiment, lysis and reconstitution of the sample is achieved by the following steps:
(i) contacting the sample with a lysis solution and a solid support for removing contaminants, preferably precipitates, thereby forming a lysis mixture;
(ii) using the lysis mixture for reconstituting the dry composition;
(iii) subjecting the reconstituted composition to an amplification reaction which comprises at least one heating step involving a temperature of at least 90° C., preferably at least 95° C., preferably for at least 3 min, more preferably at least 5 min.

This method is very quick and also leads to acceptable results, depending on the processed sample. Here, also the lysis mixture is used for reconstitution of the dry composition. However, lysis of the sample is achieved or completed during the amplification reaction, e.g. during the initial heating of the sample, e.g. a heating step that is performed in order to activate the enzyme, e.g. for performing a hot start. According to this embodiment, the complexes comprising the solid support and the contaminants, such as in particular precipitates, may remain in the reconstituted composition and are not separated. As is shown by the examples, this embodiment also works with certain samples and has the advantage that further process steps become obsolete. Thus, already the presence of the respective solid support provides a significant improvement, even if the complexes are not removed from the reconstituted composition. However, according to one embodiment, the solid support is separated from the remaining sample, here the reconstituted composition, once the precipitates were bound.

The dry composition comprises one or more reagents necessary for performing the intended analysis method. Preferably, the dry composition comprises at least one protein, preferably an enzyme. Which reagents are comprised in the dry composition depends on the biomolecule to be analysed, e.g. detected and the intended analysis method. Suitable examples are described below.

According to one embodiment, the dry composition is a freeze-dried composition. Freeze-dried compositions are widely used for providing reagents necessary for analytical methods in a storable form. Respective freeze-dried compositions are in particular used in the field of biotechnology, in order to provide reagents necessary for the intended analysis method in a prepared and thus easy to use form. Respective freeze-dried compositions often comprise at least one biological product, e.g. selected from the group comprising nucleic acids such as oligonucleotides, proteins, antibodies, enzymes and the like. Methods for preparing respective freeze-dried compositions as well as suitable additives that stabilise the comprised reaction compositions, in particular biochemical components such as proteins are well-known in the prior art (see e.g. Freeze-Drying/Lyophilization of Pharmaceutical and Biological Products, Second Edition, WO 01/92569, WO 2010/001162, US 2010/0068716 and US 2010/0159529) and thus, need no detailed description here. The dry composition that is used in the method according to the present invention is a storable composition. Preferably, it is suitable for long-term storage. According to one embodiment, the dry composition is stable during storage for a time period of at least 3 months, at least 6 months, at least 10 months or at least 12 months. Preferably, the dry composition is stable for a time period of 3 to 18 months or 6 to 12 months. According to one embodiment, the dry composition comprises at least some of the chemical and/or biochemical reagents necessary for conducting the intended analysis method. Preferably, it comprises all of the necessary reagents because upon addition of the lysed sample, preferably the cleared lysed sample, the composition is ready for performing the analytical method. This is particularly advantageous when using the method e.g. in a LoC system as will be described below. According to a preferred embodiment, the dry composition comprises at least some, preferably all, of the reagents necessary for conducting an amplification reaction, preferably a PCR reaction. As discussed above, respective dry compositions, in particular freeze-dried compositions, are widely used to provide the reagents necessary for an amplification reaction in form of a so-called master mix, in a storable form. When intending to perform the amplification reaction, the dry composition only needs to be reconstituted using the lysed sample to form the amplification reaction mixture, wherein, however, optionally further reagents can be added e.g. if not all reagents were already comprised in the dry composition, what is, however, preferred. When indenting to perform an amplification reaction such as e.g. a PCR reaction, the dry composition comprises one or more, preferably all reagents selected from the group consisting of a polymerase, a reaction buffer suitable for performing an amplification reaction and dNTPs. Preferably, it also comprises primers and/or labelled probes which allow e.g. the detection the presence or absence of one or more target nucleic acids that are, e.g., indicative of a certain disease or infection. Further additives such as enzymes and salts may also be comprised. Furthermore, the dry composition may comprise a magnetic material to assist the reconstitution process by enabling the mixing of the composition during reconstitution by the aid of a magnet. After reconstitution using the lysed sample, preferably the cleared lysed sample, and optionally the addition of further additives, the resulting reconstituted composition is ready for performing the intended analytical method, e.g. effecting amplification of a target nucleic acid in case a dry composition suitable for use in an amplification, e.g. a PCR reaction, is provided. According to one embodiment, the dry composition comprises reagents suitable for use in an analytical method wherein said analytical method may be any chemical and/or biotechnological method that can be used to analyse a sample comprising a biomolecule of interest. Exemplary analytical methods are described below.

According to one embodiment, at least 60%, at least 70%, at least 80%, at least 90%, at least 95% or 100% of the liquid that is used for reconstitution is provided by the lysed sample, which preferably is a cleared lysed sample, or the lysis mixture. Reconstitution can be advantageously achieved exclusively by addition of the lysed sample, which preferably is cleared lysed sample, or the lysis mixture. According to one embodiment, at least an aliquot of the cleared lysate that was obtained as described above is contacted with the dry composition for reconstituting the dry composition. In order to ensure that the reconstituted composition comprises the reagents in a concentration appropriate for the intended analysis method, a predetermined amount of lysed sample or lysis mixture is added to the dry composition. Said predetermined amount is chosen such so that in the reconstituted composition, the reagents are comprised therein in a concentration suitable for performing the intended analysis method, e.g. an amplification reaction. The reconstitution process can be assisted by agitation e.g. by pipetting the resulting mixture up and down, stirring, shaking or vortexing. According to one embodiment, mixing is achieved by using a magnet. Thus, according to one embodiment, a magnetic material is comprised in the dry composition. Said magnetic material allows to stir and/or mix the composition during and/or after reconstitution by the aid of a magnet. Preferably, the magnetic material is incorporated into the composition before it is dried, preferably freeze-dried, to provide the dry composition. Thereby, the magnetic material becomes incorporated into the dry composition and can be used to assist the reconstitution process. According to a preferred embodiment, the magnetic material is a piece or a plurality of pieces of a magnetic foil. A further method that can be used is e.g. described in DE102007045474, herein incorporated by reference. According to one embodiment, the dry composition comprises a multiplicity of magnetic particles as well as at least one magnetic and/or magnetizable central element, which preferably is configured in the shape of a rod, dumbbell and/or ellipsoid. The magnetic and/or magnetizable central element is larger than the multiplicity of the magnetic particles. Preferably, these elements are incorporated into the composition before it is dried, preferably freeze-dried. The composition that was contacted for reconstitution with a liquid comprises a multiplicity of the first magnetic particles as well as at least one central element, which preferably is configured in the shape of a rod, dumbbell and/or ellipsoid. The magnetic particles are distributed in the liquid, and subsequently accumulate on the at least one central element. Stirring and/or mixing using the magnetic material is assisted by the use of at least one external magnet, e.g. a permanent magnet or electromagnet, which is configured to interact with the magnetic material. Stirring of the reconstituted composition may also be advantageous during the performance of the reaction(s) that is performed in the reaction chamber. E.g. if a reaction is performed that comprises a heating step such as in a PCR amplification, stirring, preferably at intervals, has the supporting effect that the heat is distributed quicker and more uniform. The magnetic material may comprise or consist of a material selected from the group paramagnetic materials, superparamagnetic materials, ferromagnetic materials, ferrimagnetic materials and mixtures thereof.

According to one embodiment, the dry composition comprises a solid support for clearing a sample as was described above. Preferably, carboxylated particles are comprised in the dry composition. According to one embodiment, a respective dry composition is contacted with the lysis mixture comprising the sample and a lysis solution as described above. This embodiment has the advantage that the dry composition provides a solid support that is suitable for clearing the reconstituted composition, by binding the contaminants such as precipitates, thereby forming complexes comprising the solid support and the contaminants. As described above, said complexes are optionally but preferably removed prior to performing the analysis method such as e.g. the amplification reaction.

The term "biomolecule" or "biomolecules" as used herein in particular refers to nucleic acids and polypeptides and preferably refers to nucleic acids. Other biomolecules include metabolites.

The term "nucleic acid" or "nucleic acids" as used herein, in particular refers to a polymer comprising ribonucleosides and/or deoxyribonucleosides that are covalently bonded, typically by phosphodiester linkages between subunits, but in some cases by phosphorothioates, methylphosphonates, and the like. Nucleic acids include, but are not limited to all types of DNA and/or RNA, e.g. gDNA; circular DNA; plasmid DNA; circulating DNA; PNA; LNA, cyclohexene nucleic acids; RNA/DNA hybrids; hnRNA; mRNA; non-coding RNA (ncRNA), including but not limited to rRNA, tRNA, miRNA (micro RNA), siRNA (small interfering RNA), snoRNA (small nucleolar RNA), snRNA (small nuclear RNA), pwi-interacting RNA (piRNA), repeat associated RNA (rasiRNA), as RNA and stRNA (small temporal RNA); fragmented nucleic acid; nucleic acid obtained from subcellular organelles such as mitochondria or chloroplasts; and nucleic acid obtained from pathogens, microorganisms, parasites, or DNA or RNA viruses that may be present in a biological sample, e.g. bacteria, viral or fungi nucleic acids; synthetic nucleic acids, extracellular nucleic acids. The term "extracellular nucleic acids" or "extracellular nucleic acid" as used herein, in particular refers to nucleic acids that are not contained in cells. Respective extracellular nucleic acids are also often referred to as cell-free nucleic acids. These terms are used as synonyms herein. The term "extracellular nucleic acids" refers e.g. to extracellular RNA as well as to extracellular DNA. Examples of typical extracellular nucleic acids that are found in the cell-free fraction (respectively portion) of biological samples such as body fluids such as e.g. blood plasma include but are not limited to mammalian extracellular nucleic acids such as e.g. extracellular tumor-associated or tumor-derived DNA and/or RNA, other extracellular disease-related DNA and/or RNA, epigenetically modified DNA, fetal DNA and/or RNA, small interfering RNA such as e.g. miRNA and siRNA, and non-mammalian extracellular nucleic acids such as e.g. viral nucleic acids, pathogen nucleic acids released into the extracellular nucleic acid population e.g. from prokaryotes (e.g. bacteria), viruses or fungi.

The term "polypeptide" as used herein refers to a molecule comprising a polymer of amino acids linked together by a peptide bond(s). Polypeptides include polypeptides of any length, including proteins (e.g. having more than 50 amino acids) and peptides (e.g. 2-49 amino acids). Polypeptides include proteins and/or peptides of any activity or bioactivity, including e.g. bioactive polypeptides such as enzymatic proteins or peptides, receptor proteins or peptides, transporter proteins or peptides, bactericidal and/or endotoxin-binding proteins, structural proteins or peptides, immune polypeptides, toxins, antibiotics, hormones, growth factors, vaccines and the like. Said polypeptide may be selected from the group consisting of peptide hormones, interleukins, tissue plasminogen activators, cytokines, immunoglobulins, in particular antibodies or antibody fragments or variants thereof. Also included are modified polypeptides such as e.g. glycosylated polypeptides.

The analytical method may be any chemical and/or biotechnological method that can be used to analyse a sample comprising a biomolecule of interest and in particular that can be used to analyse one or more biomolecules of interest comprised in the sample e.g. in order to amplify, identify, detect and/or quantify a biomolecule of interest. Preferably, the analytical method comprises a detection reaction which allows to detect the presence, absence and/or quantity of at least one biomolecule comprised in the lysed sample. Preferably, said method comprises the amplification of at least one target nucleic acid and the subsequent detection of the generated amplicon using e.g. labelled probes. Respective analytical methods are well-known in the prior art and are also commonly applied in the medical, diagnostic and/or prognostic field in order to analyse a biomolecule such as nucleic acids or a specific nucleic acid comprised in a sample. Hence the analytical method may comprise an analysis of the biomolecules comprised in the lysed sample to identify the presence, absence and/or severity of a disease state including but not being limited to a multitude of neoplastic diseases, in particular premalignancies and malignancies such as different forms of cancers. E.g. the lysed sample can be analysed in order to detect diagnostic and/or prognostic markers (e.g., fetal- or tumor-derived nucleic acids) in many fields of application, including but not limited to non-invasive prenatal genetic testing respectively screening, disease screening, oncology, cancer screening, early stage cancer screening, cancer therapy monitoring, genetic testing (genotyping), infectious disease testing, testing for pathogens, injury diagnostics, trauma diagnostics, transplantation medicine or many other diseases and, hence, are of diagnostic and/or prognostic relevance.

When the biomolecule of interest is a nucleic acid, the analysis can be performed using any nucleic acid analysis method including, but not limited to, identification technologies, amplification technologies, polymerase chain reaction (PCR), isothermal amplification, reverse transcription polymerase chain reaction (RT-PCR), quantitative real time polymerase chain reaction (qPCR), fluorescence detection, hybridization assays, DNA or RNA sequencing, restriction analysis, reverse transcription, NASBA, LAMP (loop mediated isothermal amplification), RPA (recombinase polymerase amplification), tHDA (helix dependent amplification), NEAR (nicking enzyme amplification reaction), TMA (transcription mediated amplification) and NASBA (nucleic acid sequence based amplification), allele specific polymerase chain reaction, polymerase cycling assembly (PCA), asymmetric polymerase chain reaction, linear after the exponential polymerase chain reaction (LATE-PCR), helicase-dependent amplification (HDA), hot-start polymerase chain reaction, intersequence-specific polymerase chain reaction (ISSR), inverse polymerase chain reaction, ligation mediated polymerase chain reaction, methylation specific polymerase chain reaction (MSP), multiplex polymerase chain reaction, nested polymerase chain reaction, solid phase polymerase chain reaction, detection technologies using labeled, preferably fluorescently labeled primers and/or probes, or any combination of the foregoing. Respective technologies are well-known to the skilled person and thus, do not need further description here. Preferably, the analytical method is a nucleic acid amplification method.

Other analytical methods include e.g. the detection of the presence, absence and/or quantity of a polypeptide, using e.g. labelled antibodies or other suitable labelled binding molecules that bind to the biomolecule of interest. Respective reagents can also be provided in form of a dry composition such as a freeze-dried composition.

The term "sample" is used herein in a broad sense and is intended to include sources that contain biomolecules, in particular nucleic acids and proteins. Exemplary samples include, but are not limited to, biological samples such as body fluids in general, whole blood, serum, plasma, red blood cells, white blood cells, buffy coat; swabs, including but not limited to buccal swabs, throat swabs, vaginal swabs, urethral swabs, cervical swabs, throat swabs, rectal swabs, lesion swabs, abcess swabs, nasopharyngeal swabs, anal swabs, urine, sputum, saliva, semen, lymphatic fluid, liquor, amniotic fluid, cerebrospinal fluid, peritoneal effusions, feces, pleural effusions, fluid from cysts, synovial fluid, vitreous humor; aqueous humor, bursa fluid, eye washes, eye aspirates, pulmonary lavage, lung aspirates, tissues, including but not limited to, liver, spleen, kidney, lung, intestine, brain, heart, muscle, pancreas and cell cultures, bacteria, microorganisms, viruses, plants, fungi including samples that derive from the foregoing or comprise the foregoing. Materials obtained from clinical or forensic settings or environmental samples such as soil that contain or are suspected to contain nucleic acids are also within the intended meaning of the term sample. Furthermore, the skilled artisan will appreciate that extracts, or materials or portions thereof obtained from any of the above exemplary samples are also within the scope of the term sample. Preferably, the sample is derived from a human, animal, plant, bacteria or fungi. Preferably, the sample is selected from the group consisting of cells, tissue, bacteria, virus and body fluids such as for example blood, blood products such as buffy coat, plasma and serum, urine, liquor, sputum, stool, CSF and sperm, epithelial swabs, vaginal swabs, cervix samples, biopsies, bone marrow samples and tissue samples, preferably organ tissue samples such as lung and liver. The sample may be stabilized. Certain samples such as blood samples are usually stabilised upon collection, e.g. by contacting them with a stabilizer such as an anticoagulant in case of blood and samples derived from blood.

The method according to the present invention does not require a step wherein the biomolecules of interest are isolated from the lysed sample e.g. by binding them to a solid phase and/or by precipitating them in order to purify them prior to contacting them with the dry composition. Rather, contaminants that could interfere with the intended analysis method such as e.g. precipitates are removed, respectively inactivated by clearing the lysed sample and/or the reconstituted composition that was reconstituted with the lysis mixture and treated to induce or complete the lysis of the comprised sample as is described above. This clearing step ensures that the analysis method can be efficiently performed even if a large amount of the lysed sample, which preferably is a cleared lysed sample, or the lysis mixture is directly used for reconstitution of the dry composition which comprises reagents for performing an analytical method. Hence, e.g. the analysis method may be carried out in immediate succession after lysis (and optional clearing) and reconstitution of the dry composition using the lysed sample, without the need for performing a purification of the biomolecules between lysis and reconstitution and without the need to reconstitute the dry composition before adding the lysed sample as the lysed sample is directly used for reconstitution. Similar considerations apply when reconstituting the dry composition with the lysis mixture first and then achieving or completing the lysis in the reconstituted composition e.g. by performing a heating step. Therefore, the method is particularly suitable for use in processing cartridges e.g. in LoC systems to reconstitute a dry composition that is comprised in the reaction chamber of a processing cartridge.

The term "solution" as used herein, e.g. as lysis solution in particular refers to a liquid composition, preferably an aqueous composition. It may be a homogenous mixture of only one phase but it is also within the scope of the present invention that a solution that is used according to the present invention comprises solid components such as e.g. precipitates.

According to a second aspect, the present invention pertains to the use of a lysed sample, preferably a cleared lysed sample, or a sample mixed with a lysis solution for reconstituting a dry composition comprising reagents for performing an analytical method by adding the lysed sample or the sample mixed with the lysis solution to the dry composition and mixing.

Details with respect to the reconstitution, the reagents comprised in the dry composition, the analytical method, the preparation of the lysed sample, the preparation of the reconstituted sample and the clearing step were described above in conjunction with the first aspect of the present invention. To avoid repetitions it is referred to the respective disclosure which also applies to the second aspect of the present invention. As discussed above, the present inventors have found that it is possible to reconstitute a dry composition comprising reagents for performing an analytical method such as e.g. an amplification method by adding at least an aliquot of a lysed sample, preferably of the cleared lysed sample, or a lysis mixture to the dry composition and mixing. As described above, it is not necessary to add further solutions such as a reconstitution solution. Furthermore, the biomolecules such as e.g. nucleic acids are not purified prior to reconstitution. Instead, preferably, reconstitution is exclusively achieved by the addition of the lysed sample, the cleared lysed sample or the lysis mixture. Thereby, a reconstituted composition is provided that is suitable for performing the analytical method. The reconstitution process is considerably simplified as the addition of a separate liquid for reconstitution is omitted. This makes the method particularly useful for use in LoC systems, as this method allows to use a much more simple cartridge design as will be described in the following. According to one embodiment, the use involves performing an analytical method using the reconstituted composition. Details with respect to the analytical method that can be performed and preferred embodiments were described above in conjunction with the first aspect of the present invention. To avoid repetitions it is referred to the respective disclosure which also applies to the second aspect of the present invention.

According to a third, independent, aspect, the present invention pertains to a method for clearing a sample from precipitates, wherein the sample is contacted prior, during or after lysis with at least one solid support which binds to precipitates originating from the lysed sample, thereby forming a complex with the precipitates, and wherein said complex is optionally but preferably separated from the remaining sample. This method is particularly suitable for clearing a lysed sample as described above.

The present inventors have developed methods that are particularly suitable for providing a cleared lysed sample that comprises due to the clearing process a reduced amount of precipitates. The efficient removal of precipitates improves the performance of the subsequent analytical method, in particular when intending to perform an amplification reaction, as the respective methods can be inhibited by precipitates that are carried over from the lysed sample into the analytical reaction. Therefore, a respectively cleared lysate can be directly used in an analytical method such as e.g. an amplification reaction. Furthermore, the developed lysate clearing method is particularly suitable for providing a cleared lysate that is suitable for reconstituting a dry composition comprising reagents for performing the analytical method as the amount of inhibiting contaminants such as in particular precipitates is reduced. Furthermore, as discussed above, a respective method is also suitable for providing a cleared reconstituted composition, wherein a lysis mixture is added for reconstitution. In a respective lysis mixture, lysis is not completed yet. As described above, lysis can be achieved and/or completed by heating the reconstituted composition to a temperature of at least 90° C., preferably at least 95° C. Details were described above. Details with respect to the clearing method, suitable and preferred solid supports and surfaces for binding precipitates, the complex(es), as well as details with respect to the lysis procedure for providing a lysed sample and suitable and preferred lysis solutions were described above in conjunction with the first aspect of the present invention. To avoid repetitions it is referred to the respective disclosure which also applies to the third aspect of the present invention.

According to a fourth independent aspect, a method is provided for elevating the pH value of an acidic sample, said method comprising the addition of a molecular sieve to the sample to elevate the pH value of the acidic sample. Preferably, said method has one or more of the following characteristics
   a) the pH value of the acidic sample is ≤6.5, ≤6.0, ≤5.5≤5≤4.5 or lies in a range selected from 3 to 6.5 and 3.5 to 6;
   b) the addition of the molecular sieve results in that the pH is elevated to a pH range that is selected from 7.5 to 9, 8 to 9 and 8 to 8.5;
   c) the added molecular sieve is zeolite;
   d) the molecular sieve is added prior, during or after the lysis of the sample;
   e) the lysed sample, that has been contacted with the molecular sieve, is subsequently used in an amplification reaction; and/or
   f) no nucleic acid purification or isolation is performed upon contact with the molecular sieve.

Details of the method will be described in the following. Where appropriate, we refer to the above disclosure.

Examples of molecular sieves are described above. For elevating the pH value, a molecular sieve must be use which results in that the pH value is elevated. Preferably, the molecular sieve is capable of raising the pH value of an acidic sample by at least 1 pH unit, more preferred by at least 2 pH units. The acidic sample may have a pH value≤6.5, ≤6.0≤5.5, ≤5≤4.5. Preferably, it has a pH value that lies in a range between 3 to 6.5, preferably 3.5 to 6. A typical acidic sample is a vaginal sample, e.g. a vaginal or a cervical swab. According to one embodiment, addition of the molecular sieve results in that the pH is elevated to a pH range that lies between 7.5 to 9, preferably 8 to 9, more preferred 8 to 8.5. As is shown by the examples, the addition of the pH elevating molecular sieve has the surprising effect that the pH value of an acidic sample can be set up to a predefined pH range, even if the initial pH value of the sample varies. The pH elevating molecular sieve that is used according to this aspect of the invention performed even better than the addition of a chemical buffer. Preferably, zeolites are used as molecular sieve. As is shown by the examples, zeolites are very efficient in elevating the pH value of acidic samples. Preferably, they are added in an amount of 2-50 mg/ml, preferably 5 to 30 mg/ml or 5 to 20 mg/ml sample mixed with a lysis composition such as a lysis solution. Preferably, the pH elevating molecular sieve is added prior, during or after the lysis of the sample. Preferably, it is present during lysis. Thereby, acidic samples can be in particular advantageously preferred for use of the provided lysate in a subsequent amplification reaction. Thereby, an individual set up of the pH value of the lysate prior to performing the amplification reaction becomes obsolete, respectively is the performance of a downstream method that is influenced by the pH value as is an amplification reaction such as a PCR. Furthermore, adding a molecular sieve prior, during or after lysis has the effect that contaminants, such as in particular precipitates, can be efficiently removed. The molecular sieve, which preferably is a zeolite, is not used for isolating nucleic acids but is used in order to prepare the sample for a subsequent analysis method, in particular for an amplification method such as PCR. Therefore, the molecular sieve is preferably contacted with the acidic sample under conditions under which no substantial binding of nucleic acids to the molecular sieve occurs. Hence, preferably, at least 80% of the comprised nucleic acids, at least 90%, at least 95% or at least 98% of the target nucleic acid do not bind to the molecular sieve under the used conditions. The target nucleic acid can be DNA or RNA, or may refer to both. As discussed above, preferably, the molecular sieve is added during lysis.

According to a fifth aspect, a processing cartridge is provided which is suitable for use in a method for analysing a sample comprising biomolecules according to the first aspect of the present invention. Said processing cartridge comprises a cartridge body and at least one reaction chamber which comprises a dry composition comprising reagents for performing an analytical method, wherein the cartridge body comprises a sample intake opening, at least one sample outlet and a fluid passageway that connects the sample intake opening and the sample outlet, wherein the sample outlet opens into the reaction chamber, wherein the cartridge is designed such that reconstitution of the dry composition comprised in the reaction chamber is achieved by a sample that enters the cartridge through the sample intake opening.

The term "fluid" as used herein is used as generic term which encompasses gases and liquids.

The sample fluid passageway may comprise at least one of channels and/or cavities and preferably is at least partially formed into the surface of the cartridge body. The fluid passageway ensures a predefined flow pathway of the sample after the sample has entered through the sample intake opening, thereby ensuring that it reaches the at least one reaction chamber. The reaction chamber can be integrated into to cartridge body or can be provided as separate element that can be assembled to the cartridge body. Preferably, the one or more reaction chambers are provided as separate device(s) that is assembled to the cartridge body. In this embodiment wherein the reaction chamber is provided by a separate device, the cartridge body comprises means, preferably a connection projection, for connecting at least one reaction chamber to the cartridge body. Upon connection, a fluid communication between the sample outlet and the reaction chamber is established so that the sample can enter the reaction chamber. The cartridge body may also comprise a plurality of reaction chambers. Providing more than one reaction chamber in the processing cartridge has the advantage that more than one reaction and hence more than one analysis can be carried out with the same sample. This allows, e.g., to detect the presence or absence of different targets (e.g. disease markers or pathogens) in parallel using the same cartridge. Thus, such a design is particularly suitable for performing multiplex assays. Several assays may, however, also be performed in one reaction chamber, e.g. in one amplification reaction using different primers and/or probes, as is well known in the prior art.

If a plurality of reaction chambers are used which are provided as separate device(s), the cartridge body comprises a plurality of means, preferably connection projections, for connecting the reaction chambers to the cartridge body. Several reaction chambers can be provided as one device that can be assembled fluid-tightly to the cartridge body. This allows to perform different reactions in the respective chambers, e.g. to detect different pathogens or disease markers in parallel. The different reaction chambers can be provided with dry compositions comprising different reagents, e.g. comprising different primers and/or probes when performing an amplification reaction. Incorporating several reaction chambers into one device eases the handling and hence the assembly of the processing cartridge what saves costs.

Furthermore, the cartridge body comprises means, preferably a connection projection, for connecting a sample vessel to the cartridge body. Suitable connections for connecting the reaction chamber(s) and the sample vessel to the cartridge are well-known in the prior art and thus, do not need any detailed description. The connection may be established based on the principles of form closure, force closure and/or friction locking. Preferred embodiments are shown in the examples.

When the processing cartridge is in use, the sample must enter the cartridge through the sample intake opening. Entry may be assisted by injection or any other suitable means. E.g. the sample vessel may comprise a piston, which allows to transfer the sample from the sample vessel into the sample passageway.

According to a preferred embodiment, the cartridge body comprises a fluid intake opening B which is through a fluid passageway B in fluid communication with the sample vessel if said vessel is assembled to the cartridge body and which allows the introduction of air into the sample vessel. For this purpose, the cartridge body may comprise a fluid outlet B through which the air can enter into the vessel if said vessel is assembled to the cartridge body. A pressure generating apparatus such as a pump may be connected to the fluid intake opening B, thereby allowing to pump air into the sample vessel. If a pump is used, the pressure preferably lies in a range of 100 to 1000 mbar, preferably 150 to 500 mbar, more preferred 200 to 250 mbar. The pressure generated by the pump has the effect that the sample is pressed into the cartridge through the sample intake opening and hence reaches the reaction chamber being guided by the sample fluid passageway. The sample enters the reaction chamber through the sample outlet.

According to one embodiment, means are provided for controlling the amount of liquid that can enter the reaction chamber for reconstitution of the dry composition. According to one embodiment, the at least one reaction chamber and/or the means for connecting the reaction chamber to the cartridge body comprise at least one fluid opening A through which a fluid, in particular air or similar fluids, can exit the reaction chamber. Thus, according to one embodiment, the reaction chamber and/or the connection projection for connecting the reaction chamber to the cartridge comprises a respective fluid opening A. Thereby, air can escape from the reaction chamber when the sample is introduced into the cartridge body and enters the reaction chamber. The air is basically displaced by the sample. According to one embodiment, the fluid opening A through which a fluid can exit the reaction chamber comprises a barrier, wherein said barrier substantially prevents the passage of liquid. The barrier allows the passage of air at least before said barrier comes into contact with a liquid. However, it substantially prevents the passage of a liquid. Thereby, the amount of sample that can enter the reaction chamber is controlled so that the reaction chamber is filled with the desired amount of sample that is necessary for proper reconstitution of the dry composition that is comprised in the reaction chamber. Thus, said barrier can be advantageously used for metering as only the desired amount of sample can enter the reaction chamber due to the counter pressure that is generated by the membrane that prevents the passage of the sample. Furthermore, it prevents that the sample, including the reagents comprised in the reaction chamber is accidently flushed out of the reaction chamber. Said barrier, which preferably is a membrane positioned such that only a predetermined amount of sample can enter into the reaction chamber. At least a portion of said barrier, which preferably is a membrane, is in contact with the sample when the predetermined amount of sample that is required for reconstitution of the dry composition has entered the reaction chamber, then preferably blocking the further entry of sample. The membrane preferably is a hydrophobic membrane. Preferably it is porous. Preferably, a membrane is used having a pore size that lies in a range of 0.05 µm to 0.5 µm, preferably 0.1 µm to 3 µm, more preferred of 1.5 µm to 2.5 µm, most preferred of approx. 2 µm. The membrane may comprise a polymer. According to one embodiment, the membrane comprises a support such as a non-woven nylon support. According to one embodiment, the membrane is an acrylic copolymer membrane cast on a non-woven nylon support or a membrane having the same properties with respect to the passage of air and liquids. Said membrane which works as a barrier for the sample makes more complicated devices such as e.g. dispensing devices for introducing a predetermined amount of liquid into the reaction chamber obsolete. A sufficiently exact metering can be achieved with said barrier which prevents the entry of further sample once the reaction chamber is filled up with sample. Thus, e.g. a pump comprised in the processing device may continuously pump air into the reaction vessel until the membrane creates a counterpressure that prevents that more sample can enter from the vessel into the cartridge. According to one embodiment, said fluid opening A that may be used to vent the reaction chamber and to control the input of sample into the cartridge is located such, that the air exits directly the cartridge. It may according to one embodiment be comprised in the reaction chamber.

However, said fluid opening A may also be comprised inside the cartridge. E.g. as is shown by the examples, it may be located within or can be provided by the means for connecting the reaction chamber to the cartridge. Preferably, said fluid opening A that is used for venting the reaction chamber opens into further fluid passageway A that is connected to a further fluid outlet A. Providing such a further fluid passageway A that receives the air from the one or more reaction chambers has specific advantages, in particular if a the analytical method involves one or more heating steps within the reaction chamber, as is e.g. the case with many amplification methods, as the further fluid passageway A can be blocked, thereby preventing or at least reducing the risk that the liquids evaporate during the heating step. This can improve the accuracy of the performed analytical method involving a heating step. According to one embodiment, means are provided that allow to close the fluid passageway that connects the sample intake opening and the sample outlet and/or the fluid passageway A that connects the fluid opening A through which a fluid, in particular air, can exit the reaction chamber with the fluid outlet A. Said means may form a barrier within said fluid passageway(s), which in conjunction with a lid that is closing said fluid passageway(s) allow to close or open said fluid passageway(s) thereby function as a simple valve. When pressure is applied to the lid, the valve is closed, if the pressure is removed, the valve is opened. Further details of this embodiment will be described below in conjunction with the cartridge body.

Furthermore, providing respective barriers in the sample passageway has the advantage that the transfer of the sample from the sample vessel into the cartridge can be performed in a remarkably simple fashion. Herein, the sample vessel comprises the sample mixed with the lysis solution. Said mixture is heated to induce the lysis of the sample as described above. A pressure is applied to the lid, thereby closing the valves. The heating step results in that an overpressure is created in the sample vessel. If the valves are opened by removing the pressure from the lid, the sample flushes the cartridge due to the overpressure that is generated in the sample vessel. The sample thereby enters the reaction chamber through the provided sample passageway. A controlled filling of the reaction chamber is ensured by providing a fluid opening A comprising a barrier for the sample as described above. This embodiment is advantageous, because no separate pump or the like are needed in order to achieve the transfer of the sample from the connected sample vessel into the cartridge. Preferably, the transferred sample is a lysed sample, more preferred a cleared lysed sample as described above, or a lysis mixture as described above.

The cartridge according to the present invention has a remarkably simple design as it does not need any reservoirs for liquids or solutions for sample processing or reconstitution of the dry composition comprised in the reaction chamber. Furthermore, the cartridge does not need one or more separate waste reservoirs for storing used sample materials and/or reagents. As the whole processing cartridge may be operated (only) by the sample that enters the cartridge, which preferably is a lysed sample or a lysis mixture as described above, there are no excess liquids or solutions that must be handled or disposed. Furthermore, as no liquids are provided on the cartridge e.g. in order to process the sample or to reconstitute the dry composition, the risk is reduced that said liquids leach. Such leaching is a considerable problem, because a partial reconstitution of the dry composition may irreversibly compromise the reagents comprised therein. That no liquids besides the sample must be provided is a remarkable advantage over prior art cartridges which also improves the production and reduces costs.

In a preferred embodiment, the cartridge body comprises a tube with a first end opening and a second end opening, wherein the first end opening of the tube is aligned with the sample intake opening. The tube thus prolongates the sample passageway. A fluid coming from the sample vessel will first enter into the second end opening of the tube and flow through the tube to leave the tube at the first end opening and enter the sample passageway through the sample intake opening aligned with the first end opening of the tube. Said tube can for example be used to reach into the sample vessel when assembled to the cartridge body and to allow a fluid such as a sample comprised in the vessel to flow into the sample passageway if overpressure is created in the sample vessel e.g. by means of a fluid entering the sample vessel through the fluid outlet B or by the overpressure that is generated when the lysis mixture is heated and the valve comprised in the sample passageway is closed as is described above.

Preferably, the sample outlet and the fluid opening A are provided by tubes that are arranged in the side wall of either the reaction chamber, in particular if the reaction chamber is provided as integrated element, or the reaction chamber connection projection. Constructing the sample outlet in a tube has the advantage that the sample enters the reaction chamber in a controlled fashion similar as if it was pipetteted to the side wall of a reaction vessel. Preferably, the tube is comprised in a convexity of the side wall. Thereby, an uncontrolled flushing of the reaction chamber can be prevented. The fluid opening B that is in fluid communication with the reaction chamber is also preferably comprised in a convexity of a side wall, preferably arranged opposing to the sample outlet. Further details and advantages of said arrangement are described below and in the figures.

According to one embodiment, the cartridge body is assembled to a sample vessel comprising a sample vessel opening that is arranged in such a manner that the sample vessel opening is in fluid connection with the sample intake opening so that a fluid such as the sample can enter from the vessel into the sample intake opening. Said sample vessel contains a sample to be analysed mixed with a lysis composition. The lysis composition may have one or more of the characteristics described above in conjunction with the first aspect of the present invention. Preferably, a lysis solution is used which comprises or consists of the following components (a) at least one nonionic surfactant or mixture of non-ionic detergents,
(b) at least one polymer which prevents or reduces the inhibition of the subsequent analytical method preferably by unspecific complexing of potential inhibitors;
(c) optionally a proteolytic enzyme,
(d) optionally a chelating agent for divalent cations and
(e) optionally a buffer substance.

Suitable details are also described above, it is referred to the respective disclosure. It may also comprise a magnetic stirring bar to assist mixing of the sample in the lysis solution. Preferably, it comprises a solid support for clearing the lysate, more preferably it comprises carboxylated magnetic particles. Thereby, precipitates can be efficiently removed and a cleared lysate is provided that can pass the sample intake opening as "sample". Respectively pretreated samples which may have been lysed and/or from which contaminants or other sample components were removed also referred to as "sample" in conjunction with the cartridge for the ease of simplicity. Further details of the lysis solution and the solid support(s) that can be used for clearing the lysate were described above, it is referred to the respective disclosure.

Preferably, the processing cartridge has a cartridge body as described below in conjunction with the sixth aspect according to the present invention.

According to a sixth aspect, a specific cartridge body is provided. The cartridge body according to the invention can be used to provide a fluid connection from a sample vessel that contains a fluid such as a sample to at least one reaction chamber. The sample vessel and the one or more reaction chambers—if provided as separate element—can be assembled to the cartridge body. Such a cartridge body can be advantageously used for putting into practise the method according to the first aspect of the present invention. Subsequently, we will explain the design of said cartridge body, the elements and their function as well as their interaction with the sample vessel and the reaction chamber that can be assembled to said cartridge body and/or the analytical method that can be performed by using a respective cartridge body. As described, the cartridge body is suitable for providing a fluid connection from a sample vessel that contains a fluid and can be assembled to the cartridge body, to at least one reaction chamber that can be assembled to the cartridge body or which is provided as integral part of the cartridge body. Said cartridge body comprises a sample intake opening and a sample outlet, a sample passageway that connects the sample intake opening and the sample outlet, a sample vessel connection projection for connecting the sample vessel, wherein upon assembly of the sample vessel to said connection projection the sample intake opening is in fluid communication with the sample vessel, at least one reaction chamber connection projection for connecting a reaction chamber wherein upon assembly of the reaction chamber to said connection projection the sample outlet is in fluid communication with the reaction chamber and/or comprising at least one reaction chamber that is provided as integral part of the cartridge body wherein at least one fluid opening A is provided in the reaction chamber connection projection and/or in the reaction chamber and wherein said fluid opening A comprises a barrier, wherein said barrier allows the passage of air at least before said barrier comes into contact with a liquid but wherein said barrier substantially prevents the passage of liquid.

As discussed above and below, the filling of the at least one reaction chamber by the sample that enters the cartridge body through the sample intake opening and arrives through the provided fluid passageway at the at least one reaction chamber is controlled by a barrier for liquids that is comprised in the fluid opening A. Said barrier preferably is a porous hydrophobic membrane, which allows the passage of air (at least before wetting) but which substantially does not allow the passage of sample. As soon as the sample reaches the hydrophobic membrane, it can not pass by said membrane and the filling of the reaction chamber automatically stops, thereby ensuring that the dry composition is reconstituted with a pre-determined adequate amount of sample, which preferably is a cleared lysed sample as described above. Said cartridge body can be advantageously used as cartridge body in the processing cartridge according to the fifth aspect of the present invention. The sample outlet as well as the fluid opening A are in fluid communication with the at least one reaction chamber which may be provided as integral part of the cartridge body or, preferably, is provided as separate element.

Subsequently, we will in particular describe the details of particularly preferred embodiments. Further details and other embodiments are also described in the figures, the claims and subsequently.

The cartridge body may have a fluid intake opening B and a fluid outlet B, whereby a fluid passageway B connects the fluid intake opening B and the fluid outlet B. The fluid intake opening B can for example be used to receive a fluid, preferably air, that flows through the fluid passageway B and leaves the cartridge body at the fluid outlet B, for example to enter a sample vessel. E.g. as described above the fluid intake opening B can be connected to a pressure generating apparatus, which pumps air through first intake opening. The cartridge body further comprises a sample intake opening and a sample outlet, whereby a sample passageway connects the sample intake opening and the sample outlet. The sample intake opening can for example be used to take up a liquified product such as a sample from the sample vessel that flows through the sample passageway and leaves it at the sample outlet, for example to enter a reaction chamber.

The reaction chamber and/or the reaction chamber connection projection for connecting the reaction chamber to the cartridge body comprises at least one fluid opening through which a fluid, namely air, can exit the reaction chamber. Thus, according to one embodiment, the reaction chamber and/or the reaction chamber connection projection comprise a fluid opening A. Thereby, air can escape from the sample passageway and the reaction chamber when the sample is introduced into the cartridge body and enters the reaction chamber. The air is displaced by the sample. According to a preferred embodiment, said fluid opening A is comprises a barrier, preferably a membrane, which allows air to pass but not the sample. Details are described above. Thereby, the amount of sample that can enter the reaction chamber is controlled so that the reaction chamber is filled with the desired amount of sample that is necessary for reconstitution of the dry composition that is comprised in the reaction chamber. Thus, said barrier can be used for metering as only the desired amount of sample is pumped into the reaction chamber due to the counter pressure that is created by the membrane that prevents the passage of the sample. A sufficiently exact metering can be achieved with said barrier comprised in the fluid opening A that is comprised in the reaction chamber and/or the second projection comprising the fluid opening A. Details were described above.

In a preferred embodiment the cartridge body comprises a fluid opening A, a fluid outlet A and a fluid passageway A that connects the fluid opening A and the fluid outlet A. The fluid opening A can take up a fluid, namely a gas such as air, that leaves the reaction chamber and which flows through the fluid passageway A to leave the cartridge body at the fluid outlet A. Providing such a fluid outlet A and fluid passageway A has specific advantages if the analytical method involves a heating step in the reaction chamber, as is e.g. the case with many amplification methods. The fluid passageway A can be blocked using small bars which function together with the lid as a valve as was described above and as will be described in further detail below. Blockade of said fluid passageway A prevents the evaporation of liquids during the heating step. This can improve the accuracy of the performed analytical method involving a heating step.

The cartridge body has a sample vessel connection projection for connecting the sample vessel. Upon assembly of the sample vessel to the sample vessel connection projection, the fluid outlet B and the sample intake opening are in fluid communication with the vessel. Thus, a fluid such as air can enter into the sample vessel through the fluid outlet B and a fluid such as the sample can enter into the sample passageway through the sample intake opening. Preferably, an overpressure is introduced via the fluid outlet B into the vessel in order to induce the movement of the sample as was described above and will be described in further detail below. However, as described above, also other methods are feasible to transfer the sample from the vessel into the cartridge.

Said first projection may be made up of one or more side walls. A chamber may be formed by said one or more side walls and a base wall. Said chamber may have an opening opposite the base wall. Upon connection of the sample vessel to said connection projection, the fluid outlet B and the sample intake opening are arranged in the base wall or one of the side walls of said first projection. This arrangement of the fluid outlet B and the sample intake opening allows for a first fluid, preferably air to be blown into the chamber and a sample vessel that is connected to the sample vessel connection projection. This air blown into the first chamber can be used to force a further liquid, such as the sample comprised in the sample vessel, to leave the sample vessel connected to the sample vessel connection projection due to the overpressure created by the fluid leaving the fluid outlet B and entering the chamber and the sample vessel. The arrangement of the sample intake opening allows a sample to leave the sample vessel and to flow along the sample passageway to the sample outlet.

The connection of the sample vessel to the cartridge body can be achieved by any suitable means that allow a tight connection between the sample vessel and the cartridge body. Examples include but are not limited to a thread connection, a clipping mechanism or a bayonet clipping. According to one embodiment the one or more side walls of the sample vessel connection projection are adapted to fit into an opening of the sample vessel to achieve a connection. Alternatively, the one or more side walls may be adapted for a connection projection to be fit into the first chamber that may be formed by the side walls and the base wall.

The cartridge body according to the invention further has according to a preferred embodiment at least one reaction chamber connection projection for connecting a reaction chamber. Upon assembly of the reaction chamber to the reaction chamber connection projection the sample outlet is in fluid communication with the reaction chamber. Thereby, a sample can enter through the sample outlet into the reaction chamber. The reaction chamber connection projection may be made up of one or more side walls and a base wall. The connection between the reaction chamber and the reaction chamber connection projection can be again achieved by any suitable means that ensure a tight connection between the cartridge body and the reaction chamber. E.g. the one or more side walls of the second projection connection can be adapted to fit into an opening of the reaction chamber or the side walls may be adapted for a connection projection of the reaction chamber to be fit into a first chamber of the second projection connection that can be e.g. formed by the one or more side walls and a base wall and that has an opening opposite the base wall. The reaction chamber may be connected to the side walls or the base wall of the reaction chamber connection projection.

The sample outlet and optionally the fluid opening A may be arranged in the base wall or at least one of the side walls of the reaction chamber connection projection. As discussed above, it is also conceivable to provide the fluid opening A in the reaction chamber. However, it is preferred to provide them in the cartridge body, in particular in the reaction chamber connection projection as described herein. This arrangement of the sample outlet and the fluid opening A allows the sample to enter into the reaction chamber through the sample outlet. Preferably, the sample outlet and the fluid opening A are provided by tubes that are arranged in the side wall of the reaction chamber connection projection. The tube may have any shape and may also comprise e.g. turnings. Constructing the sample outlet in a tube has the advantage that the sample enters the reaction chamber in a controlled fashion similar as if it was pipetteted to the side wall of a reaction vessel. Thereby, an uncontrolled flushing of the reaction chamber can be prevented. The fluid opening A that is in fluid communication with the reaction chamber allows the air in the reaction chamber to leave the reaction chamber forced by the pressure that is created within the reaction chamber by the sample coming from the sample vessel, passing through the sample passageway and entering the reaction chamber via the sample outlet. Preferably, the fluid opening A is provided by a tube that is arranged in the base wall of the reaction chamber connection projection. As described above and below, said fluid opening A is preferably closed by a membrane, preferably a hydrophobic membrane in order to control the entry of further sample into the cartridge, respectively the reaction chamber, if the reaction chamber is filled with the predetermined and hence desired amount of sample that is necessary for reconstitution. The membrane that is sealing the fluid opening A allows the air at least to escape until the sample wets the membrane. Usually, the passage of air is also hampered or even prevented once the membrane was wetted or air may only pass if a high pressure is generated as it might occur when performing a heating reaction within the reaction chamber. Preferably, said membrane is located at the upper end of a tube that is comprised in the side wall of the second projection connection. Providing the fluid opening A in form of a tube and placing the membrane within or preferably, at the upper end of said tube has the advantage that a premature closure of the reaction chamber can be prevented. Even if the sample quickly flushes the reaction chamber due to the applied pressure, the reaction chamber must be filled first before the sample ascents the tube. Thereby, it is ensured that the reaction chamber is filled with the desired amount of sample before the sample contacts and hence wets the membrane, thereby locking the reaction chamber. Thereby, an unwanted bypass of the sample outlet and the fluid opening A that could result in that the reaction chamber is not filled with the predetermined amount of liquid that is necessary for the correct reconstitution of the dry composition is prevented.

The cartridge body according to the invention is described to have fluid intake openings and fluid outlets. Preferably, a fluid intake opening (or an opening in general) and a fluid outlet is understood to be or comprise a hole in a body. A fluid intake opening may form a hole through which a fluid flows into a fluid passageway and a fluid outlet may form a hole through which the fluid flows from the fluid passageway. It may be provided in form of a tube. At the junction between two fluid passages, the same hole may provide both functions. Neither the fluid intake opening, openings in general, nor the fluid outlets are limited in their shape. Preferably, the holes are circular or elliptical. The holes can however also be square, triangular or of any other geometric shape. The holes can be open holes. The holes may also comprise or may be covered by a membrane or filter. Also in this case they are still understood as hole and hence as opening or outlet, as long as the fluid of interest can flow through the membrane or filter, even if a fluid of another type can not pass through said membrane or filter.

The cartridge body is claimed to have fluid passageways. As fluid passageway, they allow the flow of a fluid such as a liquid (in particular the sample) or gas, in particular air. They may have any form or size. Passageways may comprise one or more channels and/or cavities. They may be open at their top and e.g. can be closed using a lid such as e.g. a plastic film. They may comprise bars to provide in conjunction with the lid a simple valve as described above. Passageways include also conduits for fluids that lead through a body. Passageways need not to be of symmetrical shape in cross section. The passageways according to the present invention may lead the flow of a fluid into a predefined direction. E.g. the sample passageway leads the flow of the sample into the one or more reaction chambers, if the sample is introduced into the sample passageway applying pressure. The fluid passageway A leads air to the fluid outlet A, thereby allowing air to exit the passageway system and the reaction chamber when the sample is introduced.

The sample vessel connection projection of the cartridge body may be made up of one or more side walls that can in a preferred embodiment encompass a first chamber that is further formed by a base wall and that has an opening opposite the base wall. In a preferred embodiment, the side walls of the sample vessel connection projection form a tubular body, which means nothing more than that the side walls can be made up of one side wall that is closed at its facing ends. Therefore, the term "side walls" as used herein also refers to and encompasses embodiments, wherein only one respective side wall is used. The sample vessel connection projection does however not need to be of tubular shape. The sample vessel connection projection can, for example, have a rectangular or quadratic cross sections, being made up of two or more, e.g. four side walls that are connected to each other at their respective ends. The sample vessel connection projection can also be of triangular cross section or any other suitable cross section. The first chamber formed by the one or more side walls is further formed by a base wall. Preferably the sample vessel connection projection is of a cup-shape. The base wall of the sample vessel connection projection can be a flat surface. Like in a cup, the base wall can, however, also be of rounded shape. According to one embodiment, the chamber has an opening opposite the base wall. This opening can be as large as the area left free by the side walls. The opening can, however, also be formed into a top wall that further boarders the first chamber and is arranged opposite the base wall.

According to one embodiment, the sample vessel connection projection is adapted to fit into an opening of the sample vessel or for a connection projection of a sample vessel to be fit into the first chamber of the sample vessel connection projection. The connection projection is preferably adapted for the sample vessel to be connected to the side walls of the connection projection and thereby for allowing the sample vessel to be tightly connected to the cartridge body.

Preferably, the fluid outlet B and the sample intake opening are arranged in the base wall or in one of the side walls of the sample vessel connection projection. The fluid outlet B and the sample intake opening do not need to be arranged at the same element. For example, the fluid outlet B can be arranged in the base wall and the sample intake opening can be arranged in one of the side walls of the first projection. The fluid outlet B and the sample intake opening are preferably arranged to open into the first chamber. However, it is also feasible that the fluid outlet B and the sample intake opening are arranged in the side walls and open on the top surface of the side walls.

The reaction chamber connection projection of the cartridge body may also be made up of one or more side walls that can in a preferred embodiment encompass a second chamber that is further formed by a base wall. It may comprise an opening opposite the base wall. In a preferred embodiment, the side walls of the reaction chamber connection projection form a tubular body, which means that the side walls can be made up of one side wall that is closed at its facing ends. The reaction chamber connection projection does however not need to be of tubular shape. The reaction chamber connection projection can, for example have a rectangular or quadratic cross sections, being made up of four side walls that are connected to each other at the respective ends. The reaction chamber connection projection can also be of triangular cross section or any other suitable cross section. The second chamber formed by the side walls is further formed by a base wall. Preferably the reaction chamber connection projection is of a cup-shape. The base wall of the reaction chamber connection projection can be a flat surface. Like in a cup, the base wall can, however, also be of rounded shape. The chamber has an opening opposite the base wall. This opening can be as large as the area left free by the side walls. The opening can, however, also be formed into a top wall that further boarders the first chamber and is arranged opposite the base wall.

The reaction chamber connection projection is according to one embodiment adapted to fit into an opening of the reaction chamber or for a connection projection of a reaction chamber to be fit into the chamber of the reaction chamber connection projection. The connection projection is adapted for the reaction chamber to be connected to the side walls of the connection projection and thereby for allowing the sample vessel to be connected to the cartridge body.

According to one embodiment, the sample outlet and the fluid opening A are arranged in the base wall or in one of the side walls of the reaction chamber connection projection. The sample outlet and the fluid opening A do not need to be arranged at the same element. For example the sample outlet can be arranged in the base wall and the fluid opening A can be arranged in one of the side walls. The sample outlet and the fluid opening A are preferably arranged to open into the chamber of the reaction chamber connection projection. However, it is also feasible that the sample outlet and the fluid opening A are arranged in the side walls and open on the top surface of the side walls. Furthermore, as described above, the fluid opening A may also be comprised in the reaction chamber, preferably at the top, even through it is preferred to provide it in the cartridge body. Preferably, also herein the sample outlet and the fluid opening A are provided as tubes in the convexity of a side wall for the reasons described above.

In a preferred embodiment, the cartridge body comprises a tube with a first end opening and a second end opening, wherein the first end opening of the tube is aligned with the sample intake opening. The tube thus prolongates the sample passageway. A fluid coming from the sample vessel will first enter into the second end opening of the tube and flow through the tube to leave the tube at the first end opening and enter the sample passageway through the sample intake opening aligned with the first end opening of the tube. Said tube can for example be used to reach into the sample vessel when assembled to the cartridge body and to allow a fluid such as a sample comprised in the vessel to flow into the sample passageway if overpressure is created in the sample vessel by means of a fluid entering the sample vessel through the fluid outlet B. Overpressure can be generated by a pressure generating devise such as a pump that can be connected to the fluid intake opening B.

The tube can be of any shape and material and can for example be flexible. However, according to a preferred embodiment, the tube is a rigid, longitudinal tube. This allows for the sample vessel to be more easily attached to the cartridge body and for the tube to enter into an opening of the sample vessel more easily, if the sample vessel is attached to the cartridge body. Preferably, the tube is made of the same material as the cartridge body. Preferably, it forms an integral part of said cartridge body.

In a preferred embodiment, the one or more side walls of the sample vessel connection projection and/or the one or more side walls of the reaction chamber connection projection form a tubular body. Forming the sample vessel connection projection and/or the reaction chamber connection projection in form of a tubular body facilitates the tight connection of the sample vessel to the sample vessel connection projection and facilitates the tight connection of the reaction chamber to the reaction chamber connection projection.

The assembly between the sample vessel and the reaction chamber to the connection projections can be achieved by any suitable means. The connection may be based on the principles of form closure, force closure and/or friction locking. Depending on the chosen means for connection, the first and reaction chamber connection projections comprise suitable elements to achieve such a connection. In a preferred embodiment the one or more side walls of the sample vessel connection projection form a tubular body and the tubular body has an external thread, thereby allowing to achieve the connection between a matching sample vessel and the cartridge body by screwing. Preferably, the one or more side walls of the reaction chamber connection projection also form a tubular body comprising means for assembling the reaction chamber. As it is preferred to assemble more than one reaction chamber to one cartridge body, it is preferred to use a mechanism that allows to assemble a set comprising multiple reaction chambers at once.

The fluid passageways can be at least partially formed by at least one channel and/or cavity formed in the surface of the base plate of the cartridge body. Providing the cartridge body with a base plate allows the cartridge body to be handled more easily. Providing the fluid passageways at least partially in form of at least one channel and/or cavity formed into the surface of the base plate allows for an easy manufacturing method to create the fluid passageways, as the channels and/or cavities can be easily formed into the surface of the base plate, for example by injection moulding the base plate or by cutting the channels or cavities into a base plate already provided.

A passageway in particular refers to a space through which the respective fluid may flow and that guides the flow of the fluid. The respective passageway thus usually starts at the respective intake opening and ends at the respective fluid outlet. Preferably, a passageway is provided by at least one channel and/or cavity. This also includes passageways, wherein the fluid communication is achieved by a system of and hence a plurality of channels and/or cavities. In order to reach to the respective fluid intake opening or the respective fluid outlet, which can be arranged on different sides of a cartridge body, designs are also feasible, where the respective passage way can not completely be formed by a channel in the surface of the base body. E.g. designs are feasible, where the passage way has to lead at least partially in form of a conduit through a body in order to reach the respective fluid intake opening or the respective fluid outlet.

In a preferred embodiment the cartridge body is provided with a lid attached to the base plate, whereby the lid at least partially closes the passageways comprised in the cartridge body. This allows for the cartridge body to be manufactured in a simple manner. As discussed above, a fluid passageway can be designed as a conduit that can for example be drilled into a body. Compared to a conduit drilled into a body, a channel or cavity comprised in the surface of the cartridge body can be manufactured more easily. In order to make the fluid passageway(s) that is formed by the one or more channels or cavities fluid tight, it is closed by at least one lid as described in this particular embodiment of the invention. The lid is preferably provided by a plastic film or foil that can be adhered or fused to the cartridge body. The lid may have a thickness of 20 µm to 500 µm and preferably lies in a range of 50 µm to 300 µm, more preferred 75 µm to 250 µm and most preferred 100 µm to 150 µm. In one embodiment, the cartridge body comprises a multiparted lid, for example different lid segments may be used to close one or more channels and/or cavities of the different fluid passageways. In a preferred embodiment, the cartridge body comprises a lid that closes the channels and/or cavities of at least two, preferably all fluid passageways. This design further simplifies the manufacturing process for the cartridge body.

In a preferred embodiment the cartridge body is provided with a base plate, whereby the fluid intake opening B, the fluid outlet B, the sample intake opening, the sample outlet, the fluid opening A and the fluid outlet A are arranged in the same surface of the base plate. Arranging the fluid intake openings and the fluid outlets on the same surface of the base plate allows for the cartridge to be inserted into the processing device in a simple manner.

In a preferred embodiment the fluid intake opening B, the fluid opening A and/or the fluid outlet A is closed by a membrane and a filter. Furthermore, also one or more of the fluid passageway may be covered, respectively sealed, at least partially over their length with a membrane as is shown in the Figures. This measure ensures in addition to the lid that no liquid, in particular sample, can exit the cartridge body. The membrane or filter provided can have the basic function to clean the fluid flowing that enters or exits, for example by keeping out particles transported by the fluid. Furthermore, with respect to the membrane or filter comprised in the fluid opening A that is in fluid communication with the reaction chamber, the filter or the membrane can be used as a type of valve, controlling the flow of fluid, here the sample. In a preferred embodiment, the fluid opening A is provided with a membrane that only allows air or similar fluids to pass through it, but prevents the passage of fluids of other type, especially of fluids of higher density and/or especially water or water based fluids such as the sample. In a preferred embodiment the membrane is hydrophobic. The use of such a membrane allows to control the type of fluid that may flow out of the reaction chamber. The sample may enter the reaction chamber through the sample outlet. Fluid entering the reaction chamber will lead to overpressure in the reaction chamber. However, air can escape through the membrane comprised in the fluid opening A, thereby allowing further sample to enter into the reaction chamber. However, the liquid sample can not pass by said membrane. Thereby, the amount of sample comprised in the reaction chamber is controlled. The reaction chamber is basically locked as soon as the membrane comes into contact with the sample. Therefore, providing a fluid opening A, comprising a respective hydrophobic membrane or filter provides the possibility to control the pressure in the reaction chamber and to control the amount of sample that enters into the reaction chamber through the sample outlet. The size of the reaction chamber can be such that once substantially all air has left the reaction chamber through the membrane comprised in the fluid opening A and therefore, the reaction chamber is completely or almost completely filled with the sample, a pre-determined amount of sample is provided in the reaction chamber for reconstituting the dry composition that is necessary to provide a reconstituted composition comprising the reagents in the necessary concentration.

In a preferred embodiment the cartridge body is a one-piece element. In an especially preferred embodiment, the one-piece element is produced by di-casting or injection moulding. In an alternative embodiment, the cartridge body has a one-piece cartridge body and a lid attached to the one-piece base body. This allows for an easier manufacturing of the cartridge body. The lid can preferably be made as a foil that has certain areas of the foil provided with an adhesive and therefore allows the lid to be permanently attached to the base body.

According to one embodiment, the sample passage way and/or the fluid passage way A can be arranged with a valve. The valve is preferably designed to prevent the flow of fluid through the respective fluid passage way. The advantages were described above and in particular apply if a heating reaction is performed in the sample vessel and/or the reaction chamber. As discussed above, an easy embodiment of a valve can be realized, if the respective flowing passage way is designed to have a bar such as a wall that blocks the channel, thereby interrupting the channel. In order to form the valve, such a channel can be closed with a lid that comprises a movable, e.g. flexible plate in the area of the wall. The movable area can be held down by mechanical means, for example a pin or force comprised in the processing device. If the pin is retracted, the pressure of the fluid in the passage way will push back the movable part of the lid and fluid will be allowed to flow over the wall provided in the channel. According to one embodiment, the movable part of the lid will be connected to the remaining part of the lid by flexible means that on the one hand allow the movable part to move, on the other hand will provide the necessary fluid tightness that prevents the fluid in the passage way to flow anywhere else but the further part of the fluid passage way that follows after the wall. In an alternative embodiment, the lid itself may comprise a bar such as a wall that can be moved into the fluid passageway to block it. E.g. the movable part described above may comprise the wall. If the movable part is moved down, the wall is moved down and blocks the fluid passageway thereby closing the valve designed in such a manner.

The cartridge body may comprise at least one further connection projection for connecting a further reaction chamber, wherein said further connection projection may comprise the same elements as the reaction chamber connection projection described above. Using more than one reaction chamber has the advantage that more than one analysis reaction can be performed using the same cartridge. This allows to test the same sample e.g. for the presence of different pathogens or diseases.

According to an eight aspect, a method is provided for the production of a processing cartridge according to the fifth aspect of the present invention, wherein said processing cartridge to be comprises at least one reaction chamber which comprises a dry composition comprising reagents for performing an analytical method. Said method comprises the following steps:

(a) making from polymer, a cartridge body with at least one channel and/or cavity to provide a fluid passageway between the sample intake opening of the cartridge body and the at least one sample outlet of the cartridge body;
(b) spotting reagents into at least one reaction chamber and drying the reagents therein, thereby providing a reaction chamber comprising a dry composition comprising reagents for performing an analytical method;
(c) closing the at least one channel and/or cavity of the cartridge body with a lid.

The one or more reaction chambers are preferably provided as separate device(s). This simplifies the spotting with the reagents and the drying process which is preferably a freeze-drying process. Details with respect to the dry composition and the components comprised therein were described above in conjunction with the first aspect of the present invention. It is referred to the respective disclosure. After obtaining the dry composition in the one ore more reaction chamber, said method comprises a step of assembling at least one reaction chamber to the cartridge body. Preferably, said assembly is performed after step c).

The cartridge body is preferably produced by injection molding technology. As described above, the cartridge body preferably comprises at least one membrane. It is produced in a multiple-step process, wherein the at least one membrane is assembled into the injection mould and wherein in a first step, the upper or the lower side of the cartridge is injected and in a second step, the other side is injected, thereby providing the cartridge body comprising the membrane.

According to a ninth aspect of the present invention, a system is provided for performing an analytical method of a sample comprising biomolecules comprising
a) a processing cartridge according to the fifth aspect of the present invention; wherein the processing cartridge comprises at least one reaction chamber comprising a dry composition comprising reagents for the analytical method;
b) a vessel for receiving a sample comprising biomolecules, wherein the vessel can be assembled to the processing cartridge;
c) a processing device for receiving the processing cartridge comprising the vessel assembled thereto and for performing the analysis method in conjunction with the processing cartridge.

Said system comprises a processing cartridge as described above. Furthermore, the system comprises a vessel for collecting a sample comprising biomolecules, wherein the vessel can be connected to the processing cartridge. As third element, the system comprises a processing device for receiving the cartridge and performing the analytical method within the processing cartridge. The design of the processing device depends on the analytical method to be performed. Some details will be described subsequently in conjunction with the operating method for performing an analytical method using the respective system.

According to a tenth aspect, an operating method is provided for performing an analysis method using the system according to the ninth aspect, the method comprising:
a) connecting a vessel comprising a sample to the processing cartridge according to the fifth aspect according to the present invention;
b) inserting the processing cartridge into a processing device; and
c) starting a fully automated assay.

Subsequently, we will explain the individual steps of the respective operating method. In a first step, a sample is obtained and inserted into the vessel. The vessel preferably comprises a lysis composition suitable for lysing the collected sample and being suitable for reconstitution of the dry composition comprised in the reaction chamber of the processing cartridge. The lysis composition preferably is a lysis solution as described above. The vessel comprising the sample can be closed for example in order to be able to handle the vessel without a risk of spilling the comprised sample. For starting the operation method, the vessel comprising the sample and the lysis composition is connected to the processing cartridge. For this purpose, the processing cartridge comprises suitable means allowing a tight connection between the vessel and the cartridge. Details were described above. As soon as the vessel was connected to the cartridge, the cartridge comprising the vessel assembled thereto can be inserted into the processing device. Hence, all that is needed to do by the customer is to connect the vessel comprising the collected sample to the processing cartridge and the insertion into the processing device. All subsequent steps are performed automatically.

According to a preferred embodiment, the sample is lysed within the vessel. Preferably, the lysis composition comprised in the vessel comprises a solid support as described above for clearing the lysed sample. Preferably, lysis is assisted by heating. For this purpose, the processing device may comprise a heating unit. Furthermore, if a magnetic solid support is used for clearing the lysate, the processing device preferably comprises a magnet in order to allow the collection of the magnetic solid support with the bound precipitates/contaminants at the bottom or the side wall of the vessel. Thereby, the lysed sample can be cleared highly efficiently. The lysed sample, which preferably is a cleared lysed sample, enters the processing cartridge through the sample intake opening. Preferably, the processing cartridge has a cartridge body design as described above in conjunction with the fifth and/or sixth aspect of the present invention, with a fluid intake opening B, a first fluid passage way and a fluid outlet B as well as a sample intake opening. As described above, the respective fluidic system provides a very simple design in order to achieve the transfer of the sample, preferably the cleared lysate, into the processing cartridge. The processing device may comprise a pressure generating apparatus which allows to pump air through the fluid intake opening B. The air enters into the reaction vessel through the first fluid passage way and the fluid outlet B. The resulting pressure has the effect that the sample comprised in the vessel, which preferably is a cleared lysate, is pushed up and therefore enters the processing cartridge through the sample intake opening, which preferably is designed as a sample intake opening as described above. Further ways to achieve the entrance of the sample were described above.

In order to assist the entrance of the sample, the processing cartridge preferably comprises a tube which extends into the vessel and preferable extends into the sample, which preferably is a cleared lysed sample. Upon entry into the processing cartridge through the sample intake opening, the sample passes through the sample passageway until it reaches the sample outlet. From the sample outlet the sample, which preferably is a cleared lysate obtained as described above, enters the reaction chamber comprising a dry composition. Thereby, the sample, which preferably is a lysed sample, comes into contact with the dry composition and accordingly reconstitutes the same. The reconstitution process can be assisted for example by mixing, vortexing or magnetic steering as described above. In case the dry composition comprises a magnetic material to allow magnetic steering, such as for example a magnetic foil, the processing device comprises a magnet which allows the movement of the magnetic material comprised in the dry composition within the reaction chamber. According to one embodiment, the processing device comprises an electromagnet under alternating current voltage. According to a further embodiment, a rotating permanent magnet is provided.

The filling of the reaction chamber is controlled in order to ensure, that only a predetermined amount of liquid is used for reconstituting the dry composition. According to a preferred embodiment, the filling of the reaction chamber with the sample stops as soon as the sample reaches the hydrophobic membrane which forms a barrier for the liquid sample. As is shown in the figures, said hydrophobic membrane is preferably located at the end of the third fluid intake opening.

After reconstitution of the dry composition, the analytic method can be performed. The processing device comprises the machinery that is necessary for performing the analytical method. For example, if a nucleic acid amplification is performed, the processing device comprises in the area where the reaction chambers are located all elements that are necessary for performing a PCR reaction, such as in particular heating and cooling elements. Furthermore, the processing device comprises preferably a fluorescence detector in order to be able to perform a real time PCR and/or to be able to detect fluorescent signals. However, the processing device may also comprise other means for performing a detection, such as for example a spectrophotometric measurement, a haze measurement, the determination of nanoparticle aggregation and the like. The result of the assay is then presented preferably also by the processing device, e.g. in a readout unit.

The whole system according to the present invention is unique due to its very simple design and the very simple fluidic. The processing cartridge uses a hydrophobic membrane as sample stop and metering structure(s) and does not comprise any complicated valves, but instead is able to temporarily close the fluid passageways by barriers such as bars/walls. Furthermore, it is capable of moving the sample within the system simply by pumping air into the vessel or by making use of the overpressure that is generated when the sample is heated in the vessel that is connected to the processing cartridge. Therefore, in contrast to other processing cartridges and systems, the whole design is reduced to a minimum, thereby allowing the cost efficient production of all elements. After completion of the assay, the whole processing cartridge can be discarded together with the vessel that is connected thereto. After assembly of the vessel to the processing cartridge, the whole system is closed, thereby preventing that the sample comprised in the cartridge or for example the amplification products can escape the cartridge. For this purpose, suitable membranes are used. The only liquid that needs to be used for performing the analytical method comes from the vessel comprising the sample. The vessel is a collection vessel that at the same time works as a sample processing vessel because the preparation of the sample for the analysis within the processing cartridge, e.g. the sample lysis, is performed therein. Furthermore, the vessel also functions as a liquid container comprising the sole liquid, namely the sample, which is, if necessary, pretreated to make it suitable for reconstitution of the dry composition that is comprised in the reaction chamber. If nucleic acids are the biomolecules of interest, the sample is preferably lysed and cleared within the vessel as described above in conjunction with the first aspect of the present invention. The sample that enters the cartridge body through the sample intake opening is suitable for reconstituting the dry composition that is comprised in the reaction chamber so that the reconstituted composition is suitable for performing the intended analytical method comprising e.g. an amplification and detection reaction, with the required sensitivity and/or specificity. According to one embodiment, the sample is prepared for this purpose in the vessel, e.g. lysed and cleared as described above. The vessel preferably comprises 500 µl to 3 ml of a lysis and/or stabilisation solution. A preferred lysis solution for preparing the sample for a nucleic acid analysis is described above. Said lysis solution preferably comprises a solid support for clearing the lysate as described above. The functional test unit is obtained by connecting the vessel to the processing cartridge.

The processing device for operating the assay protocols using the processing cartridge of the present invention comprises an elaborated mechanical system. The design depends on the analytical method to be performed. The main mechanic-electronic features inside the processing device are heating elements to support the lysis of the sample, a pump suitable for pumping air into the vessel when the vessel is assembled to the processing cartridge, at least one magnet for magnetic steering. Furthermore, a PCR unit is provided in case a PCR reaction shall be performed. The thermal cycling of a PCR reaction that is performed within the processing device is commonly facilitated by Pelletier elements. All connections between the processing cartridge and the processing device are preferably sealed with a membrane. The whole system comprises a low complexity.

Numeric ranges referred to herein are inclusive of the numbers defining the range. The headings provided herein are not limitations of the various aspects or embodiments of this invention which can be read by reference to the specification as a whole. According to one embodiment, subject matter described herein as comprising certain steps in the case of methods or as comprising certain ingredients in the case of compositions, solutions and/or buffers refers to subject matter consisting of the respective steps or ingredients. It is preferred to select and combine preferred embodiments described herein and the specific subject-matter arising from a respective combination of preferred embodiments also belongs to the present disclosure.

FIG. 1 shows the results of a quantitative PCR using cleared lysates that were obtained according to example 1 and non-cleared lysate (reference). MasG: MagAttract Suspension G (QIAGEN); MasB: MagAttract Suspension B (QIAGEN), Seradyn (carboxylated magnetic particles); ref: lysate without magnetic particle treatment (clearing).

Figure 2:
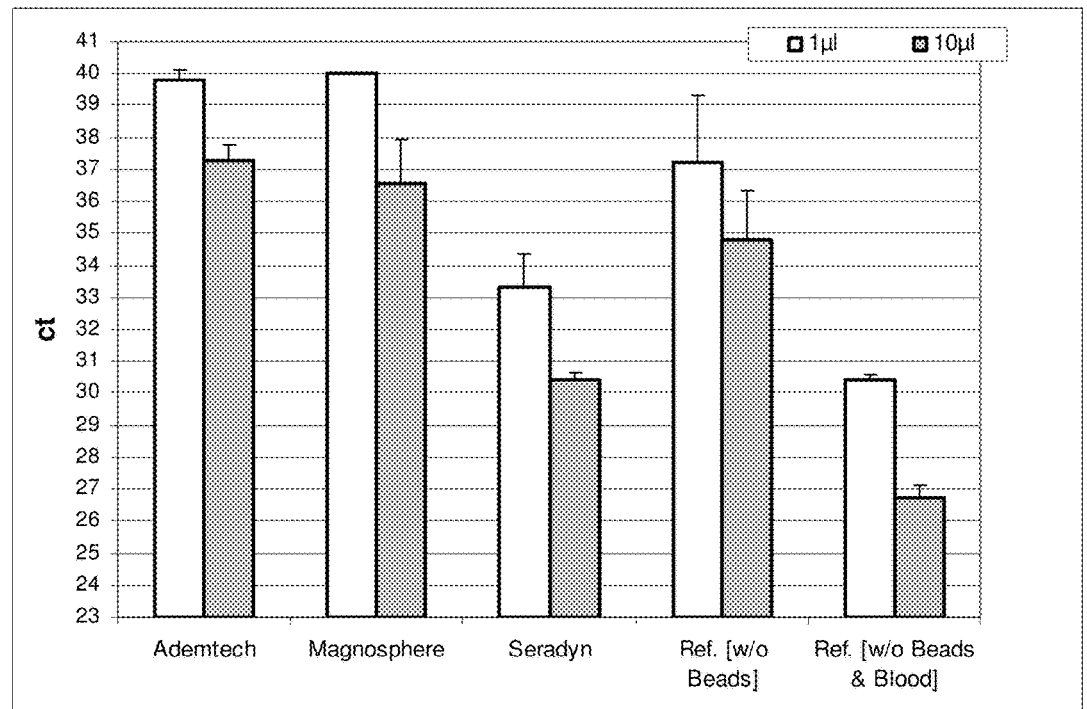

FIG. 2 shows the results of example 2, wherein different beads were tested for lysate clearing. One reference was processed without beads but with blood (no lysate clearing) and the second reference was tested without beads and without blood but with spiked-in bacteria. Therefore, the second reference shows the results of a PCR wherein basically no PCR inhibiting compounds/contaminants are present.

Figure 3:
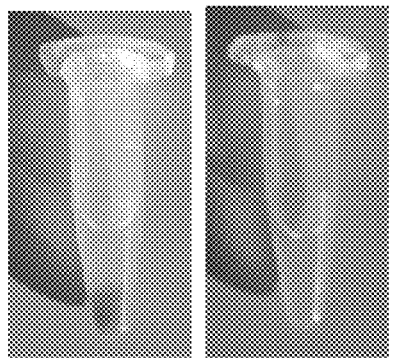

FIG. 3 demonstrates the efficiency of the lysate clearing process according to the present invention. On the left side, a non-cleared blood lysate is shown, on the right hand side the same sample, wherein, however, the lysate clearing according to the present invention has been performed.

Figure 4:
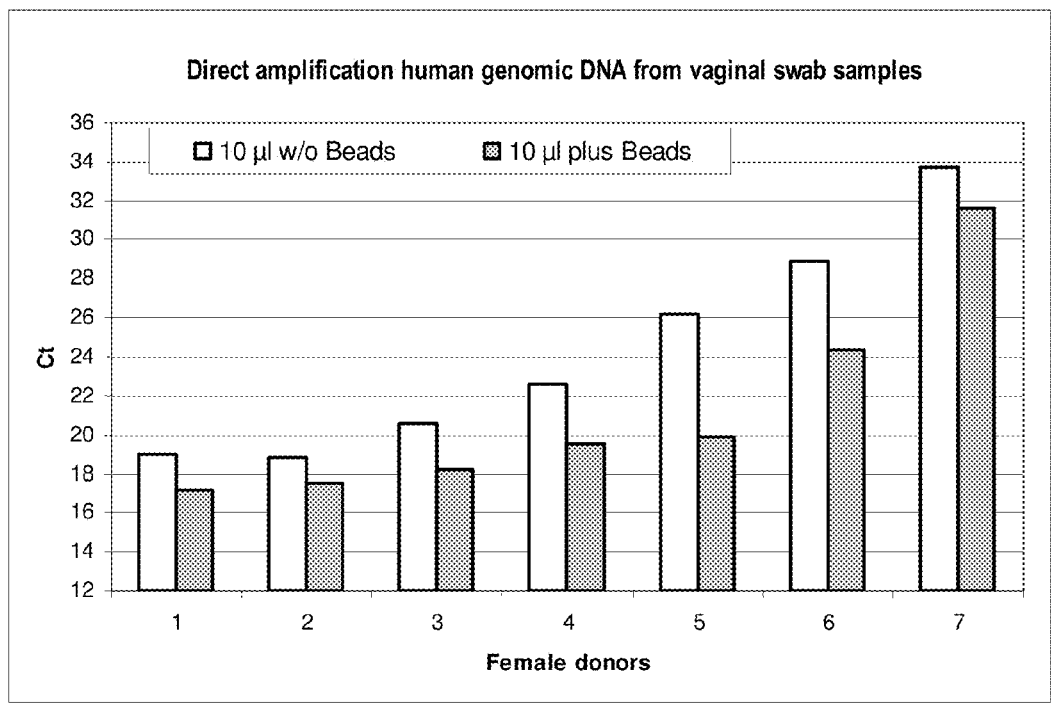

FIG. 4 shows the results of example 3, wherein seven different vaginal swabs sample were used to produce a cleared lysate; 10 μl cleared or crude (uncleared) lysate was directly used in a quantitative PCR.

Figure 5:
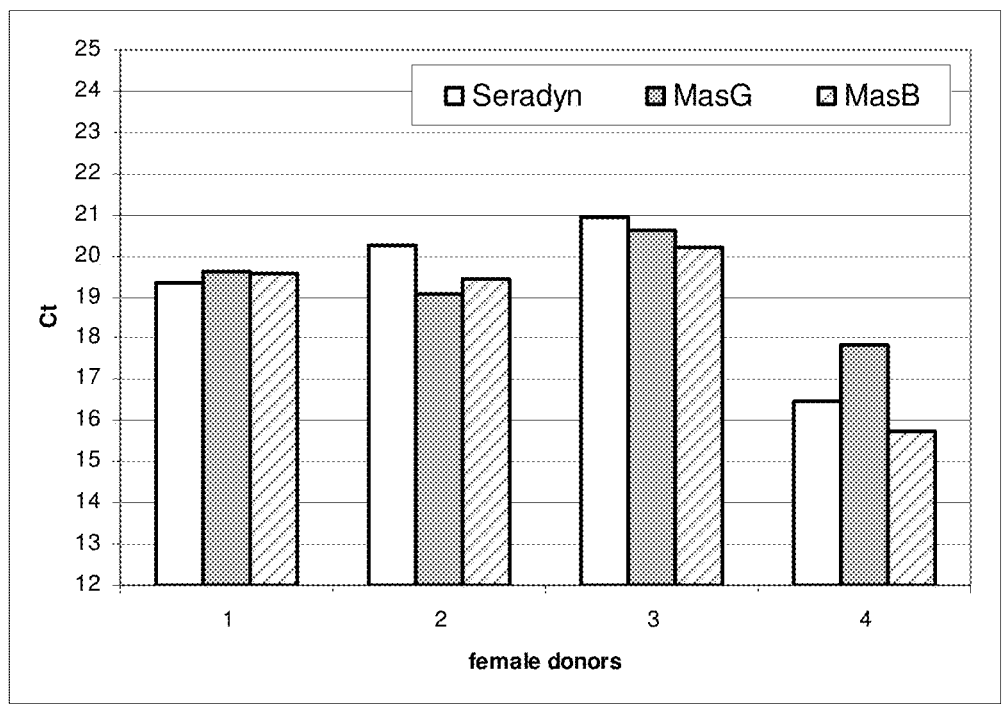

FIG. 5 shows the results of four different vaginal swab samples which were lysed and wherein the lysate was cleared using different types of magnetic particles. 10 μl lysate was used in a quantitative PCR. Seradyn (carboxylated beads); MasG (MagAttract suspension G (QIAGEN)); MasB (MagAttract suspension B (QIAGEN)).

Figure 6:
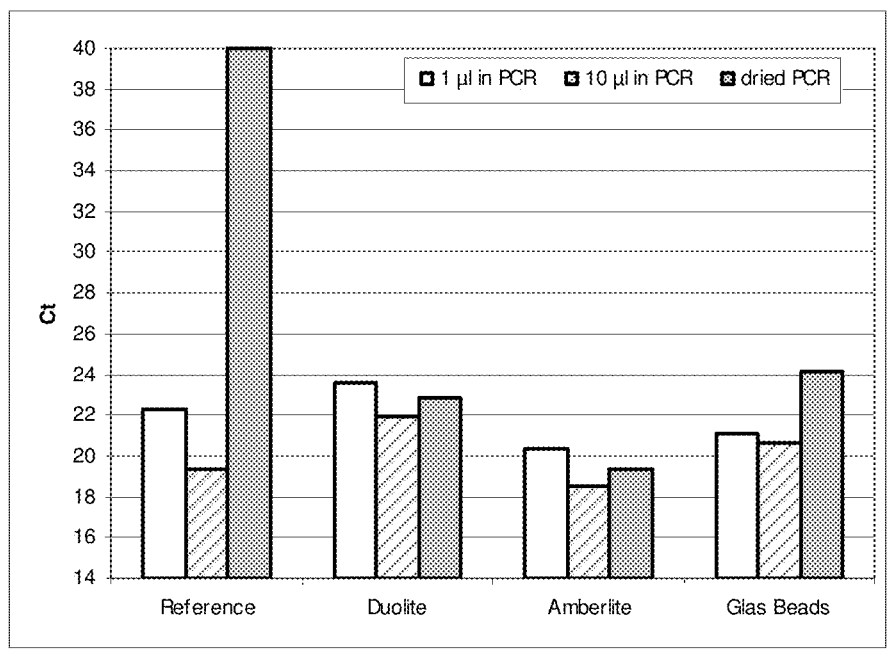

FIG. 6 shows pooled vaginal swab samples which were processed using different magnetic particles and wherein different volumes of the cleared lysate were used directly in a quantitative PCR, wherein human genomic DNA was detected. The dried PCR compositions were reconstituted by adding 25 μl of the lysate or cleared lysate.

Figure 7:
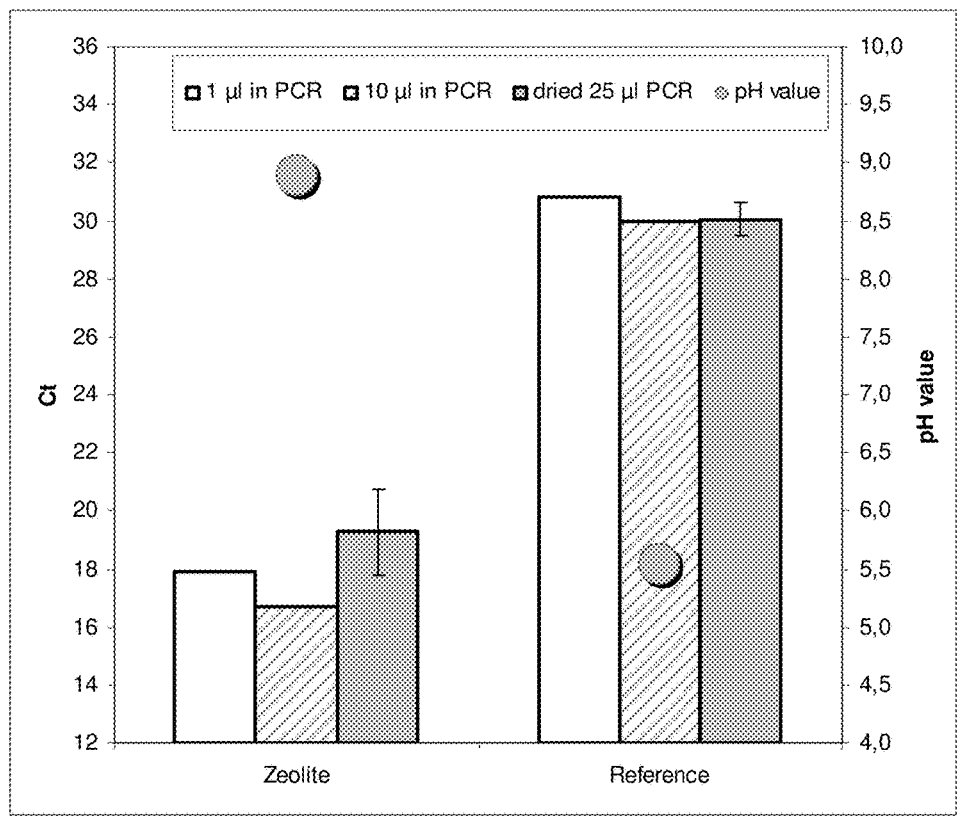

FIG. 7 shows the beneficial effect of the incorporation of zeolites during lysis when processing acidic samples such as vaginal swab samples. The samples were processed with and without zeolites according to example 6.

Figure 8:
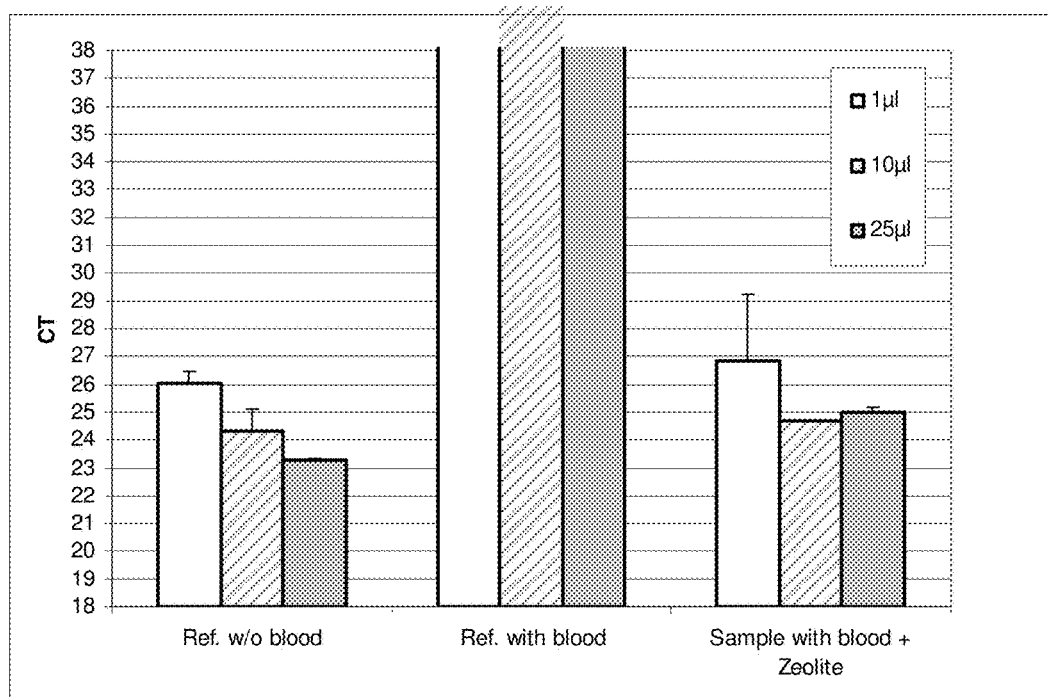

FIG. 8 shows the results of example 7, wherein blood samples were processed with and without zeolites and different volumes of lysate were directly used in a quantitative PCR in order to detect genomic DNA of *E. coli*. 25 μl cleared lysate was used to reconstitute a dried PCR mix comprising the primers and probes.

Figure 9:
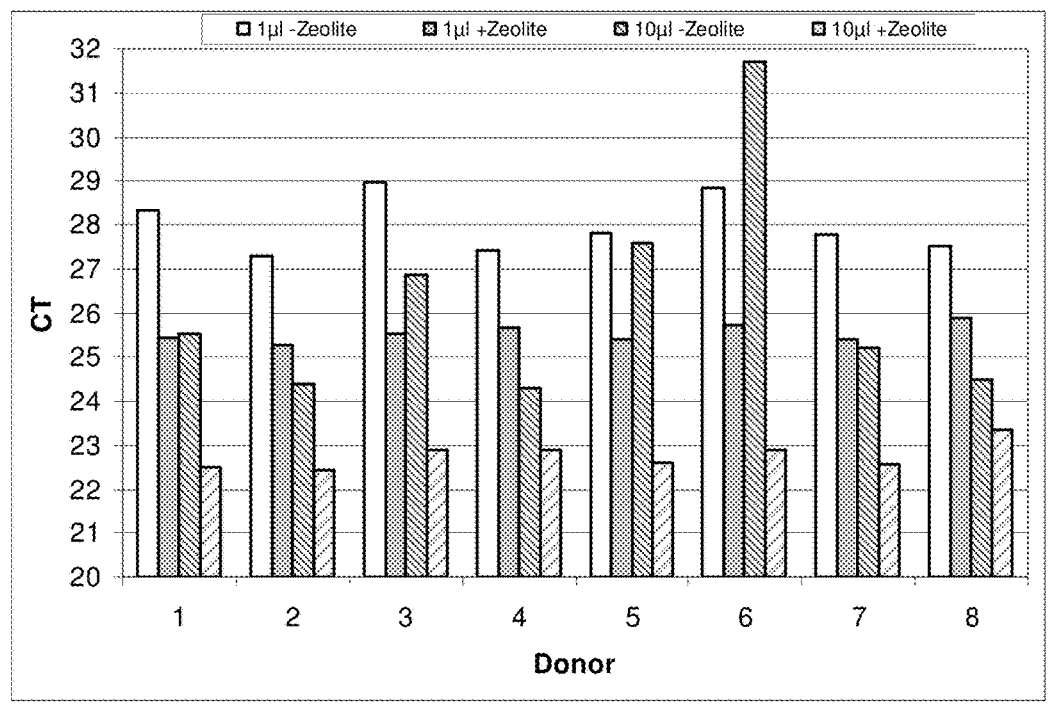

FIG. 9 shows the results of example 8. Buccal swab samples from eight different donors were processed with and without zeolites and with different volumes of lysate which were used directly in a quantitative PCR.

Figure 10:
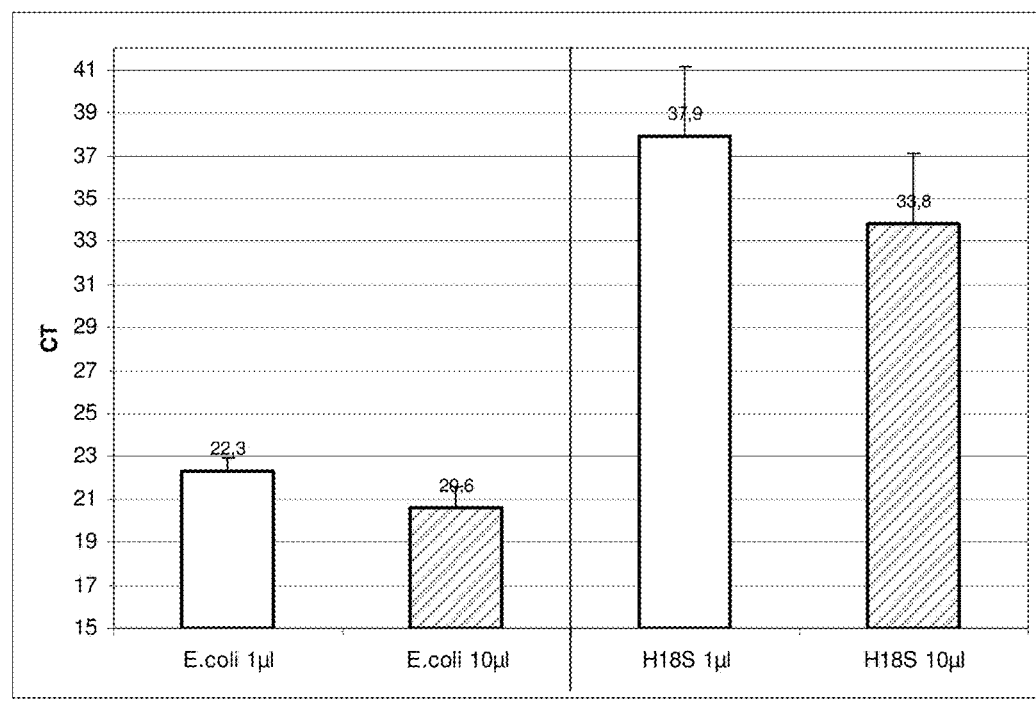

FIG. 10 shows the results of example 9, wherein stool swab samples from 16 independent preparations were processed with Seradyn beads; and different volumes of the obtained cleared lysates were directly used in a quantitative PCR, wherein *E. coli* genomic DNA and a human gene was detected.

Figure 11:
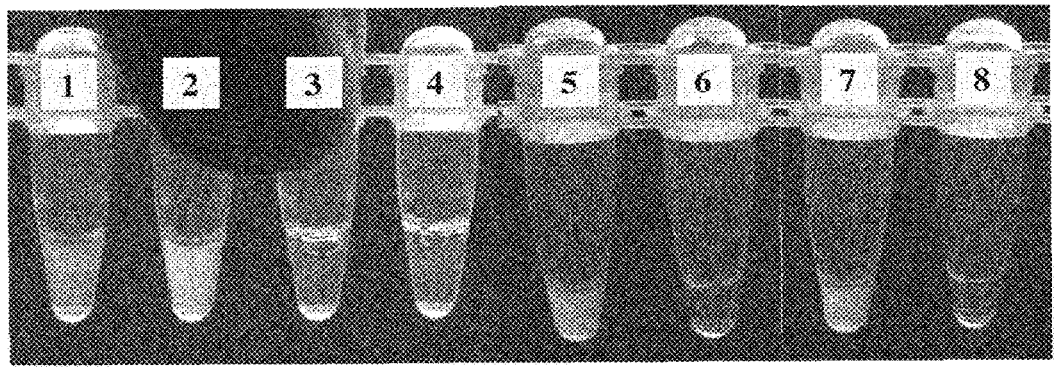

FIG. 11 shows the effect on the PCR when removing precipitates using carboxylated magnetic beads (see example 11). Samples 1, 2, 5 and 7 are vaginal swab samples wherein no magnetic beads were added for clearing the lysate. Samples 3, 4, 6 and 8 are cleared lysates that were obtained by adding carboxylated magnetic particles to the lysate of the vaginal swab samples.

Figure 12A:
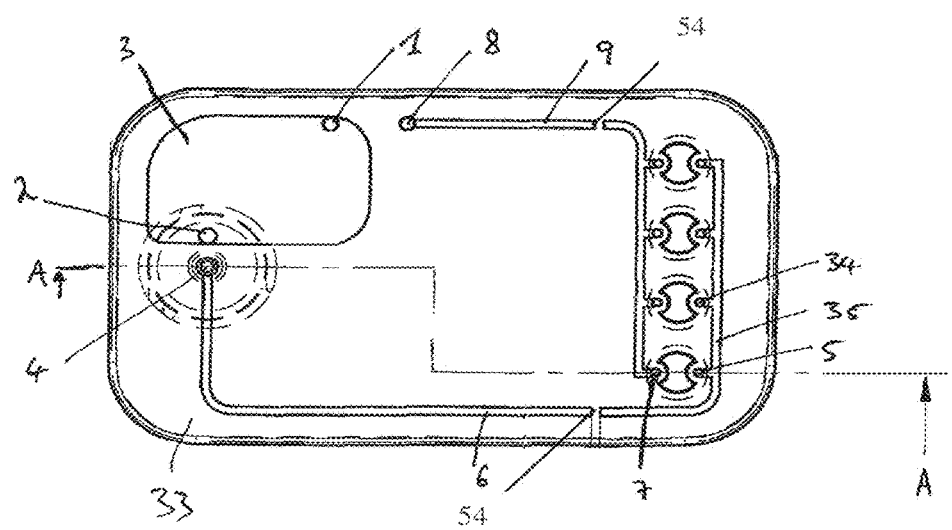
Figure 12B:
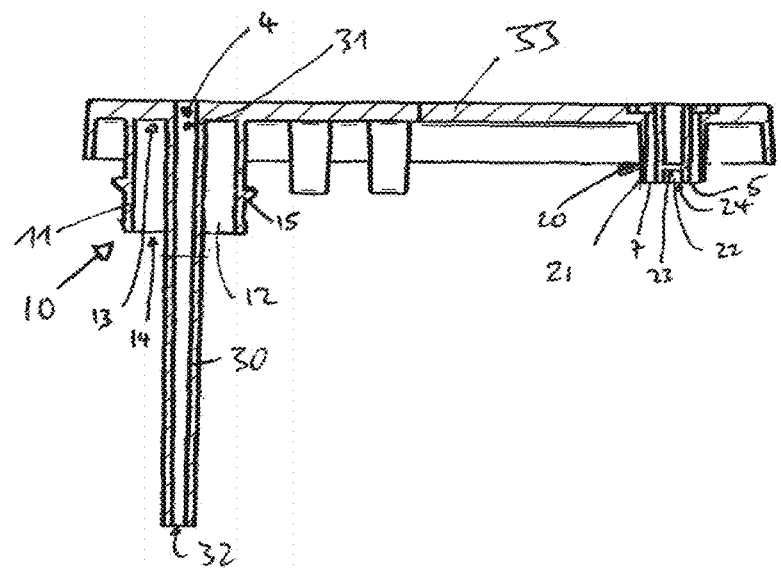

FIG. 12a) shows the cartridge body according to the invention in a top view, and FIG. 12b) shows the cartridge body according to FIG. 12a) in a side view cut along the line A-A in FIG. 12a).

FIG. 13 shows a side view of the cartridge body according to FIG. 12 with assembled sample vessel and reaction chambers.

Figure 14:
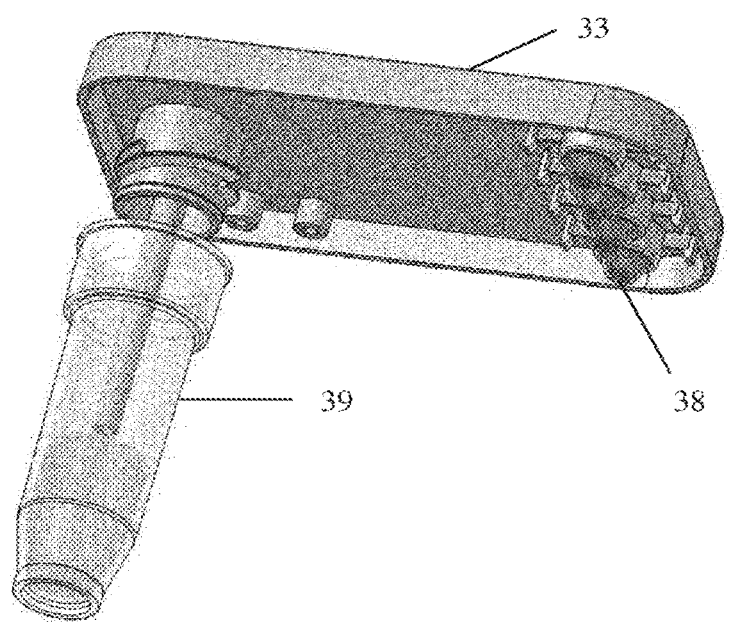

FIG. 14 shows the cartridge according to the invention in a perspective view from below.

Figure 15:
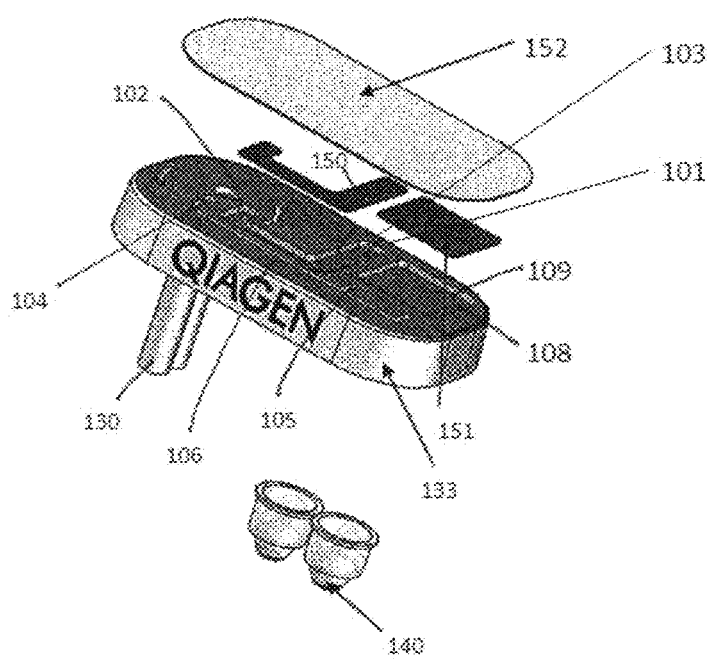

FIG. 15 shows an exploded perspective view of a further embodiment of the cartridge according to the invention.

Figure 16:
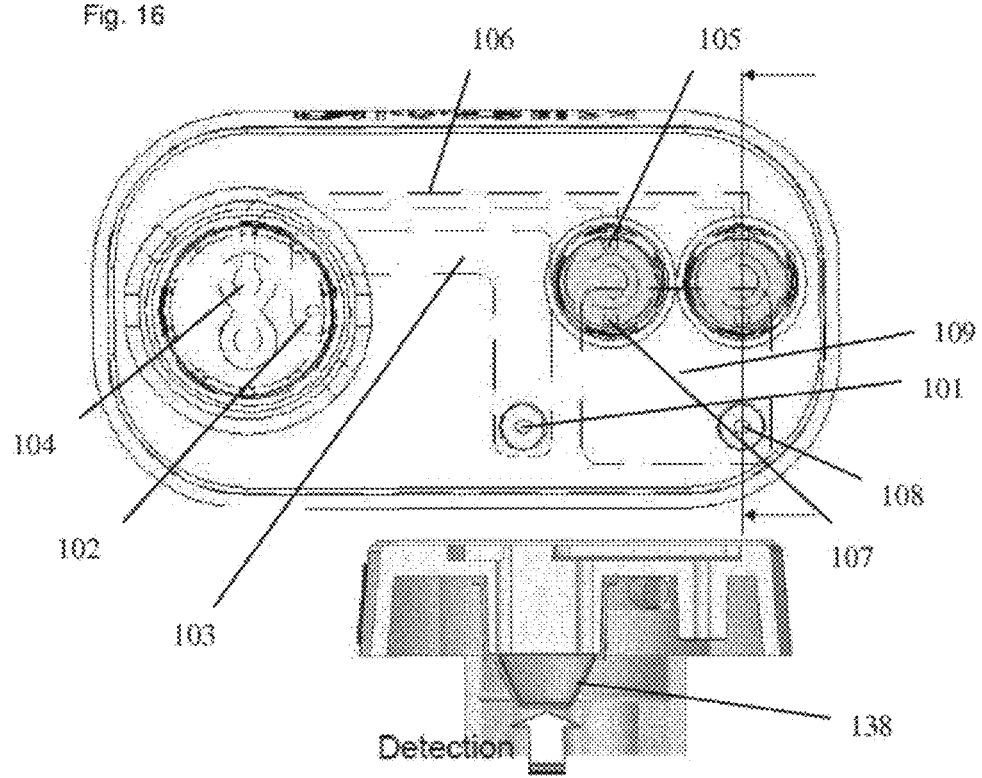

FIG. 16 is a top view of the sample cartridge as shown in FIG. 15.

Figure 17:
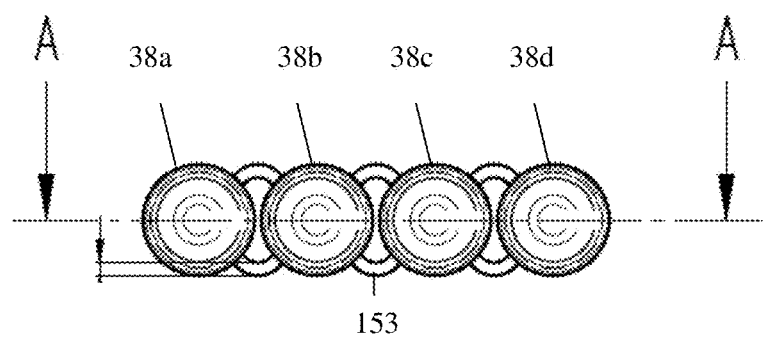
Figure 17:
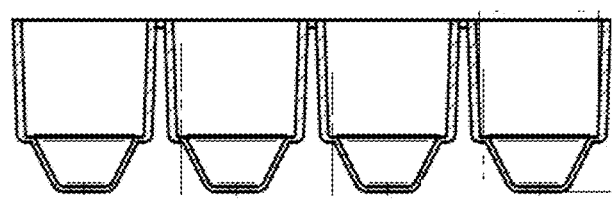

FIG. 17 shows a device comprising multiple reaction chambers that can be assembled to the cartridge for providing the processing cartridge comprising the reaction chambers.

Figure 18:
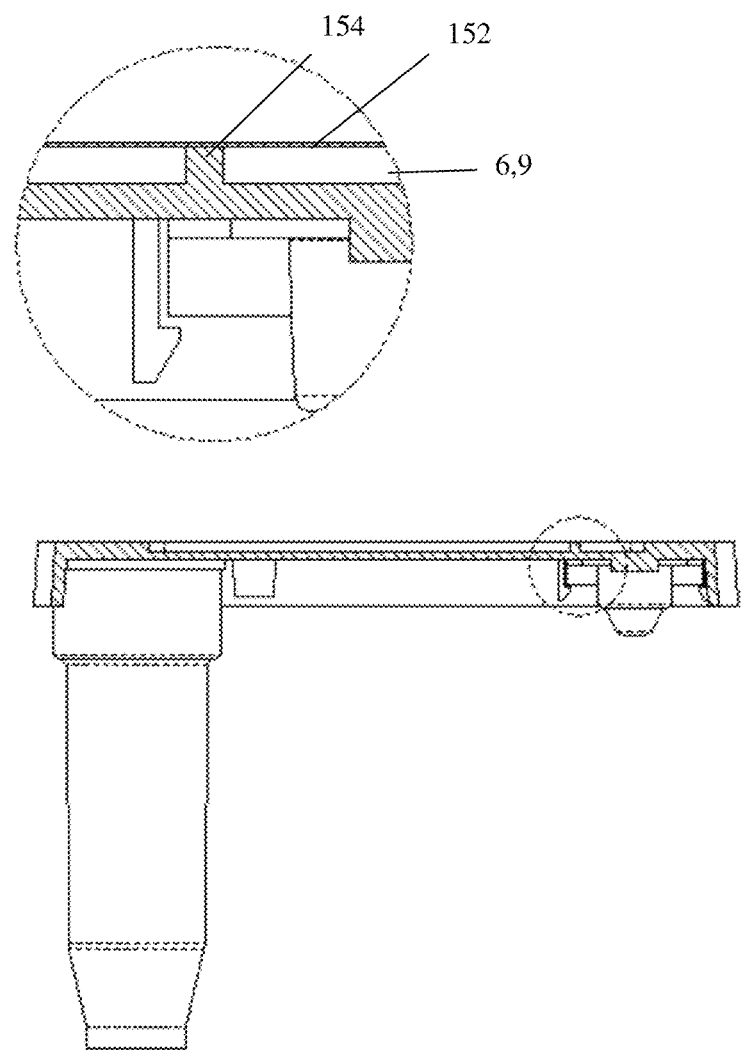

FIG. 18 illustrates the function of the walls within the fluid passageways 6 and 9 which function as a valve.

Figure 19:
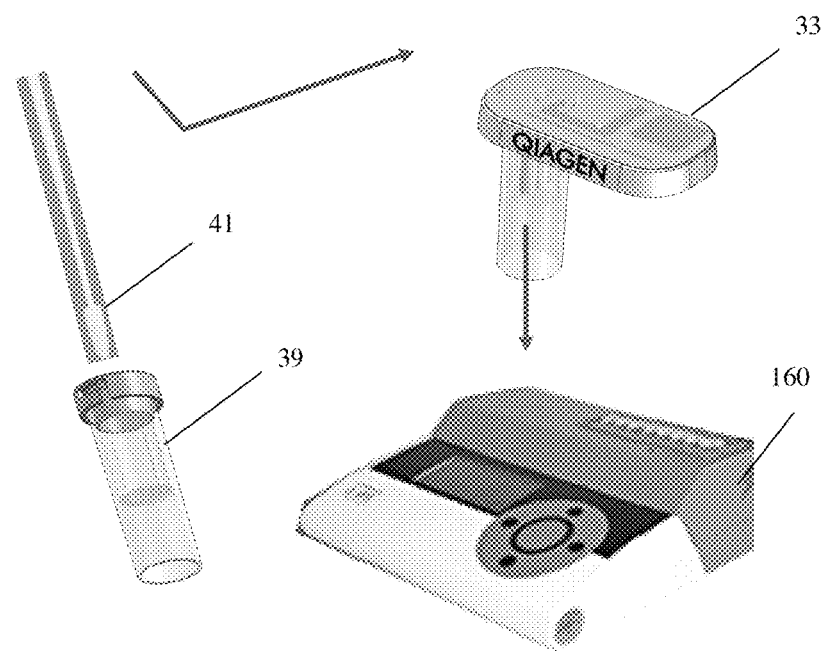

FIG. 19 illustrates the system according to the present invention.

Figure 20:
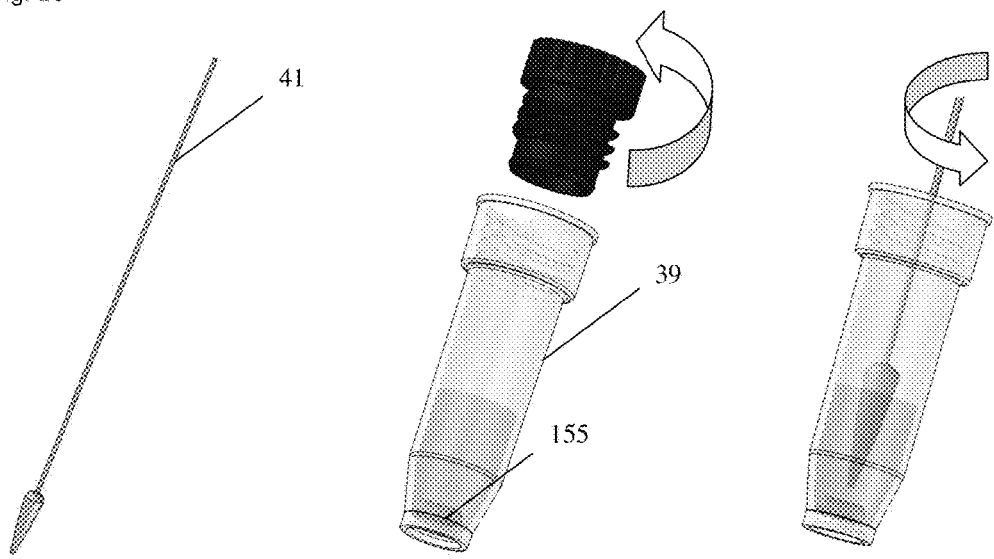

FIG. 20 illustrates that collection of the sample.

Figure 21:
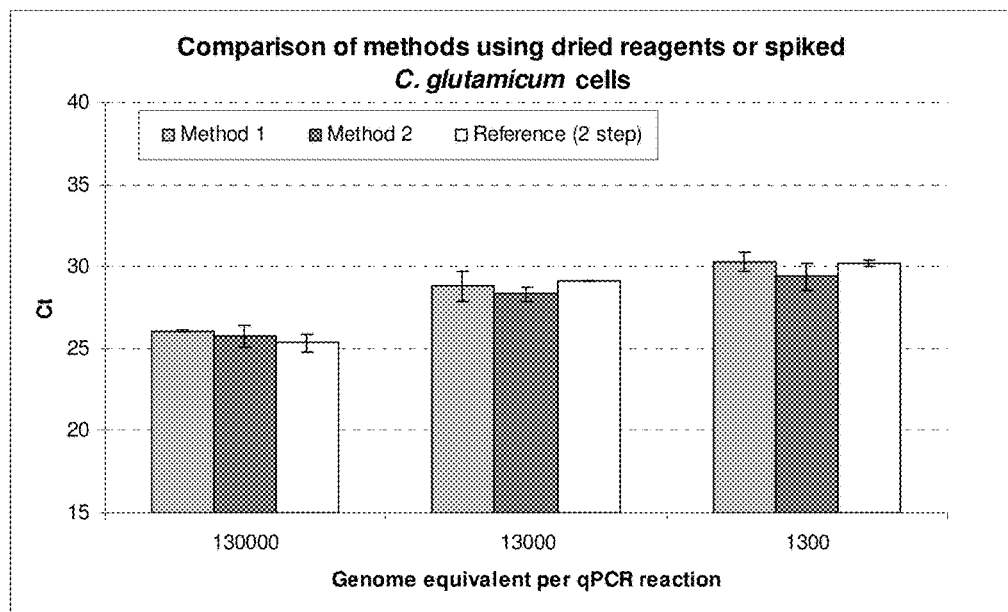

FIG. 21 illustrates the performance of different embodiments of the present invention for performing the lysis of the sample and the reconstitution of the freeze-dried PCR mix as described in example 12.

The cartridge body 33 shown in FIG. 12a) has a fluid intake opening B (1) and a fluid outlet B (2). A fluid passageway B (3) is provided by bordering walls arranged at the top surface of the cartridge body. Thereby, a cavity is formed which allows a fluid to passage. Hence, in the embodiment shown in FIG. 12a) a fluid passageway B (3) is provided that has an approximately square cross section, whereby the fluid intake opening B (1) is arranged in one corner of the square fluid passageway B (3) and the fluid outlet B (2) is arranged in a second corner of the fluid passageway B (3). The fluid, preferably air, that is allowed to enter the fluid passageway B (3) via the fluid intake opening B (1) flows from the fluid intake opening B (1) across the square-shaped fluid passageway B (3) to the fluid outlet B (2) and enters the sample vessel, if a sample vessel is connected to the cartridge body. As described herein, a pump can be connected to the fluid intake opening B (1) in order to introduce air with pressure into the cartridge and hence the sample vessel, thereby alleviating the entry of the sample into the cartridge. The cartridge body 33 shown in FIG. 12a) is further provided with a sample intake opening 4 and a sample outlet 5. The sample intake opening 4 and the sample outlet 5 are connected by a sample passageway 6. The sample passageway 6 is created by a channel on the top surface of the cartridge body. A sample that enters the cartridge body from the vessel through the sample intake opening 4 runs along the sample passageway 6 until it reaches the sample outlet 5 through which it enters the reaction chamber, if it the reaction chamber is assembled to the cartridge body 33. The embodiment shown in FIG. 12 is set up for receiving four reaction chambers which are connected to the cartridge body via the four reaction chamber connection projections of the cartridge body 33. The reaction chamber connection projection(s) can be seen in FIG. 12b). Upon assembly of the reaction chambers, they are in fluid communication with the sample passageway 6 which branches and wherein each branch ends in a different sample outlet that opens into a different reaction chamber. As described herein, it is, however, also within the scope to provide the reaction chamber as integral part of the cartridge body.

Furthermore the cartridge body is provided with a fluid opening A (7) and a fluid outlet A (8). A fluid passageway A (9) that is designed similarly to the sample passageway 6 is a channel in the top surface of the cartridge body connects the fluid opening A (7) and the fluid outlet A (8). The fluid opening A (7) and the sample outlet 5 are each designed as tube that is comprised partially in a convexity of a side wall of the reaction chamber connection projection. Said tubes are in fluid communication with the reaction chamber. The fluid opening A (7) and the sample outlet 5 are arranged oppositely to each other. Designing the fluid opening A (7) and the sample outlet 5 as tubes at least partially in the side wall of the reaction chamber has the advantage that the flow of the fluid into the reaction chamber is well-regulated. The entry of the sample into the reaction chamber via the tubular sample outlet 5 is similar to as if the sample was pipetteted manually to the side wall of the reaction chamber. Thereby, an uncontrolled flushing of the reaction chamber by the sample can be prevented that could result in an irregular filling of the reaction chamber. The fluid opening A (7) comprises a hydrophobic membrane as liquid barrier. The membrane prevents a liquid such as in particular the sample which enters the reaction chamber to pass by said barrier. Therefore, due to the membrane in the fluid opening A no liquid can enter the fluid passageway A (9). However, the hydrophobic membrane allows air to pass, at least before it is wetted with a liquid. Thereby, air that is displaced by the sample can exit the sample passageway 6 and the reaction chamber through the fluid opening A (7). Thus, with respect to air, the fluid opening A (7) can be considered as a fluid intake opening, which guides the air into the fluid passageway 9 from which it escapes the cartridge through the fluid outlet A (8). The fluid outlet A (8) and the fluid intake B (1) both comprises a hydrophobic membrane for sealing the cartridge against an unintentional leakage of liquid, in particular of the sample and/or the reaction products (e.g. amplicons) comprised in the reaction chamber. This fluid tight sealing of the processing cartridge once the sample vessel is assembled has the advantage that the whole processing cartridge including the connected sample vessel can be discarded easily after use.

The sample passageway 6 and the fluid passageway 9 comprise small bars 54 which block the fluid passageways 6 and 7 by disrupting the channel that provides the fluid passageway. Together with the lid (not shown) of the processing cartridge which preferably is a foil which closes the cartridge body, the bars function as a valve which allows to reversibly close and hence seal the sample passageway 6 and the fluid passageway A. This is advantageous because it prevents that a liquid, such as e.g. evaporated water that originates from a heating reaction that is performed either in the connected sample vessel or in the assembled reaction chamber runs through the sample passageway 6 and the fluid passageway A. With respect to the sample passageway 6, it is advantageously prevented that a liquid such as water that evaporates from the sample vessel during a heating step that is performed to lyse the sample accidentally runs through the sample passageway 6 and reaches the reaction chamber comprising the dry composition. Such an escape of evaporated liquid may result in a partial rehydration of the dry composition comprised in the reaction chamber what may compromise said dry composition thereby jeopardizing the performance of the subsequent analytical method. By applying pressure onto the lid during the heat treatment that is performed for sample lysis, the valves are closed, thereby preventing that evaporated liquid reaches the reaction chamber. After lysis, the pressure is withdrawn from the lid, thereby opening the valve and allowing the sample to flow over the small bars 54, which accordingly can enter the reaction chamber through the sample outlet 5. With respect to the blockade of the fluid passageway A (9), evaporation of the liquid comprised in the reaction chamber can be prevented. Even though the fluid opening A (7) comprises a hydrophobic membrane, evaporation can sometimes not be completely prevented by the membrane if a heating step is carried out in the reaction chamber due to the generated pressure. Thus, providing a bar 54 in the fluid passageway A (9) is particularly advantageous if a heating step is carried out in the reaction chamber.

As can be seen in FIG. 12 b) the cartridge body is provided with a sample vessel connection projection 10. The sample vessel connection projection 10 is made up of side walls 11 that encompass a first chamber 12 that is further formed by a base wall 13 and that has an opening 14 opposite the base wall 13. The side walls of the connection projection are adapted to fit into an opening of a sample vessel and for the sample vessel to be connected to the side walls 11 of the connection projection 10. As can be seen in FIG. 12 b) the sample intake opening 4 is arranged in the base wall 13. As can be seen from FIG. 12 a), the fluid outlet B (2) is also arranged in the base wall 13. The sample vessel can be connected to the side walls 11 of the sample vessel connection projection 10 by means of a external thread 15 provided on the outside of the side walls 11.

The cartridge body is further provided with a reaction chamber connection projection 20 that is made up of side walls 21 that encompass a second chamber 22 that is further formed by a base wall 23 and that has an opening 24 opposite the base wall 23. The side walls 21 of the connection protection are adapted to fit into an opening of a receptacle that forms the reaction chamber. Said receptacle that forms the reaction chamber can be connected to the side walls of the reaction chamber connection projection 20. As can be seen in FIG. 12b) the sample outlet 5 is arranged as tube or channel in one of the side walls 21 and opens at the lower end of the side wall 21. Likewise the third fluid opening A (7) is arranged in one of the side walls 21 and opens at the lower end of that side wall 21. The hydrophobic membrane is provided at the upper end.

As can be seen from FIG. 12b) a tube 30 is provided. The tube 30 has a first end opening 31 and a second end opening 32. The first end opening 31 is aligned with the sample intake opening 4. As can be seen from FIG. 12b) the tube 30 is arranged one piece with the cartridge body 33.

Figure 13A:
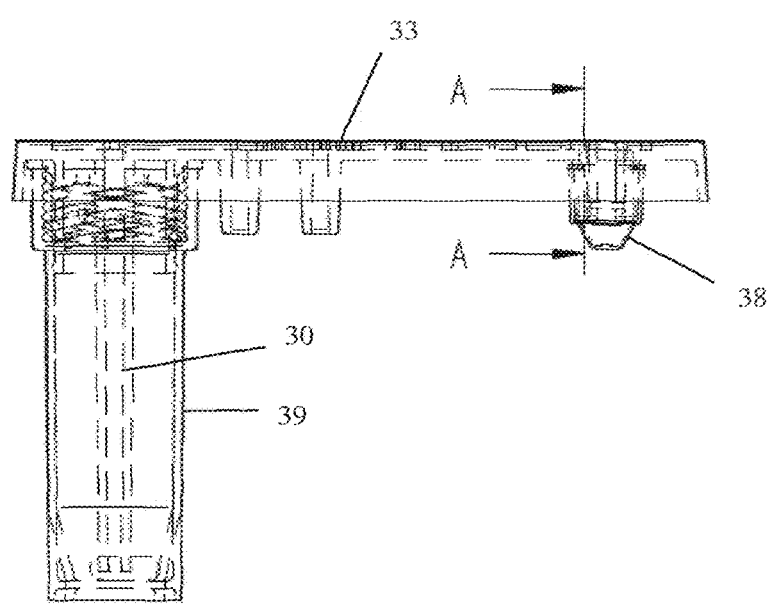

FIG. 13a) shows a side view of the same cartridge body 33 shown in FIG. 12, wherein a sample vessel 39 has been assembled to the cartridge body. Upon assembly, the tube 30 projects into the sample vessel 39 and therefore is located within the lysis solution when the sample tube 39 is filled with the lysis solution and the sample to be analyzed thereby alleviating the entry of the sample. Furthermore, the sample processing cartridge comprises a reaction chamber 38 which comprises the dry composition comprising reagents for performing the analytical method of interest. As can be seen from FIG. 13b), four reaction chambers 38 (a) to 38 (d) are provided. The reaction chambers 38 are provided as one separate device that is mounted on the reaction chamber connection projections 20 for assembly to the cartridge.

Figure 13B:
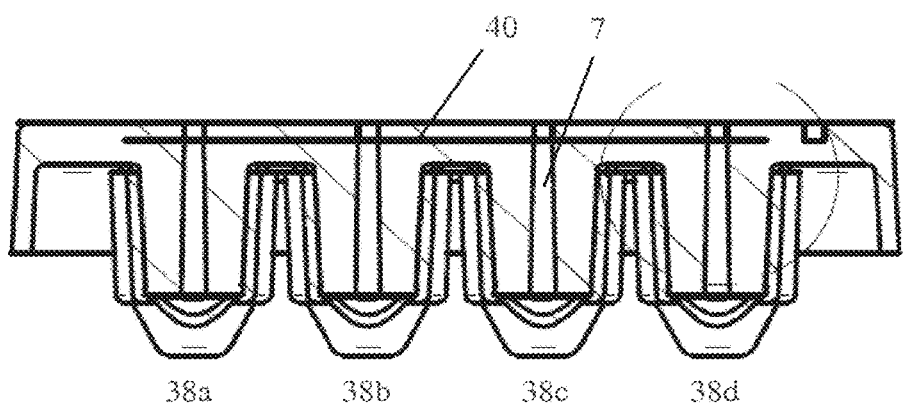

FIG. 13b) shows the device comprising the reaction chambers 38 (a) to 38 (d) according to FIG. 13a) in a side view cut along the line A-A in FIG. 13a). The reaction chambers 38 (a) to 38 (d) comprising the dry reagents for performing the analytical method are assembled via the reaction chamber connection projections 20 to the cartridge body 33. The fluid opening A (7) is sealed by a membrane 40 which is hydrophobic and porous and allows the passage of air but not liquid. Passage of air is hindered, once the hydrophobic membrane 40 has been wetted with a liquid. Therefore, the reaction chamber 38 is sealed, as soon as the sample wets the hydrophobic membrane 40.

The cartridge body 33 shown in FIGS. 12 and 13 can form part of a processing cartridge that is assembled with a sample vessel 39 as is shown in FIG. 14. In the embodiment shown in the FIGS. 12, 13 and 14, the cartridge is designed to have four reaction chambers 38. For this reason, the sample passageway 6 of the cartridge body shown in FIG. 12 branches, wherein each branch ends in a sample outlet for each reaction chamber. Furthermore, each reaction chamber comprises, respectively is connected to a fluid opening A (7), thereby allowing the sample to flow into the corresponding reaction chambers and allowing air to escape. The reaction chambers 38 are connected to the fluid passageway A (9) in order to guide the air that escapes from the reaction chambers through the corresponding fluid openings A to the fluid outlet A from which it exits the cartridge. As shown in FIG. 13 b), the fluid opening A (7) of all reaction chambers comprises a membrane 40 in order to allow air to escape the reaction chamber and to control the filling of the reaction chamber. Here, one membrane 40 is used that goes through all fluid openings A (7). The reaction chamber 38 contains the dry composition comprising reagents for performing an amplification reaction such as primers, probes, enzymes, dNTPs and a buffer.

As is shown in FIG. 14, a sample vessel 39 can be assembled to the cartridge body 33. The sample vessel 39 has a sample vessel opening that is arranged in such a manner that the sample vessel opening is in fluid connection with the sample intake opening 4 which comprises here a tube 30. The sample vessel 39 has an inner thread and is screwed onto the external thread 15 of the sample vessel connection projection 10. The sample vessel 39 contains the sample to be analysed. As discussed above, in a preferred embodiment the sample is mixed with a lysis solution as described above. The lysis solution preferably comprises a solid support for clearing the lysate. Preferably, carboxylated beads are used. Thereby, the sample is pretreated and prepared for the analysis. The cleared sample can then enter the sample passageway 6 through the sample intake opening 4. However, it is also within the scope of the present invention that the sample mixed with the lysis solution enters the sample passageway 6 through the sample intake opening 4 and wherein lysis occurs respectively is completed in the cartridge, e.g. within the reaction chamber 38 after the reconstitution of the dry reagents, e.g. during a heating step performed in a PCR reaction.

FIG. 15 shows a further embodiment of the cartridge. Like elements have been assigned the same reference numbers but increased by the value of 100 in comparison to the comparable elements in the embodiments shown in the FIGS. 12 to 14. The embodiment shown in FIG. 15 shows that the fluid passageway B (103) can be provided over its whole length with a membrane 150. FIG. 15 also shows that the fluid passageway A (109) can be provided over its whole length with a membrane 151. FIG. 15 also shows that a lid 152 can be attached to the cartridge body 133 to tightly seal all fluid passageways. The lid 152 is attached to the cartridge body 133 in such a manner that the lid 152 closes the first channel that at least partially forms the fluid passageway B (103), the second channel that at least partially forms the sample passageway 106 and the cavity that at least partially forms the fluid passageway A (109). The lid preferably is a plastic foil. In this embodiment, only two reaction chambers are provided.

FIG. 16 is a top view of the cartridge as shown in FIG. 15. The same elements are indicated with the same numbering. Furthermore, below the cartridge the connection between the processing cartridge and the processing device in the area of detection is shown in a side view cut along the line indicated in the cartridge view. The detector is located underneath the reaction chamber and therefore, is capable of for example capturing a fluorescent signal.

FIG. 17a) shows the reaction chambers 38 (a) to 38 (d) which are provided as separate elements and which can be mounted to the corresponding connection projections of the cartridge body, thereby providing the processing cartridge. As can be seen, the four reaction chambers 38 (a) to 38 (d) are provided as one device which simplifies the handling, in particular the assembly to the cartridge. For this purpose, the reaction chambers 38 (a) to 38 (d) are connected via bond bridges 153. The side view along the line A-A is shown in FIG. 17b). It is also within the scope of the present invention to provide further reaction chambers.

FIG. 18 is a detailed view of the fluid barriers 154 that are incorporated into the sample passageway 6 and the fluid passageway A (9). The barriers are designed as small walls which function in connection with the lid 152, which is a plastic foil in the shown embodiment, as a valve. The lid 152 covers the channel and adheres to the respective walls. If a pressure is applied onto the lid 152, the channels are closed and liquids, such as water or the sample, can not pass said barrier 154. As soon as the pressure is removed from the lid, the channels of the passageway 6 and 9 open and the liquid, here the sample, e.g. the lysed sample or a lysis mixture comprising a sample mixed with a lysis buffer, can flow over said barriers 154. In an alternative design, the respective barriers 154 are attached to the lid 152 and are inserted into the channel by applying pressure to the lid. Below, a side view of the cartridge body with assembled sample vessel and reaction chamber is shown wherein the detailed view is highlighted.

FIG. 19 illustrates the system according to the present invention. The sample is collected using a swab 41 and the sample is inserted into the sample vessel 39 which comprises the lysis solution. The sample collection is also illustrated in FIG. 20 using a differently designed sample tube, having a thread and comprising a magnetic stirring bar 155. The sample vessel 39 is assembled to the cartridge body 33 which comprises the assembled reaction chambers comprising dry reagents for performing the analytical method. The respectively assembled cartridge is then entered into the processing device 160.

EXAMPLES

Example 1

Lysis of E. coli in Blood Plasma

Materials
 blood plasma (EDTA stabilized)
 E. coli glycerol stock (titer: $3.04 \times 10^8$ cells/ml; 10 µl=3× $10^6$ cells)
 Lysis buffer: 0.1% PVP MW 10.000; 0.45% Tween-20; 0.45% Nonidet P40; 10 mM Tris HCL pH 8.0; 1 mM EDTA
 Magnetic particle suspensions:
  a) MasG (MagAttract Suspension G (QIAGEN—silica beads)
  b) MasB (MagAttract Suspension B (QIAGEN—silica beads)
  c) Carboxylated magnetic particles (Seradyn)
Protocol 920 µl lysis buffer are provided in a 1.5 ml micro tube. 50 µl blood plasma are added and 20 µl bead suspension. 20 µl water was added in the reference method. 10 µl cells (undiluted) are added and the mixture is incubated at 5 min at 95° C. at 1400 rpm on an Eppendorf thermomixer. Thereby, the cells are lysed. The mixture is cooled down to room temperature and a magnetic separation (sedimentation with reference) is performed. Due to the added magnetic particles, precipitates adsorb to the particles and are collected at the bottom of the tube by using a magnet. Thereby, the lysate is cleared. The obtained supernatant (cleared lysate) is used in an E. coli quantitative PCR (1 µl and 10 µl).

qPCR Protocol

The used conditions are summarized in the following table:

| | | | |
|---|---|---|---|
| Lysate input volume | 1 µl | 10 µl | |
| Quantifast PCR Master Mix | 12.50 | 12.50 | |
| FWD | 0.10 | 0.10 | Sequence: CGATGATGCTACCCCTGAAAAACT |
| Rev | 0.10 | 0.10 | Sequence: TATTGTCGCTTGAACTGATTTCCTC |
| Pro | 0.05 | 0.05 | Sequence: CGTTGTTAAGTCAATGGAAAACCTG |
| BiDest | 11.25 | 2.25 | |
| Volume | 24 µl | 15 µl | |
| Total volume Lysate + PCR mix | 25 µl | 25 µl | |

Cycling Parameter: 5 min 95° C.; (10 sec 95° C.) 40×

Results

The results of this example are shown in FIG. 1. Shown is the Ct value of the performed PCR method. The higher the Ct value, the more PCR cycles are needed in order to achieve a certain threshold. A high Ct value therefore indicates either a low amount of nucleic acids in the sample and/or the presence of PCR inhibitors. In order to differentiate these effects, 1 µl and 10 µl of the cleared lysate were tested in parallel. As the PCR reaction using 10 µl of the cleared lysate comprises more nucleic acids, the Ct values should decrease compared to the PCR reaction, wherein 1 µl sample material is used. If no considerable decrease is seen despite the fact that more nucleic acids were subjected to the PCR reaction, this indicates that the PCR reaction is inhibited. FIG. 1 demonstrates that the addition of magnetic particles for clearing the lysate results in a considerable decrease of the Ct values with all tested particles. This demonstrates that the method according to the present invention for clearing the lysate is very effective in removing inhibitors of the amplification reaction, in particular precipitates that are formed during the lysis process. The best results were achieved with the carboxylated magnetic particles even though also silica based magnetic particles showed a considerable improvement. With the carboxylated beads, an almost ideal decrease of the Ct value is achieved. In the samples that were processed according to the reference method (wherein no magnetic particles were added to clear the lysate), despite the fact that almost 10 times more nucleic acids were added, the Ct value only decreased by approx. 0.5Ct units. This shows that the PCR was considerably inhibited due to the presence of contaminants in the supernatant. Therefore, the results of example 1 demonstrate that all tested magnetic particles were suitable to remove PCR inhibiting precipitates from the lysates. This is in particular important when intending to use a higher amount of the lysate in a quantitative PCR, because more lysate introduces more inhibitors into the amplification reaction. To efficiently remove inhibiting contaminants such as precipitates by lysate clearing is particular important when intending to use the lysate for reconstituting dried PCR reagents is shown in the subsequent experiments. However, for less complex sample types and/or other analytical methods a respective lysate clearing step is not mandatory, even though advantageous.

Example 2

Lysis of Corynebacterium in Blood

Materials
 Blood (stabilized)
 Corynebacteria glutamicum glycerol stock (titer: $1.3 \times 10^8$ cells/ml; 23 µl=$3 \times 10^6$ cells)
 Lysis buffer (see example 1)
 Magnetic particle suspensions:
  a) Ademtech carboxy beads (Ademtech)
  b) Magnosphere MK230/carboxyl (JSR Corp)
  c) Carboxylated magnetic particles (Seradyn)
Protocol 952 µl lysis buffer is provided in a 1.5 µl microtube. 50 µl blood is added and 20 µl bead suspension. 20 µl water is added instead in the reference method, wherein no lysate clearing according to the teachings of the present invention is performed. Afterwards, 23 µl cells (undiluted) are added and the mixture is incubated for 5 min at 95° C. at 1400 rpm on an Eppendorf thermomixer. The mixture is cooled down to room temperature. Afterwards, the lysate is cleared by magnetic separation in the method for clearing a lysate according to the present invention and sedimentation with the reference method. The supernatant (cleared lysate in case of magnetic separation) is used in a *Corynebacterium glutamicum* quantitative PCR (1 µl and 10 µl).

qPCR Protocol

The used PCR conditions are summarized in the following table:

| | | | |
|---|---|---|---|
| Lysate input volumen | 1 µl | 10 µl | |
| Quantifast PCR Master Mix | 12.50 | 12.50 | |
| FWD | 0.10 | 0.10 | Sequence: AAGCTCCAGCCA CCCAAAACTAC |
| Rev | 0.10 | 0.10 | Sequence: CTACCAACCACT AATGCGTCGTC |
| Pro | 0.05 | 0.05 | Sequence: ATCGCCTTCCA GACGCTCAACG |
| BiDest | 11.25 | 2.25 | |
| Volumen | 24 µl | 15 µl | |
| Total volume Lysate + PCR mix | 25 µl | 25 µl | |

Cycling Parameter: 5 min 95° C.; (10 sec 95° C.) 40x

Results

The results are shown in FIG. 2. As can be seen, the Ct values considerably improved when magnetic beads were added as can be derived from the observed decrease of the Ct values when using 10 µl cleared lysate as input material. This shows that the tested beads were able to successfully remove contaminants such as in particular precipitates from the lysate, thereby achieving a considerable lysate clearing effect. Therefore, more lysate can be used in the amplification reaction.

FIG. 3 shows that the blood precipitate can be efficiently removed with the magnetic beads irrespective of which types of magnetic particles were tested. On the left hand side a lysed sample is shown wherein no magnetic particles were added to clear the lysate. As can be seen, a red precipitate is formed at the bottom of the microtube. On the right hand side the supernatant of a cleared blood lysate is shown, which has been cleared by using magnetic particles as is taught by the third aspect of the present invention. As can be seen, the simple addition of magnetic particles enables the efficient removal of the blood precipitate, thereby clearing the lysate.

Example 3

Lysis and Direct Amplification of Vaginal Swabs

Materials
  Vaginal swab
  Lysis buffer (see example 1)
  Magnetic particle suspension: Carboxylated magnetic particles (Seradyn)
Protocol
  Vaginal swabs (endocervical swabs, Copan) were transferred into 1 ml lysis buffer. 200 µl vaginal swab sample was provided in a 1.5 ml microtube. 200 µl lysis buffer was added with and without Seradyn bead sediment on 50 µl Seradyn bead suspension. The mixture was vortexed for 20 sec and incubated for 5 min at 95° C. at 1400 rpm on an Eppendorf thermomixer. The mixture was cooled down to room temperature. Magnetic separation was performed for 2 min and the reference (without beads) was centrifuged for 1 min at maximum speed. 10 µl supernatant was used in a human H18S quantitative PCR.

qPCR Protocol

The PCR conditions were as follows:

| | | |
|---|---|---|
| Lysate input volume | 10 µl | |
| Quantifast PCR Master Mix | 12.50 | |
| FWD | 0.10 | Sequence: GCCGCTAGAGGTGAAATTCTTG |
| Rev | 0.10 | Sequence: CATTCTTGGCAAATGCTTTCG |
| Pro | 0.05 | Sequence: ACCGGCGCAAGACGGACCAGA HEX-BHQ |
| BiDest | 2.25 | |
| Volume | 15 µl | |
| Total volume Lysate + PCR mix | 25 µl | 25 µl |

Cycling Parameter: 5 min 95° C.; (10 sec 95° C.) 40x

Results

The results are shown in FIG. 4. Seven different vaginal swab samples were lysed with and without added magnetic particles and 10 µl of the respective cleared and uncleared lysates were used directly in a quantitative PCR. As can be seen, all cleared lysates enabled the performance of the PCR reaction. In all cases, the performance of the lysates that were cleared according to the teachings of the present invention was considerably better compared to the reference method, wherein the precipitates were only sedimented by centrifugation.

Example 4

Lysis and Direct Amplification with Vaginal Swabs

Materials, Protocol and Quantitative PCR Protocol

Samples were prepared as described in example 3. However, besides the Seradyn beads, also silica beads (MagAttract suspension G and MagAttract suspension B (QIAGEN) were used for clearing the lysate.

Results

FIG. 5 shows the result. As can be seen, precipitates can be cleared effectively from the lysate by using different magnetic particles either having a carboxylated or a silica surface.

Example 5

Lysis and Direct Amplification with Vaginal Swabs

Materials
  Ion exchange particles (Duolite ES468 and Amberlite XAD-7) and glass beads 0.1 mm Lysis buffer (see example 1)

Protocol

Vaginal swabs (endocervical swabs, Copan) were transferred in 1 ml lysis buffer. 15 mg particles were weighed in a 1.5 ml microtube; the reference was prepared without the addition of particles for lysate clearance. 200 µl lysis buffer and 200 µl vaginal swab sample was added and the mixture was vortexed for 20 sec. The vortexed mixture was incubated for 5 min at 95° C. at 1400 rpm on an Eppendorf thermomixer. The mixture was cooled down to room temperature and centrifuged for 1 min at maximum speed. The supernatant, i.e. the cleared lysate, was used in a human H18S qPCR.

qPCRrotocol

The quantitative PCR was performed as described in example 3. However, all lysates were also tested in conjunction with a PCR master mix including the used primers and probes that had been dried in a lyophylle. Said freeze-dried PCR mastermix including the used primers and probes was reconstituted by adding 25 µl of the uncleared lysate (reference) or 25 µl of the cleared lysate. Hence, the reconstitution of the PCR mastermix was performed by adding the cleared lysate.

Results

The results are shown in FIG. 6 and demonstrate that clearing the lysate using ion exchange particles allows a successful performance of the amplification when adding 1 µl or 10 µl of the cleared lysate to the PCR. Furthermore, the results also demonstrate that the cleared lysates can be used in order to reconstitute a dried PCR mix. This is a considerable simplification compared to prior art methods, as the cleared lysate can be directly used for reconstitution, thereby making a separate reconstitution step using for example water or a reconstitution buffer obsolete. Therefore, the respective method is particularly suitable in a lab on chip systems as is also described herein. As shown in the results, the reference method allowed performing a PCR reaction when adding 1 µl or 10 µl to a liquid PCR mastermix but failed in reconstitution of the dried PCR mix. Here, successful PCR was only possible when adding the magnetic particles for removing the precipitates from the lysate. Afterwards, the method was approx. equally effective. This demonstrates the advantages of the lysate clearing method according to present invention, in that it efficiently prepares and makes the lysate suitable for reconstituting a dried PCR mix.

Example 6

Lysis and Direct Amplification with Vaginal Swabs

Materials

Zeolite CAS:1318-02-1 Fluka, 96096
Lysis buffer (see example 1)
Suspension of carboxylated magnetic particles (Seradyn)

Protocol

Vaginal swabs (endocervical swabs, Copan) are provided in 1 ml lysis buffer. 30 mg zeolites are weighed in an 1.5 ml micro tube. In the reference, no zeolites were added. 250 µl lysis buffer was added and 40 µl of the Seradyn bead suspension. After addition of 250 µl vaginal swab sample, the mixture was vortexed for 20 sec and incubated for 5 min at 95° C. at 1400 rpm on an Eppendorf thermo mixer. The mixture was cooled down to room temperature. Magnetic separation was performed for 2 min and the cleared lysate, i.e. the supernatant, was used in a human H18S qPCR. 1 µl, 10 µl lysate were used in the normal, liquid PCR reactions and 25 µl of the cleared lysate was used in order to perform the PCR reaction with the dried PCR reagents. Here, the cleared lysate is used at the same time for reconstituting the dried PCR reagents.

qPCR Protocol

The PCR was performed as described in example 3 wherein however, in one example a PCR mix including primers and probes was dried and then reconstituted with 25 µl cleared lysate.

Results

The treatment of the vaginal swab lysates with zeolites as solid particles resulted in an elevation of the pH value. This effect resulted in a remarkable improvement of the PCR performance by more than 10 Ct values. Hence, the detection was improved by a factor of more than 1000.

FIG. 7 shows vaginal swab samples that were processed with and without zeolites according to example 6 and wherein different volumes of lysate were used directly in a quantitative PCR reaction. The dried PCR reagents were reconstituted using 25 µl of the cleared lysate. On the right hand side, the pH value of the samples is indicated. As can be seen, addition of the zeolites during lysis resulted in an elevation of the pH value of the lysed sample and hence, had the effect that the PCR reaction could be performed under optimal conditions. Thus, zeolites not only have a beneficial effect on the amplification reaction because contaminants comprised in the lysed sample such as e.g. precipitates are removed, but additionally, zeolites also have a beneficial influence on the pH value as the pH value is raised.

Example 7

Lysis and Direct Amplification of *E. coli* in Blood

Materials

Human blood
*E. coli* glycerine stock (titer: $9.2 \times 10^9$ cells/ml; 10 µl (1:30 diluted with PBS)=$3 \times 10^6$ cells)
Zeolite CAS:1318-02-1 Fluka, 96096
Lysis buffer: (see example 1)

Protocol 30 mg zeolites were weighed into a 1.5 ml microtube. The reference was performed without zeolites. 985 µl lysis buffer was added to the microtubes as well as 5 µl blood and 10 µl cells. The mixture was incubated for 5 min at 95° C. at 1400 rpm in an Eppendorf thermomixer. The mixture was cooled down to room temperature. After a short centrifugation, the supernatant was used in an *E. coli* qPCR. Here, 1 µl, 10 µl and 25 µl (for reconstitution of the dried PCR mix) were used in the subsequent PCR.

qPCR Protocol

The PCR was performed as described in example 3. For one reaction, the complete PCR master mix including primers and probes was dried in a lyophylle.

Results

The results demonstrate that zeolites can be effectively used as solid particles in order to clear the lysate from contaminants such as precipitates and therefore, make the lysate directly suitable for performing a PCR reaction. The lysates that were cleared according to the teachings of the present invention performed in the PCR and were also suitable for reconstituting the dried PCR mix.

Example 8

Lysis and Direct Amplification of *E. coli* in Buccal Swabs

Materials

Human blood
*E. coli* glycerol stock (titer: $9.2 \times 10^9$ cells/ml; 10 µl (1:30 diluted with PBS)=$3 \times 10^6$ cells)

Zeolite CAS:1318-02-1 Fluka, 96096
Buccal swabs (1 swab per cheek) were transferred in 1.1 ml lysis buffer
Lysis buffer: (see example 1)
Protocol
30 mg zeolite was weighed in an 1.5 ml microtube. The reference was prepared without zeolite. 490 μl buccal swab sample was added as well as 5 μl blood and 10 μl cells. The mixture is incubated for 5 min at 95° C. at 1400 rpm on an Eppendorf thermomixer. The mixture was cooled down to room temperature and after centrifugation, the supernatant (the cleared lysate) was used in an E. coli qPCR. Here, 1 μl, 10 μl were added in a 25 μl reaction.
qPCR Protocol
The protocol was performed as described in example 3.
Results
The results are shown in FIG. 9. As can be seen, the treatment of the buccal swab lysates with zeolites in order to clear the lysates results in a considerably improved PCR performance. On average, the Ct values are achieved app. 2.6 cycles earlier. This corresponds to an improvement of a factor 6.

Example 9

Lysis and Direct Amplification of E. coli Spiked to Stool Swabs

Materials
  Human stool samples
  The stool sample swabs were obtained as follows: A swab (puritan polyester) was wetted with water and excess water was removed. The swab was padded into a stool sample and excess sample was removed by turning the swab around its own axis. The swab was then added to a 1.5 ml microtube that was filled with 500 μl lysis buffer. By again turning the swab around its own axis at the rim of the tube and in the liquid, the stool material was transferred into the lysis buffer.
  E. coli glycerol stock (titer: 9.2×10$^9$ cells/ml; 10 μl (1:30 diluted with PBS)=3×10$^6$ cells)
  Zeolite CAS: 1318-02-1 Fluka, 96096
  Lysis buffer: (see example 1)
  Suspension of carboxylated magnetic particles (Seradyn)
Protocol
30 mg zeolite was weighed into a 1.5 ml microtube. The reference was performed without added zeolite. 250 μl of the stool sample and 50 μl Seradyn beads were added, as well as 10 μl E. coli cells. The mixture was incubated for 5 min at 95° C. at 1400 rpm in an Eppendorf thermomixer and cooled down to room temperature. Magnetic separation was performed for 2 min and the supernatant (cleared lysate) was transferred into a new tube. The supernatant was used in human H18S and E. coli qPCR (1 μl, and 10 μl).
qPCR Protocol
The quantitative PCR was performed as described in example 3.
Results
The results are shown in FIG. 10. As can be seen, the lysate clearing as is taught by the present invention even allows efficiently to clear the lysate of very difficult material such as stool thereby making the cleared lysate suitable directly for an amplification reaction without the need to first purify the nucleic acids from the sample.

Example 10

Elevation of the pH Value of Vaginal Swab Samples by the Addition of Zeolites

When performing an enzymatic process such as a PCR, it is mandatory to maintain the given pH value for the used enzyme, for example a taq DNA polymerase, in case of a PCR. Because vaginal swabs are very acidic, the pH active effect of zeolites can be particularly well demonstrated with said samples. Vaginal swab samples have a pH value of app. 4, wherein a pH value of app. 8-9 is necessary for a standard PCR reaction. In example 10 it was analyzed how the subsequent parameters influence the pH value of a vaginal swab sample: A) addition of zeolite-based molecular sieves (3 angstrom pore size) and B) addition of a lysis buffer with a higher ionic strength. In order to accentuate the effect, particularly acidic vaginal samples were used.

In variant A), 60 μl lysis buffer (see example 9, wherein additionally 100 mM Tris/HCl pH 8.5 was added) was added to 60 μl vaginal swab sample in lysis buffer (see example 9). 15 μl of the resulting mixture was added to a pH strip, to determine the pH value of the lysate.

In variant B), 60 μl lysis buffer (see example 9, wherein additionally 33 mM Tris/HCl pH 8.5 and a medium sized molecular sieve in form of particles (3 angstrom pore size) was added) was added to 60 μl vaginal swabs in lysis buffer (see example 9). 15 μl of the resulting mixture was added to a pH strip to determine the pH value. The results are shown in the subsequent table:

| pH value of the swab | pH value after variant A | pH value after variant B |
|---|---|---|
| 3.8 | 6.0 | 8-8.5 |
| 3.9 | 6.0 | 8.0 |
| 4.0 | 7.5 | 8-8.5 |
| 4.0 | 7-7.5 | 8.0 |
| 4.1 | 8.0 | 8-8.5 |
| 4.1 | 7.5-8 | 8-8.5 |
| 4.1 | 7.5 | 8-8.5 |

As can be seen, the addition of a combination of a lower buffer strength and zeolite (molecular sieve) elevates the pH value considerable better to the necessary pH value of 8-8.5 as the addition of a stronger buffer. The results are much more uniform and thus reliable. Therefore, zeolites can be used to reliably elevate the pH value of an acidic sample having a pH value below 4.5 to a pH value in a range of 8 to 8.5 which is suitable for performing an amplification reaction.

Example 11

Lysate Clearing by the Addition of Carboxylated Magnetic Particles

Vaginal swabs comprise large amount of macroscopic particles, such as loose cell layers and glycoprotein containing slime junk. As is shown by the following experiment, said particulate contaminants can be separated very well when using carboxylated magnetic particles. 50 μl vaginal swab samples in lysis buffer (see example 1) were diluted with 50 μl lysis buffer, which contained 2.5 mg carboxylated magnetic particles (Seradyn). The samples were mixed and incubated for 5 min at 95° C. Afterwards, the samples were cooled 2 min at room temperature and were magnetically separated for 1 min in order to remove precipitates. The resulting supernatants (cleared lysates) were transferred in a new reaction vessel using a pipette. As is shown in FIG. 11, the addition of the carboxylated magnetic particles to the lysed sample resulted in an excellent removal of macroscopic precipitates.

Example 12

Reconstitution of Dry PCR Reagents Using Different Methods and Lysis Procedures According to the Present Invention Materials
  Nasopharyngeal swabs
  Suspension of *C. glutamicum* cells
  lysis buffer (see example 1)
  Magnetic particle suspension: carboxylated magnetic particles (Seradyn)
Protocol
  Each swab sample was transferred into 500 µl lysis buffer. Three swab samples obtained from three donors were pooled. 1000 µl of the respective pool comprising the sample was mixed with the lysis buffer, 66 µl pre-separated SeraMag beads and 10 µl *C. glutamicum* suspension. For processing, three different methods were used:
Method 1:
  The freeze-dried quantifast PCR mastermix comprising primers and probes was reconstituted with 25 µl lysis mixture, wherein the lysis mixture comprised the sample, the lysis buffer and the magnetic beads. However, no special measures were applied to promote the lysis of the sample. Thus, reconstitution of the freeze-dried master-mix occurred using the sample comprised in the lysis buffer. Therefore, reconstitution occurred with a lysis mixture comprising the sample, which, however, was not (fully) lysed. The reconstituted PCR composition comprised the lysis buffer as well as the sample. 10 respectively reconstituted compositions were prepared and pooled. Aliquots of 24 µl were transferred in a standard PCR strip, all together 10 samples. 1.25 µl of the *C. glutamicum* suspension was added to each reaction. As lysis of the sample was under the used conditions not complete, the respective mixture, which already comprised the reconstituted PCR mix, was incubated for 5 minutes at 95° C. to promote lysis and furthermore, cooled down to room temperature for 1 minute in order to increase the formation of precipitates which constitute a contamination that could inhibit the PCR reaction. The magnetic beads were collected/separated for 1 minute. Thereby, the precipitates were bound to the beads and the lysate was cleared. 20 µl of the cleared reaction was transferred into a new PCR tube. Then, the PCR reaction was performed under the following conditions: 95° C. 10 seconds, 60° C. 30 seconds, 40 cycles. 10 samples were processed in parallel. Therefore, the heating step for promoting the denaturation and hence the lysis of the sample was performed after the reconstitution of the PCR mastermix. This allows to save process steps, because no longer initial heating step is required during the PCR.
Method 2:
  10 portions of the freeze-dried quantifast PCR mastermix comprising primers and probes was reconstituted using 25 µl of the lysis mixture, which comprised the sample, the lysis buffer and the magnetic beads. Thus, again, reconstitution occurred with the lysis mixture, wherein the sample had been only contacted with the lysis buffer, wherein, however, lysis was not yet promoted by heating. The respectively reconstituted PCR mixes were pooled and 20 Ml were transferred into PCR reaction tubes (10 samples were processed in parallel). 1 µl *C. glutamicum* suspension was added. Afterwards, the PCR reaction was directly performed using the following conditions: 95° C. 5 minutes, 95° C. 10 seconds, 60° C. 30 seconds, the last two steps were repeated in 40 cycles. This protocol is very fast, because herein, the lysis is promoted and achieved during the actual PCR.
Method 3:
  25 ml were transferred into ten reaction tubes of a PCR strip. 1.25 ml *C. glutamicum* suspension was added and the mixture was incubated at 95° to promote the lysis of the sample. The reaction was cooled down for 1 minute to room temperature and the beads were separated for 1 minute. 25 ml of the supernatant (cleared lysate) was transferred into a PCR strip comprising the freeze dried PCR mastermix for reconstitution (10 samples). 25 ml of the respective reconstituted composition was transferred into tubes and processed in a PCR as described in method 2 of this example.
  FIG. 21 shows the results. As can be seen, all three methods provide comparable results and demonstrate, that it is also possible to use a short cut of the method according to the present invention, by performing the lysis step together in the analysis step, for example during the PCR reaction. Thereby, considerable time can be saved.
  Therefore, all alternatives of the method according to the present invention can be used.

The invention claimed is:

1. A method for analysing a sample comprising one or more biomolecules, comprising:

A
- a) lysing the sample to provide a lysed sample and clearing the lysed sample;
- b) contacting at least a portion of the lysed sample with a dry composition comprising one or more reagents for performing an analytical method, thereby providing a reconstituted composition;
- c) performing the analytical method using the reconstituted composition; wherein clearing of the lysed sample comprises contacting the sample prior to, during, or after lysis with at least one solid support which binds to contaminants originating from the lysed sample, wherein the solid support comprises magnetic particles and comprises carboxyl groups on its surface;

or

B
- a) contacting the sample with a lysis solution thereby providing a lysis mixture;
- b) using the lysis mixture to reconstitute a dry composition comprising one or more reagents for performing an analytical method, thereby providing a reconstituted composition;
- c) performing the analytical method using the reconstituted composition, wherein the reconstituted composition is cleared and wherein subsequent to b), at least one step is performed which supports lysis of the sample;
- wherein clearing of the reconstituted composition comprises contacting the sample prior to, during, or after lysis with at least one solid support which binds to contaminants originating from the lysed sample, wherein the solid support comprises magnetic particles and comprises carboxyl groups on its surface.

2. The method according to claim 1, wherein clearing of the lysed sample and/or the reconstituted composition further comprises passing at least a portion of the lysed sample or the reconstituted composition through a filter or membrane.

3. The method according to claim 1, wherein the reconstitution process has at least one of the following characteristics:
- a) at least a portion of cleared lysed sample is contacted with the dry composition for reconstituting the dry composition;
- b) at least a portion of lysis mixture is contacted with the dry composition for reconstituting the dry composition;
- c) a predetermined amount of lysed sample, cleared lysed sample or lysis mixture is added to the dry composition for reconstitution;
- d) a mixture comprising the dry composition and lysed sample, cleared lysed sample or lysis mixture is agitated to assist the reconstitution process; and/or
- e) a mixture comprising the dry composition and (i) lysed sample, (ii) cleared lysed sample or (iii) lysis mixture is stirred by aid of a magnet and a magnetic material is comprised in the dry composition to assist the reconstitution process.

4. The method according to claim 1, wherein lysis is achieved or assisted by one or more of heating, a treatment with one or more enzymes, the addition of one or more chemicals and/or a mechanical treatment of the sample.

5. The method according to claim 1, wherein lysis of the sample comprises addition of a lysis solution which comprises
- (a) at least one nonionic surfactant or mixture of non-ionic detergents,
- (b) at least one polymer which prevents or reduces inhibition of a subsequent analytical method optionally by unspecific complexing of potential inhibitors;
- (c) optionally a proteolytic enzyme,
- (d) optionally a chelating agent for divalent cations and
- (e) optionally a buffer substance.

6. The method according to claim 1, wherein lysis and reconstitution of the sample comprises:
- a)
  - (i) contacting the sample with a lysis solution and the solid support for removing contaminants, optionally precipitates, thereby forming a lysis mixture;
  - (ii) heating the mixture to a temperature of at least 90° C., optionally at least 95° C.;
  - (iii) optionally cooling the lysed sample to a temperature below 50° C.;
  - (iv) clearing the lysed sample by separating the formed complex comprising the solid support and precipitates thereby providing a cleared lysate; and
  - (v) using the cleared lysate for reconstituting the dry composition;

or
- b)
  - (i) contacting the sample with a lysis solution and the solid support for removing contaminants, optionally precipitates, thereby forming a lysis mixture;
  - (ii) using the lysis mixture for reconstituting the dry composition;
  - (iii) heating the reconstituted composition to a temperature of at least 90° C., optionally at least 95° C.;
  - (iv) optionally cooling the reconstituted composition to a temperature below 50° C.; and
  - (v) clearing the reconstituted composition by separating the formed complex comprising the solid support and precipitates thereby providing a cleared reconstituted composition;

or c)
   (i) contacting the sample with a lysis solution and the solid support for removing contaminants, optionally precipitates, thereby forming a lysis mixture;
   (ii) using the lysis mixture for reconstituting the dry composition;
   (iii) subjecting the reconstituted composition to an amplification reaction which comprises at least one heating step involving a temperature of at least 90° C., optionally at least 95° C.

7. The method according to claim 1, wherein the analytical method has at least one of the following characteristics:

a) said method involves analysis of biomolecules, optionally nucleic acids, comprised in the sample;
b) the analytical method comprises a detection reaction;
c) the analytical method comprises at least one heating step involving a temperature of at least 85° C., at least 90° C. or at least 95° C.;
d) the analytical method comprises an amplification reaction;
e) the analytical method comprises a PCR or an isothermal amplification reaction;
f) the analytical method involves at least one heating step and lysis of the sample comprised in the reconstituted composition is assisted by said heating step; and/or
g) the analytical method is performed in the presence of a solid support that is added for clearing;

and/or the dry composition has at least one of the following characteristics a) said composition is a freeze-dried composition;
b) said composition comprises at least some, optionally all, reagents necessary for conducting the intended analysis method;
c) said composition comprises at least some, optionally all, reagents necessary for conducting an amplification reaction;
d) said composition comprises one or more, optionally all, of the following reagents selected from the group consisting of a polymerase, a reaction buffer suitable for performing an amplification reaction, dNTPs, primers and/or probes; and/or
e) said composition comprises a magnetic material that allows to assist a reconstitution process by enabling mixing of the composition during reconstitution by aid of a magnet.

8. The method according to claim 1, wherein the biomolecules are nucleic acids and the dry composition is a freeze-dried composition.

9. The method according to claim 1, wherein in A or B, the contaminants comprise precipitates that originate from the lysed sample.

10. The method according to claim 1, wherein during clearing of the lysed sample and/or the reconstituted composition, no substantial binding of the one or more biomolecules occurs.

11. The method according to claim 10, wherein clearing of the lysed sample and/or the reconstituted composition forms a complex with the precipitates, and wherein said complex is separated.

12. The method according to claim 1, wherein reconstitution of the dry composition occurs using the lysis mixture and wherein sample lysis is promoted by heating the reconstituted composition.

13. The method according to claim 1, wherein clearing of the lysed sample and/or the reconstituted composition further comprises addition of at least one compound or composition that binds to and/or neutralizes one or more inhibitors of the analysis method.

14. The method according to claim 1, wherein lysis is achieved by contacting the sample with a lysis solution.

15. The method according to claim 14, wherein lysis is assisted by heating.

16. The method according to claim 1, wherein for lysis of the sample at least one polymer is added which prevents or reduces an inhibition of the subsequent analytical method, optionally by unspecific complexing of potential inhibitors.

17. The method according to claim 1, wherein the lysis solution comprises a magnetic stirring bar.

18. The method according to claim 1, wherein the lysis solution comprises the solid support for clearing the lysate.

19. The method according to claim 1, wherein lysis is achieved and/or assisted by heating that is performed subsequent to reconstitution of the dry composition.

* * * * *

SEQUENCE LISTING

<160> NUMBER OF SEQ ID NOS: 9

<210> SEQ ID NO 1
<211> LENGTH: 24
<212> TYPE: DNA
<213> ORGANISM: Artificial
<220> FEATURE:
<223> OTHER INFORMATION: FWD primer

<400> SEQUENCE: 1
cgatgatgct acccctgaaa aact                                          24

<210> SEQ ID NO 2
<211> LENGTH: 25
<212> TYPE: DNA
<213> ORGANISM: Artificial

```
<220> FEATURE:
<223> OTHER INFORMATION: Rev primer

<400> SEQUENCE: 2
tattgtcgct tgaactgatt cctc                                        25

<210> SEQ ID NO 3
<211> LENGTH: 25
<212> TYPE: DNA
<213> ORGANISM: Artificial
<220> FEATURE:
<223> OTHER INFORMATION: Pro probe

<400> SEQUENCE: 3
cgttgttaag tcaatggaaa acctg                                       25

<210> SEQ ID NO 4
<211> LENGTH: 23
<212> TYPE: DNA
<213> ORGANISM: Artificial
<220> FEATURE:
<223> OTHER INFORMATION: FWD primer

<400> SEQUENCE: 4
aagctccagc cacccaaaac tac                                         23

<210> SEQ ID NO 5
<211> LENGTH: 23
<212> TYPE: DNA
<213> ORGANISM: Artificial
<220> FEATURE:
<223> OTHER INFORMATION: Rev primer

<400> SEQUENCE: 5
ctaccaacca ctaatgcgtc gtc                                         23

<210> SEQ ID NO 6
<211> LENGTH: 22
<212> TYPE: DNA
<213> ORGANISM: Artificial
<220> FEATURE:
<223> OTHER INFORMATION: Pro probe

<400> SEQUENCE: 6
atcgccttcc agacgctcaa cg                                          22

<210> SEQ ID NO 7
<211> LENGTH: 22
<212> TYPE: DNA
<213> ORGANISM: Artificial
<220> FEATURE:
<223> OTHER INFORMATION: FWD primer

<400> SEQUENCE: 7
gccgctagag gtgaaattct tg                                          22

<210> SEQ ID NO 8
<211> LENGTH: 21
<212> TYPE: DNA
<213> ORGANISM: Artificial
<220> FEATURE:
<223> OTHER INFORMATION: Rev primer

<400> SEQUENCE: 8
cattcttggc aaatgctttc g                                           21
```

```
<210> SEQ ID NO 9
<211> LENGTH: 21
<212> TYPE: DNA
<213> ORGANISM: Artificial
<220> FEATURE:
<223> OTHER INFORMATION: Pro probe

<400> SEQUENCE: 9
accggcgcaa gacggaccag a                                              21
```